United States Patent
Albani et al.

(10) Patent No.: US 12,416,632 B2
(45) Date of Patent: Sep. 16, 2025

(54) METHODS AND KITS FOR EVALUATING CLINICAL OUTCOMES OF AUTOIMMUNE DISEASE

(71) Applicant: SINGAPORE HEALTH SERVICES PTE. LTD., Singapore (SG)

(72) Inventors: Salvatore Albani, Singapore (SG); Jing Yao Leong, Singapore (SG)

(73) Assignee: SINGAPORE HEALTH SERVICES PTE. LTD., Singapore (SG)

( * ) Notice: Subject to any disclaimer, the term of this patent is extended or adjusted under 35 U.S.C. 154(b) by 764 days.

(21) Appl. No.: 16/622,901

(22) PCT Filed: Jun. 11, 2018

(86) PCT No.: PCT/SG2018/050293
§ 371 (c)(1),
(2) Date: Dec. 13, 2019

(87) PCT Pub. No.: WO2018/231151
PCT Pub. Date: Dec. 20, 2018

(65) Prior Publication Data
US 2020/0408756 A1 Dec. 31, 2020

(30) Foreign Application Priority Data

Jun. 14, 2017 (SG) .......................... 10201704905R

(51) Int. Cl.
*G01N 33/564* (2006.01)

(52) U.S. Cl.
CPC ..... *G01N 33/564* (2013.01); *G01N 2333/525* (2013.01); *G01N 2333/5412* (2013.01); *G01N 2333/70514* (2013.01); *G01N 2333/70521* (2013.01); *G01N 2333/70589* (2013.01); *G01N 2333/7158* (2013.01); *G01N 2800/102* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| | | | | |
|---|---|---|---|---|
| 2003/0049696 | A1* | 3/2003 | Norment | A61K 38/195 435/372 |
| 2016/0169891 | A1 | 6/2016 | Gorochov et al. | |

FOREIGN PATENT DOCUMENTS

| | | | | |
|---|---|---|---|---|
| JP | 2005535328 | A | 11/2005 | |
| JP | 2016532865 | A | 10/2016 | |
| WO | 2009/120341 | A2 | 10/2009 | |
| WO | WO-2015187101 | A1 * | 12/2015 | ........... G01N 33/505 |

OTHER PUBLICATIONS

Gibson DS et al. Diagnostic and prognostic biomarker discovery strategies for autoimmune disorders. J Proteomics. Apr. 18, 2010;73 (6):1045-60. doi: 10.1016/j.jprot.2009.11.013. (Year: 2010).*
McKinnon KM. Flow Cytometry: An Overview. Curr Protoc Immunol. Feb. 21, 2018;120:5.1.1-5.1.11. doi: 10.1002/cpim. (Year: 2018).*
Martínez A et al. Routine use of immunophenotype by flow cytometry in tissues with suspected hematological malignancies. Cytometry B Clin Cytom. Nov. 2003;56(1):8-15. doi: 10.1002/cyto.b.10044. (Year: 2003).*
Arroyo-Villa et al. Frequency of Th17 CD4+ T cells in early rheumatoid arthritis: a marker of anti-CCP seropositivity. PLoS One. 2012;7(8):e42189. doi: 10.1371/journal.pone.0042189. Epub Aug. 3, 2012. (Year: 2012).*
Che Y, et al. Circulating memory T follicular helper subsets, Tfh2 and Tfh17, participate in the pathogenesis of Guillain-Barré syndrome. Sci Rep. Feb. 11, 2016;6:20963. doi: 10.1038/srep20963. (Year: 2016).*
Sun et al. Administration of agonistic anti-4-1BB monoclonal antibody leads to the amelioration of experimental autoimmune encephalomyelitis. J Immunol. Feb. 1, 2002;168(3):1457-65. doi: 10.4049/jimmunol.168.3.1457. (Year: 2002).*
Miller et al. 4-1BB-specific monoclonal antibody promotes the generation of tumor-specific immune responses by direct activation of CD8 T cells in a CD40-dependent manner. J Immunol. Aug. 15, 2002;169(4):1792-800. doi: 10.4049/jimmunol. (Year: 2002).*
Paulissen et al. Synovial fibroblasts directly induce Th17 pathogenicity via the cyclooxygenase/prostaglandin E2 pathway, independent of IL-23. J Immunol. Aug. 1, 2013;191(3):1364-72. doi: 10.4049/jimmunol.1300274. (Year: 2013).*
Spreafico et al. A circulating reservoir of pathogenic-like CD4+ T cells shares a genetic and phenotypic signature with the inflamed synovial micro-environment. Ann Rheum Dis. Feb. 2016;75(2):459-65. doi: 10.1136/annrheumdis-2014-206226. Epub Dec. 12, 2014. (Year: 2014).*

(Continued)

*Primary Examiner* — Anne M. Gussow
*Assistant Examiner* — Brianna K Swartwout
(74) *Attorney, Agent, or Firm* — JCIP; Joseph G. Chu

(57) ABSTRACT

Methods and kits for evaluating a clinical outcome of an autoimmune disease, specifically disease flare e.g. if the subject stops taking the biologic disease modifying antirheumatic drug (DMARD), by comparing biomarkers of CD45RA, TNF-alpha and/or CXCR5 from $CD3^+CD4^+$ T cell population are disclosed. In a specific embodiment, the ratio of first subset of $CD3^+CD4^+CD45RA-TNFA^+$ (memory) T cells to a second subset comprising $CD3^+CD4^+CD45RA^+TNFA^+$ (naïve) T cell is determined, wherein an increase in the ratio indicates a disease flare state of juvenile idiopathic arthritis (JIA). In another embodiment, enrichment of $CD45RA-CR5^+$ subset among the T cell population indicates likelihood of flare state in JIA via memory persistence enhancement through B cell interaction. In other embodiments, additional markers including IL-6, CCR6, CD152 and PD1 are also determined, and the enrichment of $CD45RA-TNFA^+IL-6^+$ subset among the T cell population indicates a likelihood of amplification of the autoimmune disease.

8 Claims, 21 Drawing Sheets
Specification includes a Sequence Listing.

(56) References Cited

OTHER PUBLICATIONS

Hoff H. CTLA-4 (CD152) inhibits T cell function by activating the ubiquitin ligase Itch. Mol Immunol. Jun. 2010;47(10):1875-81. doi: 10.1016/j.molimm.2010.03.017. (Year: 2010).*
Le Coz C, Joublin A, Pasquali J-L, Korganow A-S, Dumortier H, et al. (2013) Circulating TFH Subset Distribution is Strongly Affected in Lupus Patients with an Active Disease. PLoS One 8(9): e75319. doi:10.1371/journal.pone.0075319 (Year: 2013).*
Brennan et al. Resting CD4+ effector memory T cells are precursors of bystander-activated effectors: a surrogate model of rheumatoid arthritis synovial T-cell function. Arthritis Research & Therapy 2008, 10:R36 (doi:10.1186/ar2390) (Year: 2008).*
Arroyo-Villa et al. Constitutively altered frequencies of circulating follicullar helper T cell counterparts and their subsets in rheumatoid arthritis. Arthritis Research & Therapy 2014, 16:500. http://arthritis-research.com/content/16/6/500 (Year: 2014).*
Ferreira et al. IL-21 production by CD4+ effector T cells and frequency of circulating follicular helper T cells are increased in type 1 diabetes patients. Diabetologia. (2015) 58:781-791. DOI 10.1007/s00125-015-3509-8 (Year: 2015).*
Spiztzer et al. Cell. 2016. 165(4): 780-791 (Year: 2016).*
Choi et al. Apr. 2015. Arth Rheumatic. 67(4): 988-909 (Year: 2015).*
Thong et al. Dec. 26, 2016. Rheumatol. 56:13-i13 (Year: 2016).*
Le Coz et al. Sep. 2016. PLoS One. 8(9):e75319. (Year: 2016).*
Almanzar et al. May 21, 2013. J Med Case Rep. 7:135 (Year: 2013).*
Hashkes et al. 2008. Ch. 7 Juvenile Idiopathic Arthritis: C. Treatment and Assessment in J.H. Klippel, et al., Ed. Primer on the Rheumatic Diseases. (pp. 154-162). Springer. (Year: 2008).*
Zheng et al. J Immunol. Aug. 15, 2004. 173(4):2428-2434 (Year: 2004).*
Crawley et al. 1998. Clin Immunol Newsletter. 18(10):111-118 (Year: 1998).*
Van Kooten et al. 1991. J Immunol. 146(8):2654-2658 (Year: 1991).*
Okazaki et al. Trends in Immunology. Apr. 2006. 27(4):195-201 (Year: 2006).*
Simpson et al. Jan. 2010. Arth Rheum. 62(1):234-244 (Year: 2010).*
Horneff et al. May 21, 2013. Ann Theum Dis. 73:1114-112 (Year: 2013).*
Leong J.Y. et al., High Dimensional Interrogation of the T cell Immunome in Polyarticular Juvenile Idiopathic Arthritis Patients. Arthritis Rheumatol, Sep. 28, 2016, vol. 68, No. Suppl 10, pp. 1-4550 [Retrieved on Sep. 5, 2018]<DOI:10.1002/ART.39977> Abstract No. 2417.
Ponchel F. et al., An immunological biomarker to predict MTX response in early RA. Ann Rheum Dis, Aug. 29, 2013, vol. 73, No. 11, pp. 2047-2053 [Retrieved on Sep. 5, 2018] <DOI: 10.1136/ANNRHEUMDIS-2013-203566> Abstract; Fig. 1C; p. 2047, right col. para. 2, p. 2048, right col. para. 3, p. 2049, left col. para. 2.
Bystrom J. et al., THU0500 Cytokine Production Identifies A Subset of Rheumatoid Arthritis Patients T Lymphocytes That is Associated with Responsiveness to Biologic Anti-TNF-Alpha Agents. Ann Rheum Dis, Jun. 10, 2014, vol. 73, p. 356 [Retrieved on Sep. 5, 2018] <DOI: 10.1136/ANNRHEUMDIS-2014-EULAR.4637> Abstract.
Levesque M.C. et al., Association of T follicular helper/Th17 T cell and Memory B Cell Populations in RA with disease activity and therapy with TNF antagonists. Atihritis Rheumatol, Oct. 1, 2013, vol. 65, No. Suppl 10, pp. S1-S1331 [Retrieved on Sep. 5, 2018] <DOI: 10.1002/ART.38216> Abstract No. 2431.
Zhang Y. et al., Elevated circulating Th17 and follicular helper CD4+ T cells in patients with rheumatoid arthritis. APMIS, Apr. 27, 2015, vol. 123, No. 8, pp. 659-666 [Retrieved on Sep. 5, 2018] <DOI: 10.1111/APM.12399> Abstract; Fig. 1E & F.
Yeo J.G. et al., A Dichotomy of Regulatory Immunome Is Related to Disease Activity in Juvenile Systemic Lupus Erythematosus. Arthritis Rheumatol, Sep. 28, 2016, vol. 68, No. Suppl 10, pp. 1-4550 [Retrieved on Sep. 5, 2018] <DOI: 10.1002/ART.39977> Abstract No. 1840.
Kikuchi J. et al., Proportions of Circulating Follicular Helper T Cells and Complement Levels, White Blood Cell Counts, and Skin Manifestations in Patients with Active Systemic Lupus Erythematosus. Arthritis Rheumatol, Sep. 28, 2016, vol. 68, No. Suppl 10, pp. 1-4550 [Retrieved on Sep. 5, 2018] <DOI: 10.1002/ART.39977> Abstract No. 2861.
Meednu N. et al., Comprehensive immune-phenotyping of follicular helper T cells and B cells subpopulations in primary Sjogren's syndrome. Arthritis Rheumatol, Sep. 28, 2016, vol. 68, No. Suppl 10, pp. 1-4550 [Retrieved on Sep. 5, 2018] <DOI: 10.1002/ART.39977> Abstract No. 655.
Kozlowska A. et al, Fyn and CD70 Expression in CD4+ T Cells from Patients With Systemic Lupus Erythematosus. The Journal of Rheumatology, Jan. 1, 2010, vol. 37, No. 1, pp. 53-59 [Retrieved on Sep. 5, 2018] <DOI: 10.3899/JRHEUM.090424> Abstract.
Zastepa E. et al, Naive CD4 T-cell activation identifies MS patients having rapid transition to progressive MS. Neurology, Jan. 22, 2014, vol. 82, No. 8, pp. 681-690 [Retrieved on Sep. 5, 2018] <DOI: 10.1212/WNL.0000000000000146> Methods.
Leong J.Y. et al., Persistence of Pathogenic CD4 Memory T cells Revealed through Cytometry Time of Flight in Juvenile Idiopathic Arthritic Patients with Disease Resurgence upon Withdrawal of Anti-TNFA Biologics. Arthritis Rheumatol, Sep. 18, 2017, vol. 69, No. Suppl 10, pp. 1-4481 [Retrieved on Sep. 5, 2018] <DOI: 10.1002/ART.40321> Abstract No. 953.
ISR and Written Opinion in PCT/SG2018/050293.
Almanzar, G. et al., Increased replication of CD4+ naive T cells and changes in T cell homeostasis in a case of acute exacerbation of juvenile idiopathic arthritis: a case comparison study, Journal of Medical Case Reports, May 21, 2013, vol. 7, 1-8.
Notice of Reasons for Rejection dated May 10, 2022 for Japanese Application No. 2019-568310.
Leong, J.Y. et al., High dimensional interrogation of the T cell immunome in polyarticular juvenile idiopathic arthritis patients, Arthritis Rheumatol, Sep. 28, 2016, vol. 68, No. 10, 3171-3173.
Examination Report No. 1 dated Nov. 30, 2023 for Australian Application No. 2018285469.

* cited by examiner

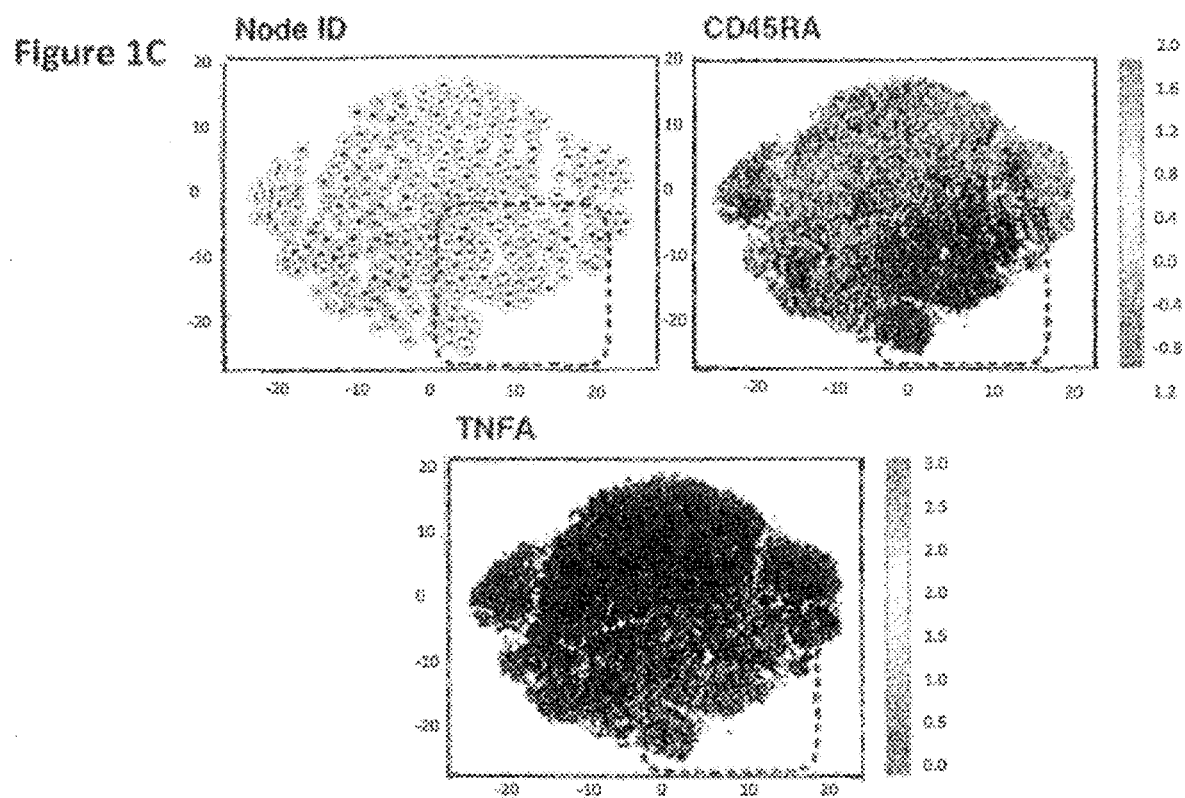

Figure 5E
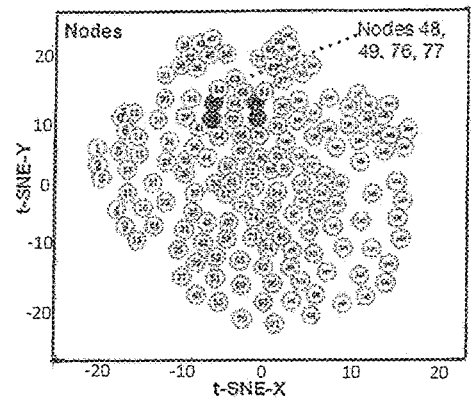
Figure 5F
| Node ID | Node Phenotype |
|---|---|
| 196 | CD3- CD4- CD45RA- TNF-alpha+ |
| 209 | CD3- CD4- CD45RA- TNF-alpha+ CD127- |
| 211 | CD3- CD4- CD45RA- TNF-alpha+ CD154- |
| 222 | CD3- CD4- CD45RA- TNF-alpha+ CD28- ICOS- CD154- |
| 178 | CD3- CD4- CD45RA- TNF-alpha- CXCR5- CD69+ CCR6- |
Figure 5G
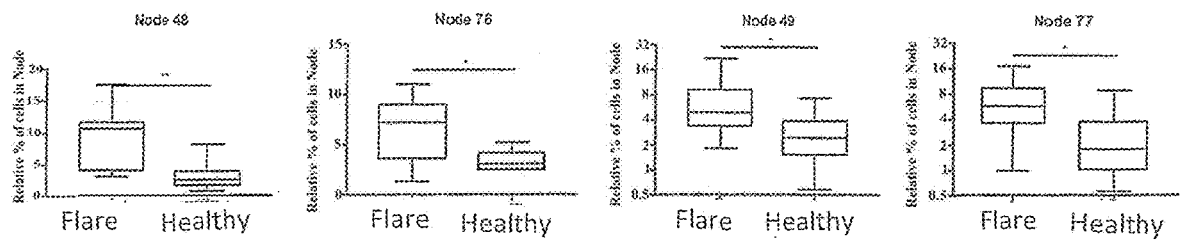
Figure 5H
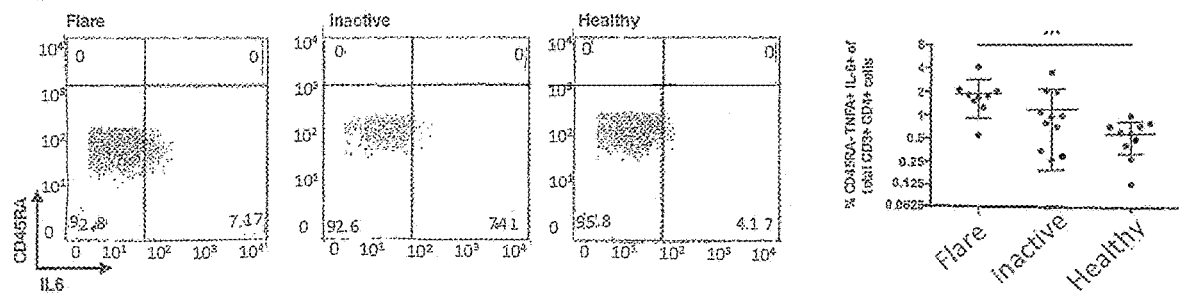

Figure 5I
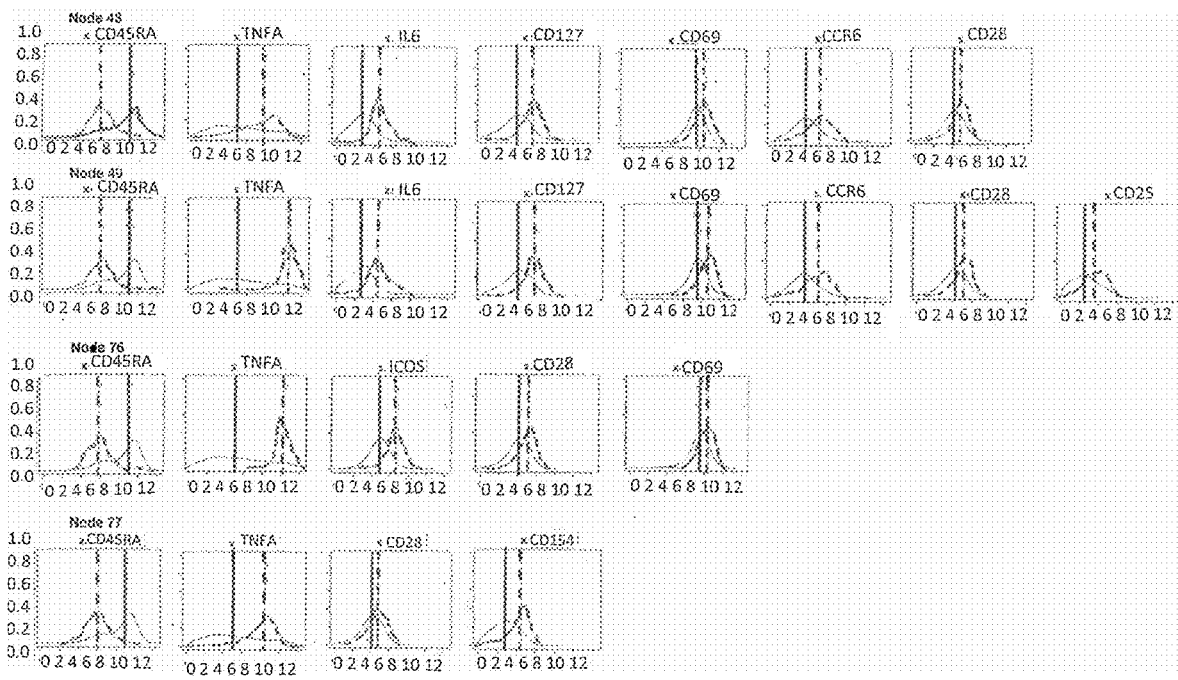
Figure 6A-E
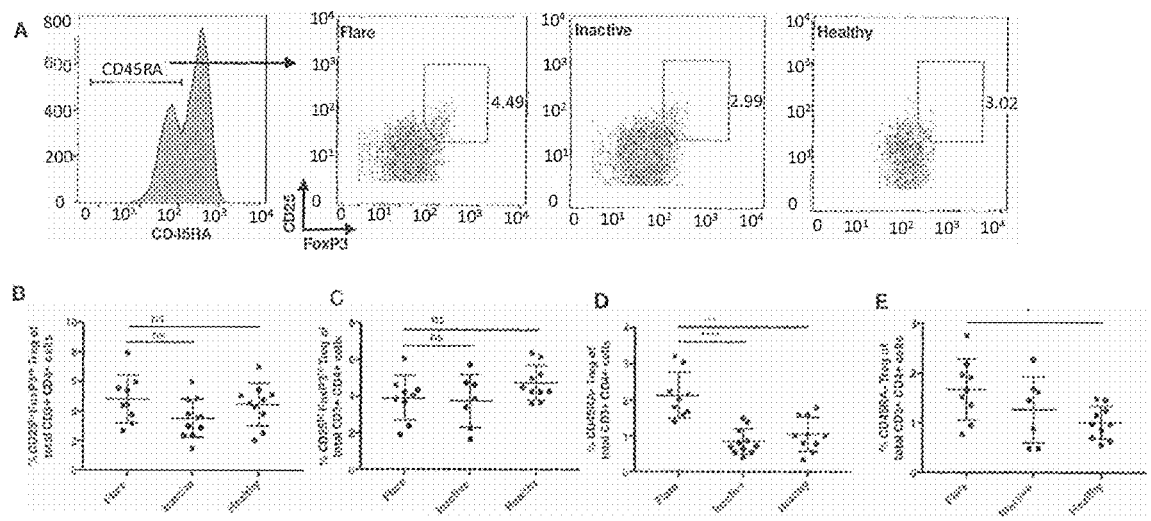

Figure 7A-G
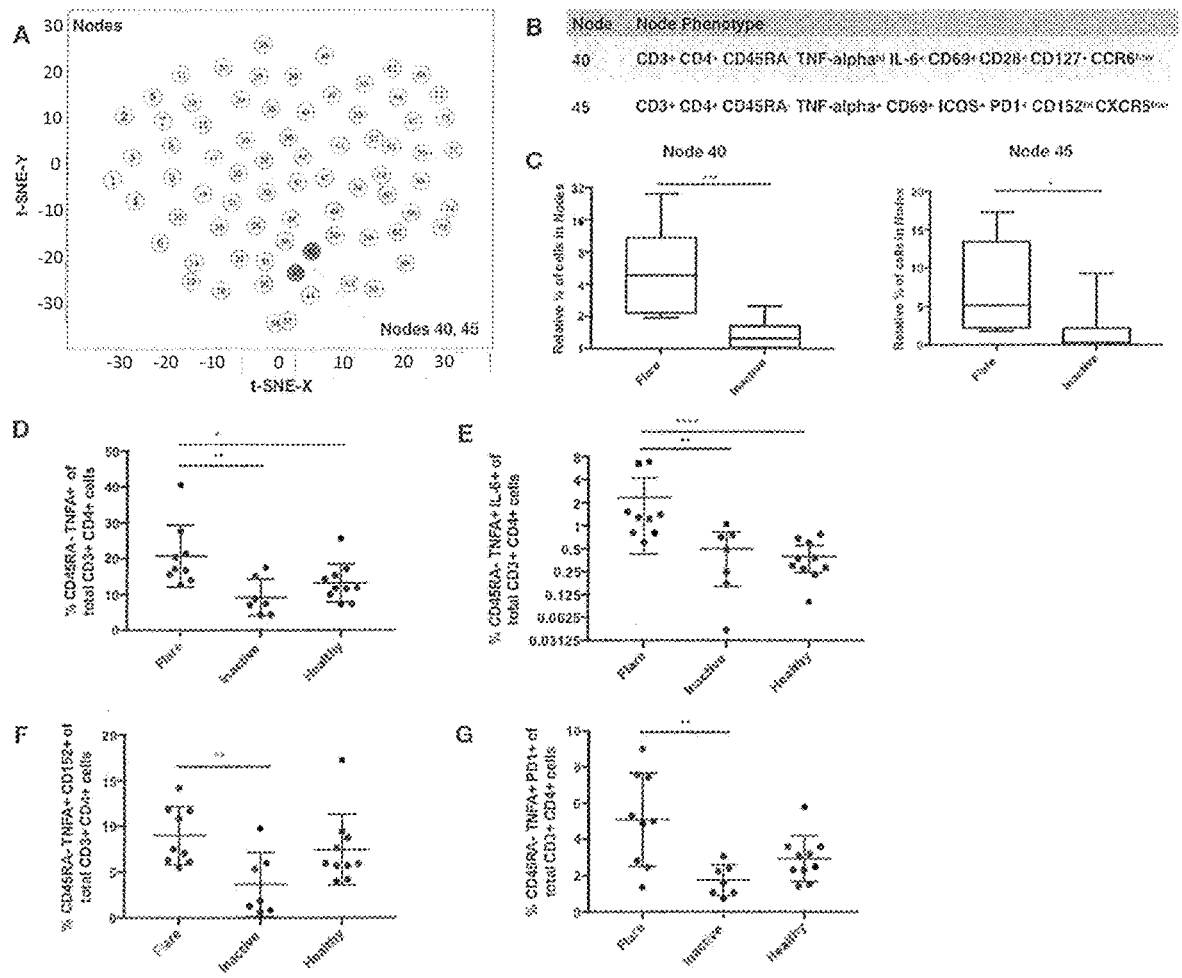
Figure 8A
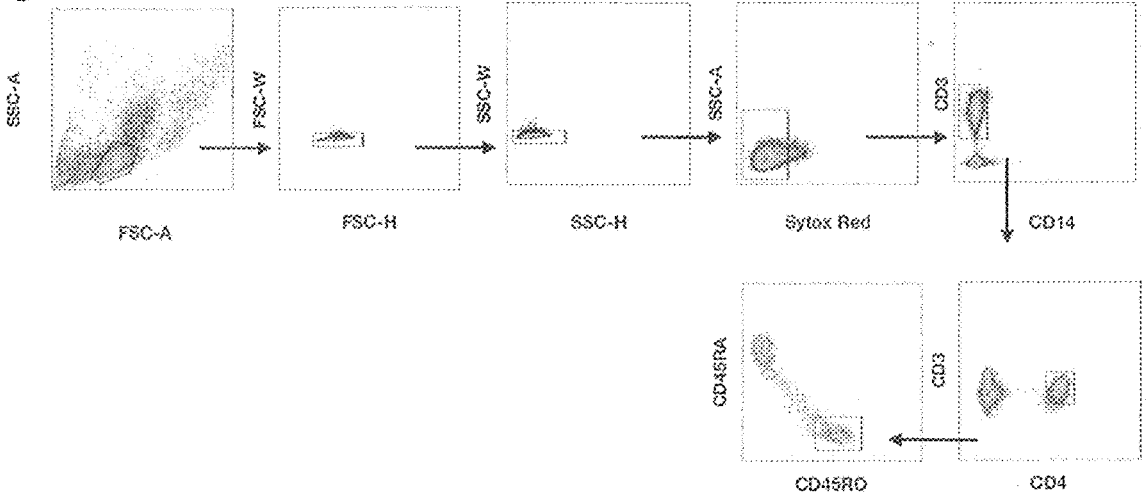

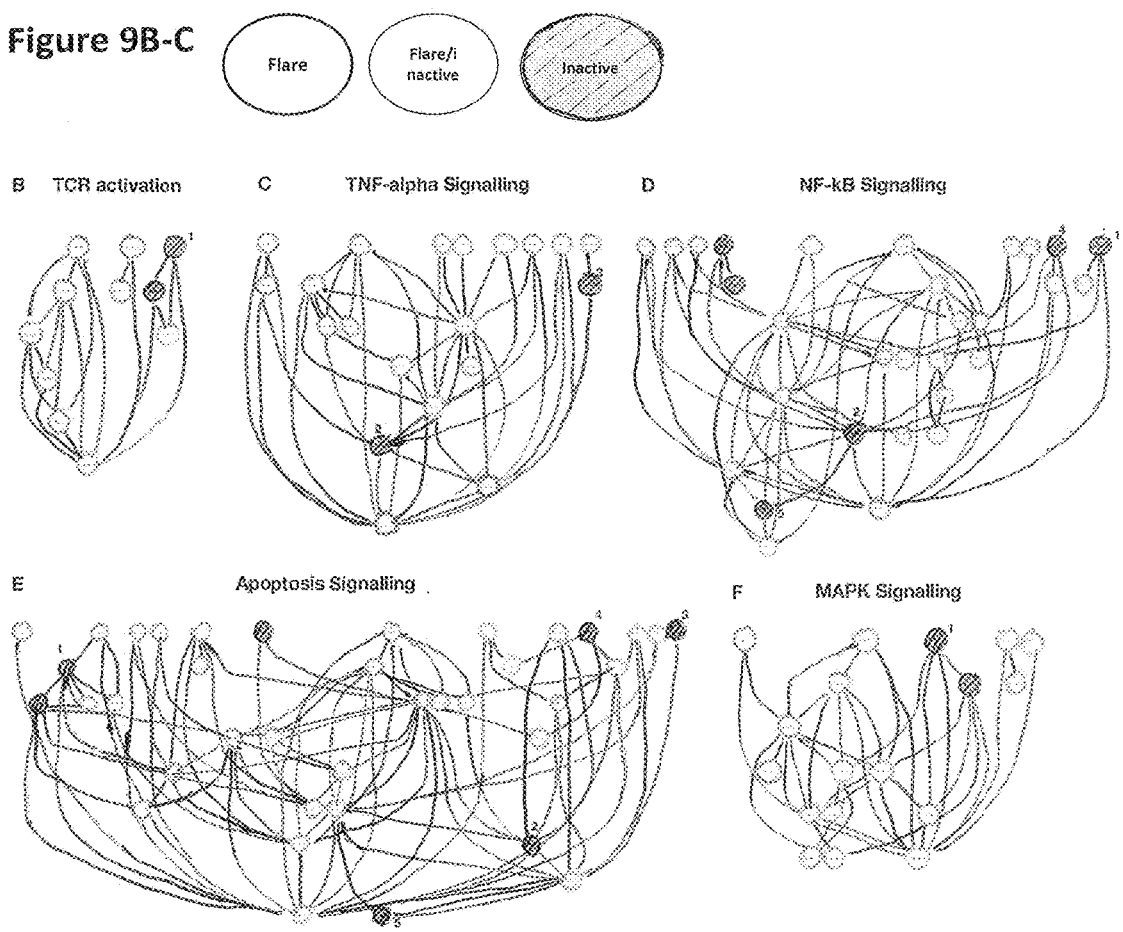
Figure 9B-C
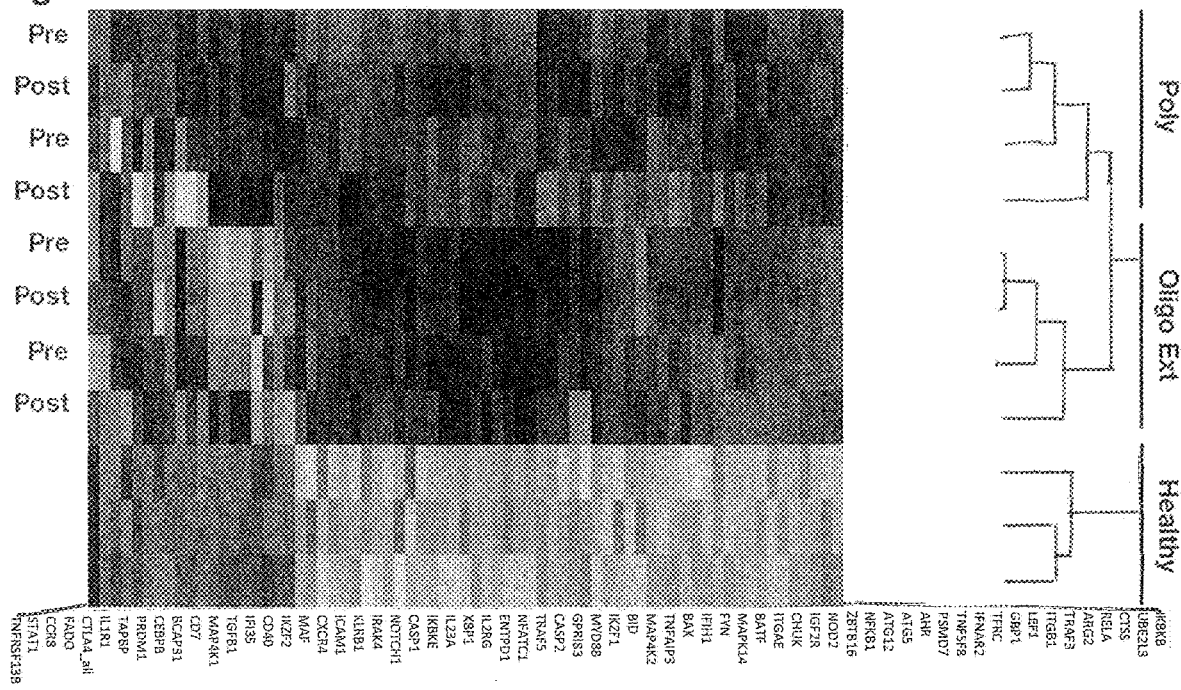
Figure 9G

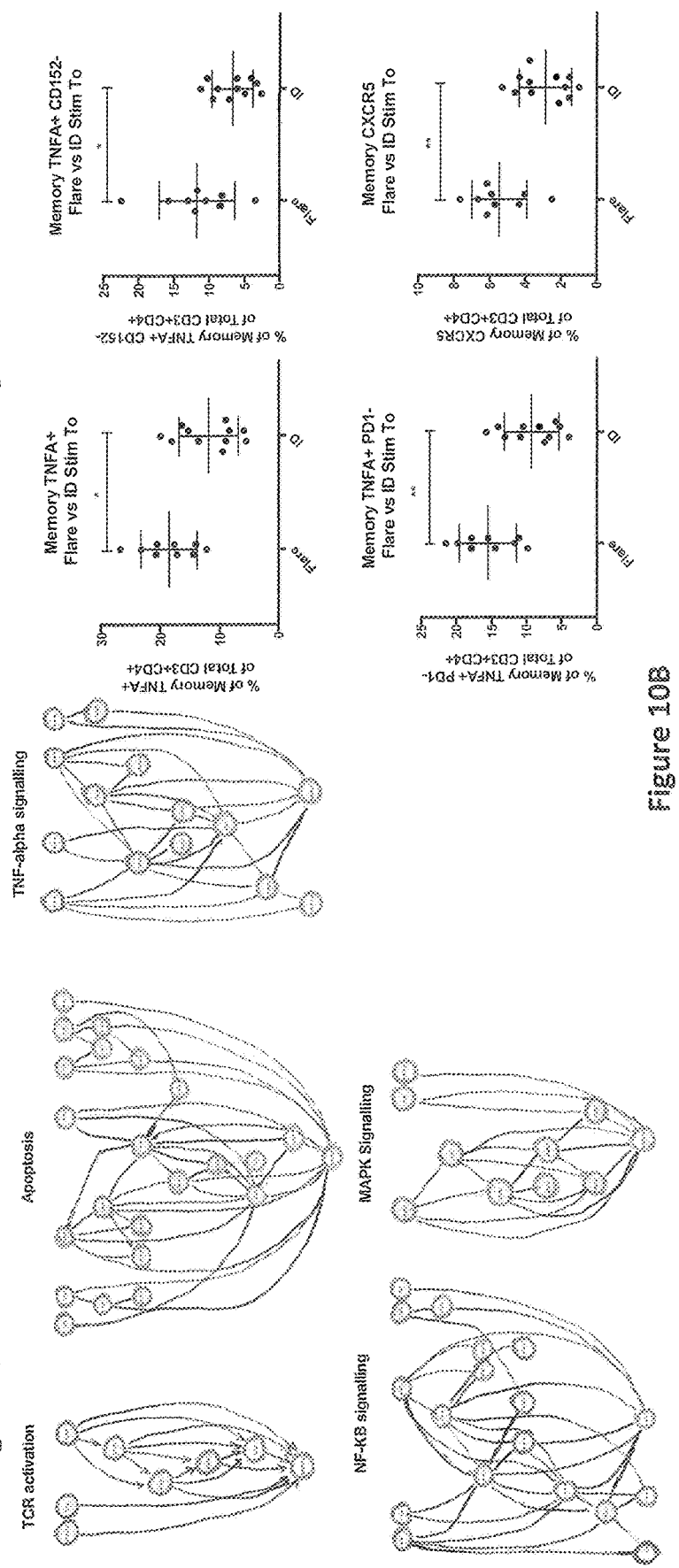
Figure 9H
Figure 10A
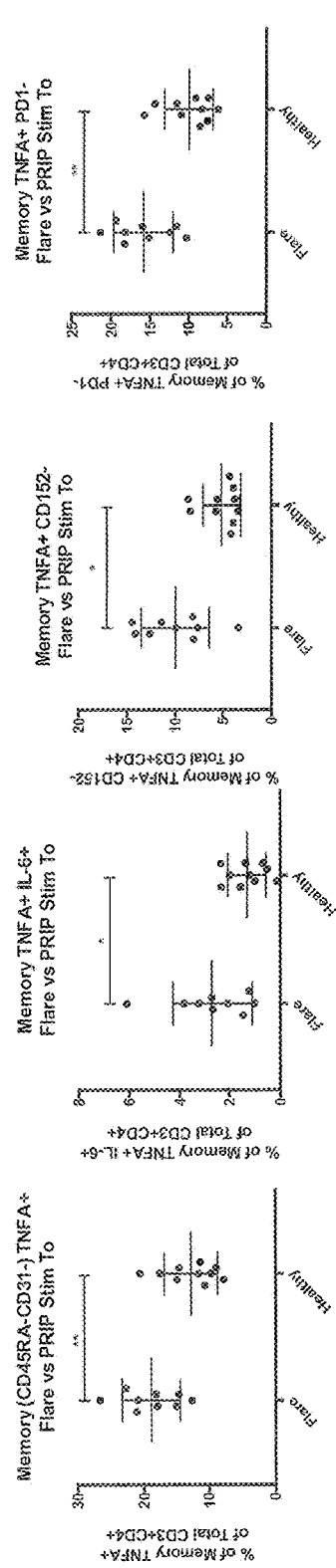
Figure 10B

SEQUENCE LISTING

```
<160> NUMBER OF SEQ ID NOS: 82

<210> SEQ ID NO 1
<211> LENGTH: 5
<212> TYPE: PRT
<213> ORGANISM: Artificial Sequence
<220> FEATURE:
<223> OTHER INFORMATION: CD3 HCDR1

<400> SEQUENCE: 1

Gly Tyr Gly Met His
1               5

<210> SEQ ID NO 2
<211> LENGTH: 17
<212> TYPE: PRT
<213> ORGANISM: Artificial Sequence
<220> FEATURE:
<223> OTHER INFORMATION: CD3 HCDR2

<400> SEQUENCE: 2

Val Ile Trp Tyr Asp Gly Ser Lys Lys Tyr Tyr Val Asp Ser Val Lys
1               5                   10                  15

Gly

<210> SEQ ID NO 3
<211> LENGTH: 9
<212> TYPE: PRT
<213> ORGANISM: Artificial Sequence
<220> FEATURE:
<223> OTHER INFORMATION: CD3 HCDR3

<400> SEQUENCE: 3

Gln Met Gly Tyr Trp His Phe Asp Leu
1               5
```

```
<210> SEQ ID NO 4
<211> LENGTH: 11
<212> TYPE: PRT
<213> ORGANISM: Artificial Sequence
<220> FEATURE:
<223> OTHER INFORMATION: CD3 LCDR1

<400> SEQUENCE: 4

Arg Ala Ser Gln Ser Val Ser Ser Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CD3 LCDR2

<400> SEQUENCE: 5

Asp Ala Ser Asn Arg Ala Thr
1               5

<210> SEQ ID NO 6
<211> LENGTH: 10
<212> TYPE: PRT
<213> ORGANISM: Artificial Sequence
<220> FEATURE:
<223> OTHER INFORMATION: CD3 LCDR3

<400> SEQUENCE: 6

Gln Gln Arg Ser Asn Trp Pro Pro Leu Thr
1               5                   10

<210> SEQ ID NO 7
<211> LENGTH: 11
<212> TYPE: PRT
<213> ORGANISM: Artificial Sequence
<220> FEATURE:
<223> OTHER INFORMATION: CD4 HCDR1

<400> SEQUENCE: 7

Leu Ala Ser Glu Asp Ile Tyr Ser Asp Leu Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: CD4 HCDR2

<400> SEQUENCE: 8

Asn Thr Asp Thr Leu Gln Asn
1               5

<210> SEQ ID NO 9
<211> LENGTH: 9
<212> TYPE: PRT
<213> ORGANISM: Artificial Sequence
<220> FEATURE:
<223> OTHER INFORMATION: CD4 HCDR3

<400> SEQUENCE: 9

Gln Gln Tyr Asn Asn Tyr Pro Trp Thr
1               5
```

```
<210> SEQ ID NO 10
<211> LENGTH: 5
<212> TYPE: PRT
<213> ORGANISM: Artificial Sequence
<220> FEATURE:
<223> OTHER INFORMATION: CD4 LCDR1

<400> SEQUENCE: 10

Asn Tyr Gly Met Ala
1               5

<210> SEQ ID NO 11
<211> LENGTH: 17
<212> TYPE: PRT
<213> ORGANISM: Artificial Sequence
<220> FEATURE:
<223> OTHER INFORMATION: CD4 LCDR2

<400> SEQUENCE: 11

Thr Ile Ser His Asp Gly Ser Asp Thr Tyr Phe Arg Asp Ser Val Lys
1               5                   10                  15
Gly

<210> SEQ ID NO 12
<211> LENGTH: 9
<212> TYPE: PRT
<213> ORGANISM: Artificial Sequence
<220> FEATURE:
<223> OTHER INFORMATION: CD4 LCDR3

<400> SEQUENCE: 12

Gln Gly Thr Ile Ala Gly Ile Arg His
1               5

<210> SEQ ID NO 13
<211> LENGTH: 5
<212> TYPE: PRT
<213> ORGANISM: Artificial Sequence
<220> FEATURE:
<223> OTHER INFORMATION: CD45RA HCDR1

<400> SEQUENCE: 13

Asn Tyr Ile Ile His
1               5

<210> SEQ ID NO 14
<211> LENGTH: 17
<212> TYPE: PRT
<213> ORGANISM: Artificial Sequence
<220> FEATURE:
<223> OTHER INFORMATION: CD45RA HCDR2

<400> SEQUENCE: 14

Tyr Phe Asn Pro Tyr Asn His Gly Thr Lys Tyr Asn Glu Lys Phe Lys
1               5                   10                  15
Gly

<210> SEQ ID NO 15
<211> LENGTH: 9
<212> TYPE: PRT
<213> ORGANISM: Artificial Sequence
<220> FEATURE:
<223> OTHER INFORMATION: CD45RA HCDR3

<400> SEQUENCE: 15

Ser Gly Pro Tyr Ala Trp Phe Asp Thr
```

```
1               5

<210> SEQ ID NO 16
<211> LENGTH: 11
<212> TYPE: PRT
<213> ORGANISM: Artificial Sequence
<220> FEATURE:
<223> OTHER INFORMATION: CD45RA LCDR1

<400> SEQUENCE: 16

Arg Ala Ser Gln Asn Ile Gly Thr Ser Ile Gln
1               5                   10

<210> SEQ ID NO 17
<211> LENGTH: 7
<212> TYPE: PRT
<213> ORGANISM: Artificial Sequence
<220> FEATURE:
<223> OTHER INFORMATION: CD45RA LCDR2

<400> SEQUENCE: 17

Ser Ser Ser Glu Ser Ile Ser
1               5

<210> SEQ ID NO 18
<211> LENGTH: 9
<212> TYPE: PRT
<213> ORGANISM: Artificial Sequence
<220> FEATURE:
<223> OTHER INFORMATION: CD45RA LCDR3

<400> SEQUENCE: 18

Gln Gln Ser Asn Thr Trp Pro Phe Thr
1               5

<210> SEQ ID NO 19
<211> LENGTH: 5
<212> TYPE: PRT
<213> ORGANISM: Artificial Sequence
<220> FEATURE:
<223> OTHER INFORMATION: TNF-alpha HCDR1

<400> SEQUENCE: 19

Asn Tyr Trp Met Asn
1               5

<210> SEQ ID NO 20
<211> LENGTH: 20
<212> TYPE: PRT
<213> ORGANISM: Artificial Sequence
<220> FEATURE:
<223> OTHER INFORMATION: TNF-alpha HCDR2

<400> SEQUENCE: 20

Glu Val Arg Leu Gln Ser Asp Asn Phe Thr Thr Ser His Tyr Ala Glu
1               5                   10                  15

Ser Val Lys Gly
            20

<210> SEQ ID NO 21
<211> LENGTH: 4
<212> TYPE: PRT
<213> ORGANISM: Artificial Sequence
<220> FEATURE:
<223> OTHER INFORMATION: TNF-alpha HCDR3

<400> SEQUENCE: 21
```

Pro Phe Ala Tyr
1

<210> SEQ ID NO 22
<211> LENGTH: 10
<212> TYPE: PRT
<213> ORGANISM: Artificial Sequence
<220> FEATURE:
<223> OTHER INFORMATION: TNF-alpha LCDR1

<400> SEQUENCE: 22

Ser Ala Ser Ser Ser Val Ser Phe Met Tyr
1               5                   10

<210> SEQ ID NO 23
<211> LENGTH: 7
<212> TYPE: PRT
<213> ORGANISM: Artificial Sequence
<220> FEATURE:
<223> OTHER INFORMATION: TNF-alpha LCDR2

<400> SEQUENCE: 23

Asp Ala Ser Ile Leu Ala Ser
1               5

<210> SEQ ID NO 24
<211> LENGTH: 10
<212> TYPE: PRT
<213> ORGANISM: Artificial Sequence
<220> FEATURE:
<223> OTHER INFORMATION: TNF-alpha LCDR3

<400> SEQUENCE: 24

Gln Gln Trp Ser Asp Tyr Ser Pro Arg Thr
1               5                   10

<210> SEQ ID NO 25
<211> LENGTH: 10
<212> TYPE: PRT
<213> ORGANISM: Artificial Sequence
<220> FEATURE:
<223> OTHER INFORMATION: CXCR5 HCDR1

<400> SEQUENCE: 25

Gly Phe Ser Leu Ile Asp Tyr Gly Val Asn
1               5                   10

<210> SEQ ID NO 26
<211> LENGTH: 9
<212> TYPE: PRT
<213> ORGANISM: Artificial Sequence
<220> FEATURE:
<223> OTHER INFORMATION: CXCR5 HCDR2

<400> SEQUENCE: 26

Val Ile Trp Gly Asp Gly Thr Thr Tyr
1               5

<210> SEQ ID NO 27
<211> LENGTH: 3
<212> TYPE: PRT
<213> ORGANISM: Artificial Sequence
<220> FEATURE:
<223> OTHER INFORMATION: CXCR5 HCDR3

<400> SEQUENCE: 27

```
Ile Val Tyr
1

<210> SEQ ID NO 28
<211> LENGTH: 16
<212> TYPE: PRT
<213> ORGANISM: Artificial Sequence
<220> FEATURE:
<223> OTHER INFORMATION: CXCR5 LCDR1

<400> SEQUENCE: 28

Arg Ser Ser Lys Ser Leu Leu His Ser Ser Gly Lys Thr Tyr Leu Tyr
1               5                   10                  15

<210> SEQ ID NO 29
<211> LENGTH: 7
<212> TYPE: PRT
<213> ORGANISM: Artificial Sequence
<220> FEATURE:
<223> OTHER INFORMATION: CXCR5 LCDR2

<400> SEQUENCE: 29

Arg Leu Ser Asn Leu Ala Ser
1               5

<210> SEQ ID NO 30
<211> LENGTH: 9
<212> TYPE: PRT
<213> ORGANISM: Artificial Sequence
<220> FEATURE:
<223> OTHER INFORMATION: CXCR5 LCDR3

<400> SEQUENCE: 30

Met Gln His Leu Glu Tyr Pro Tyr Thr
1               5

<210> SEQ ID NO 31
<211> LENGTH: 10
<212> TYPE: PRT
<213> ORGANISM: Artificial Sequence
<220> FEATURE:
<223> OTHER INFORMATION: IL-6 HCDR1

<400> SEQUENCE: 31

Gly Glu Asn Phe Asn Asp Tyr Phe Met Asn
1               5                   10

<210> SEQ ID NO 32
<211> LENGTH: 19
<212> TYPE: PRT
<213> ORGANISM: Artificial Sequence
<220> FEATURE:
<223> OTHER INFORMATION: IL-6 HCDR2

<400> SEQUENCE: 32

Gln Met Arg Asn Lys Asn Tyr Gln Tyr Gly Thr Tyr Tyr Ala Glu Ser
1               5                   10                  15

Leu Glu Gly

<210> SEQ ID NO 33
<211> LENGTH: 9
<212> TYPE: PRT
<213> ORGANISM: Artificial Sequence
<220> FEATURE:
<223> OTHER INFORMATION: IL-6 HCDR1

<400> SEQUENCE: 33
```

```
Glu Ser Tyr Tyr Gly Phe Thr Ser Tyr
1               5

<210> SEQ ID NO 34
<211> LENGTH: 11
<212> TYPE: PRT
<213> ORGANISM: Artificial Sequence
<220> FEATURE:
<223> OTHER INFORMATION: IL-6 LCDR1

<400> SEQUENCE: 34

Gln Ala Ser Gln Asp Ile Gly Ile Ser Leu Ser
1               5                   10

<210> SEQ ID NO 35
<211> LENGTH: 7
<212> TYPE: PRT
<213> ORGANISM: Artificial Sequence
<220> FEATURE:
<223> OTHER INFORMATION: IL-6 LCDR2

<400> SEQUENCE: 35

Asn Ala Asn Asn Leu Ala Asp
1               5

<210> SEQ ID NO 36
<211> LENGTH: 8
<212> TYPE: PRT
<213> ORGANISM: Artificial Sequence
<220> FEATURE:
<223> OTHER INFORMATION: IL-6 LCDR3

<400> SEQUENCE: 36

Gln His Asn Ser Ala Pro Tyr Thr
1               5

<210> SEQ ID NO 37
<211> LENGTH: 5
<212> TYPE: PRT
<213> ORGANISM: Artificial Sequence
<220> FEATURE:
<223> OTHER INFORMATION: IFG-g HCDR1

<400> SEQUENCE: 37

Ser Tyr Ala Met Ser
1               5

<210> SEQ ID NO 38
<211> LENGTH: 17
<212> TYPE: PRT
<213> ORGANISM: Artificial Sequence
<220> FEATURE:
<223> OTHER INFORMATION: IFG-g HCDR2

<400> SEQUENCE: 38

Ala Ile Ser Gly Ser Gly Gly Ser Thr Tyr Tyr Ala Asp Ser Val Lys
1               5                   10                  15
Gly

<210> SEQ ID NO 39
<211> LENGTH: 14
<212> TYPE: PRT
<213> ORGANISM: Artificial Sequence
<220> FEATURE:
<223> OTHER INFORMATION: IFG-g HCDR3
```

```
<400> SEQUENCE: 39

Asp Gly Ser Ser Gly Trp Tyr Val Pro His Trp Phe Asp Pro
1               5                   10

<210> SEQ ID NO 40
<211> LENGTH: 13
<212> TYPE: PRT
<213> ORGANISM: Artificial Sequence
<220> FEATURE:
<223> OTHER INFORMATION: IFG-g LCDR1

<400> SEQUENCE: 40

Thr Arg Ser Ser Gly Ser Ile Ala Ser Asn Tyr Val Gln
1               5                   10

<210> SEQ ID NO 41
<211> LENGTH: 7
<212> TYPE: PRT
<213> ORGANISM: Artificial Sequence
<220> FEATURE:
<223> OTHER INFORMATION: IFG-g LCDR2

<400> SEQUENCE: 41

Glu Asp Asn Gln Arg Pro Ser
1               5

<210> SEQ ID NO 42
<211> LENGTH: 10
<212> TYPE: PRT
<213> ORGANISM: Artificial Sequence
<220> FEATURE:
<223> OTHER INFORMATION: IFG-g LCDR3

<400> SEQUENCE: 42

Gln Ser Tyr Asp Gly Ser Asn Arg Trp Met
1               5                   10

<210> SEQ ID NO 43
<211> LENGTH: 13
<212> TYPE: PRT
<213> ORGANISM: Artificial Sequence
<220> FEATURE:
<223> OTHER INFORMATION: IL-21 HCDR1

<400> SEQUENCE: 43

Lys Ala Ser Gly Tyr Thr Phe Thr Asp Tyr Trp Met His
1               5                   10

<210> SEQ ID NO 44
<211> LENGTH: 17
<212> TYPE: PRT
<213> ORGANISM: Artificial Sequence
<220> FEATURE:
<223> OTHER INFORMATION: IL-21 HCDR2

<400> SEQUENCE: 44

Leu Ile Asp Thr Ser Asp Val Tyr Thr Ile Tyr Asn Gln Lys Phe Lys
1               5                   10                  15

Gly

<210> SEQ ID NO 45
<211> LENGTH: 10
<212> TYPE: PRT
<213> ORGANISM: Artificial Sequence
<220> FEATURE:
<223> OTHER INFORMATION: IL-21 HCDR3
```

```
<400> SEQUENCE: 45

Ala Arg Tyr Gly Pro Leu Ala Met Asp Tyr
1               5                   10

<210> SEQ ID NO 46
<211> LENGTH: 11
<212> TYPE: PRT
<213> ORGANISM: Artificial Sequence
<220> FEATURE:
<223> OTHER INFORMATION: IL-21 LCDR1

<400> SEQUENCE: 46

Arg Ala Ser Gln Asp Ile Ser Asn Tyr Leu Asn
1               5                   10

<210> SEQ ID NO 47
<211> LENGTH: 8
<212> TYPE: PRT
<213> ORGANISM: Artificial Sequence
<220> FEATURE:
<223> OTHER INFORMATION: IL-21 LCDR2

<400> SEQUENCE: 47

Tyr Tyr Thr Ser Arg Leu His Ser
1               5

<210> SEQ ID NO 48
<211> LENGTH: 8
<212> TYPE: PRT
<213> ORGANISM: Artificial Sequence
<220> FEATURE:
<223> OTHER INFORMATION: IL-21 LCDR3

<400> SEQUENCE: 48

Gln Gln Phe His Thr Leu Arg Thr
1               5

<210> SEQ ID NO 49
<211> LENGTH: 5
<212> TYPE: PRT
<213> ORGANISM: Artificial Sequence
<220> FEATURE:
<223> OTHER INFORMATION: CXCR3 HCDR1

<400> SEQUENCE: 49

Asn Tyr Met Ala Ser
1               5

<210> SEQ ID NO 50
<211> LENGTH: 17
<212> TYPE: PRT
<213> ORGANISM: Artificial Sequence
<220> FEATURE:
<223> OTHER INFORMATION: CXCR3 HCDR2

<400> SEQUENCE: 50

Thr Ile Ser Ser Gly Gly Gly Tyr Thr Tyr Tyr Pro Asp Ser Leu Lys
1               5                   10                  15

Gly

<210> SEQ ID NO 51
<211> LENGTH: 16
<212> TYPE: PRT
<213> ORGANISM: Artificial Sequence
<220> FEATURE:
```

<223> OTHER INFORMATION: CXCR3 HCDR3

<400> SEQUENCE: 51

His Gly Ala Pro Met Thr Thr Val Ile Thr Tyr Ala Pro Tyr Tyr Phe
1               5                   10                  15

<210> SEQ ID NO 52
<211> LENGTH: 10
<212> TYPE: PRT
<213> ORGANISM: Artificial Sequence
<220> FEATURE:
<223> OTHER INFORMATION: CXCR3 LCDR1

<400> SEQUENCE: 52

Arg Ala Ser Ser Ser Val Lys Tyr Met Tyr
1               5                   10

<210> SEQ ID NO 53
<211> LENGTH: 7
<212> TYPE: PRT
<213> ORGANISM: Artificial Sequence
<220> FEATURE:
<223> OTHER INFORMATION: CXCR3 LCDR2

<400> SEQUENCE: 53

Tyr Thr Ser Asn Leu Ala Pro
1               5

<210> SEQ ID NO 54
<211> LENGTH: 9
<212> TYPE: PRT
<213> ORGANISM: Artificial Sequence
<220> FEATURE:
<223> OTHER INFORMATION: CXCR3 LCDR3

<400> SEQUENCE: 54

Gln Gln Phe Thr Thr Ser Pro Tyr Thr
1               5

<210> SEQ ID NO 55
<211> LENGTH: 12
<212> TYPE: PRT
<213> ORGANISM: Artificial Sequence
<220> FEATURE:
<223> OTHER INFORMATION: CCR6 HCDR1

<400> SEQUENCE: 55

Phe Ile Phe Thr Thr Tyr Tyr Met Ser Trp Val Arg
1               5                   10

<210> SEQ ID NO 56
<211> LENGTH: 15
<212> TYPE: PRT
<213> ORGANISM: Artificial Sequence
<220> FEATURE:
<223> OTHER INFORMATION: CCR6 HCDR2

<400> SEQUENCE: 56

Val Ser Asn Ile Ala Ala Gly Gly Ala Thr Asp Tyr Ala Asp Ser
1               5                   10                  15

<210> SEQ ID NO 57
<211> LENGTH: 19
<212> TYPE: PRT
<213> ORGANISM: Artificial Sequence
<220> FEATURE:
<223> OTHER INFORMATION: CCR6 HCDR3

```
<400> SEQUENCE: 57

Cys Ala Arg Gly Pro Trp Gly Arg Tyr His Pro Met Gly Phe Asp Tyr
1               5                   10                  15

Trp Gly Gln

<210> SEQ ID NO 58
<211> LENGTH: 12
<212> TYPE: PRT
<213> ORGANISM: Artificial Sequence
<220> FEATURE:
<223> OTHER INFORMATION: CCR6 LCDR1

<400> SEQUENCE: 58

Arg Ala Ser Gln Ser Val Ser Ser Ser Tyr Leu Ala
1               5                   10

<210> SEQ ID NO 59
<211> LENGTH: 7
<212> TYPE: PRT
<213> ORGANISM: Artificial Sequence
<220> FEATURE:
<223> OTHER INFORMATION: CCR6 LCDR2

<400> SEQUENCE: 59

Gly Ala Ser Ser Arg Ala Thr
1               5

<210> SEQ ID NO 60
<211> LENGTH: 13
<212> TYPE: PRT
<213> ORGANISM: Artificial Sequence
<220> FEATURE:
<223> OTHER INFORMATION: CCR6 LCDR3

<400> SEQUENCE: 60

Cys Gln Gln Ala Tyr Tyr Ser Pro Val Thr Phe Gly Gln
1               5                   10

<210> SEQ ID NO 61
<211> LENGTH: 9
<212> TYPE: PRT
<213> ORGANISM: Artificial Sequence
<220> FEATURE:
<223> OTHER INFORMATION: CD152 HCDR1

<400> SEQUENCE: 61

Phe Ser Leu Ser Asp Tyr Gly Val His
1               5

<210> SEQ ID NO 62
<211> LENGTH: 16
<212> TYPE: PRT
<213> ORGANISM: Artificial Sequence
<220> FEATURE:
<223> OTHER INFORMATION: CD152 HCDR2

<400> SEQUENCE: 62

Val Ile Trp Ala Gly Gly Gly Thr Asn Tyr Asn Ser Ala Leu Met Ser
1               5                   10                  15

<210> SEQ ID NO 63
<211> LENGTH: 7
<212> TYPE: PRT
<213> ORGANISM: Artificial Sequence
<220> FEATURE:
```

```
<223> OTHER INFORMATION: CD152 HCDR3

<400> SEQUENCE: 63

Gly Tyr Ser Ser Thr Ser Phe
1               5

<210> SEQ ID NO 64
<211> LENGTH: 13
<212> TYPE: PRT
<213> ORGANISM: Artificial Sequence
<220> FEATURE:
<223> OTHER INFORMATION: CD152 LCDR1

<400> SEQUENCE: 64

Arg Ala Ser Glu Ser Val Glu Tyr Tyr Val Thr Ser Leu
1               5                   10

<210> SEQ ID NO 65
<211> LENGTH: 7
<212> TYPE: PRT
<213> ORGANISM: Artificial Sequence
<220> FEATURE:
<223> OTHER INFORMATION: CD152 LCDR2

<400> SEQUENCE: 65

Ala Ala Ser Asn Val Glu Ser
1               5

<210> SEQ ID NO 66
<211> LENGTH: 8
<212> TYPE: PRT
<213> ORGANISM: Artificial Sequence
<220> FEATURE:
<223> OTHER INFORMATION: CD152 LCDR3

<400> SEQUENCE: 66

Gln Gln Ser Arg Lys Val Pro Tyr
1               5

<210> SEQ ID NO 67
<211> LENGTH: 10
<212> TYPE: PRT
<213> ORGANISM: Artificial Sequence
<220> FEATURE:
<223> OTHER INFORMATION: PD1 HCDR1

<400> SEQUENCE: 67

Gly Tyr Thr Phe Thr Thr Tyr Tyr Leu Tyr
1               5                   10

<210> SEQ ID NO 68
<211> LENGTH: 15
<212> TYPE: PRT
<213> ORGANISM: Artificial Sequence
<220> FEATURE:
<223> OTHER INFORMATION: PD1 HCDR2

<400> SEQUENCE: 68

Gly Ile Asn Pro Ser Asn Gly Gly Thr Asn Phe Asn Glu Lys Phe
1               5                   10                  15

<210> SEQ ID NO 69
<211> LENGTH: 8
<212> TYPE: PRT
<213> ORGANISM: Artificial Sequence
<220> FEATURE:
<223> OTHER INFORMATION: PD1 HCDR3
```

<400> SEQUENCE: 69

Arg Asp Tyr Arg Tyr Asp Arg Gly
1               5

<210> SEQ ID NO 70
<211> LENGTH: 15
<212> TYPE: PRT
<213> ORGANISM: Artificial Sequence
<220> FEATURE:
<223> OTHER INFORMATION: PD1 LCDR1

<400> SEQUENCE: 70

Arg Ala Ser Lys Ser Val Ser Thr Ser Gly Phe Asn Tyr Ile His
1               5                   10                  15

<210> SEQ ID NO 71
<211> LENGTH: 7
<212> TYPE: PRT
<213> ORGANISM: Artificial Sequence
<220> FEATURE:
<223> OTHER INFORMATION: PD1 LCDR2

<400> SEQUENCE: 71

Leu Ala Ser Asn Leu Glu Ser
1               5

<210> SEQ ID NO 72
<211> LENGTH: 9
<212> TYPE: PRT
<213> ORGANISM: Artificial Sequence
<220> FEATURE:
<223> OTHER INFORMATION: PD1 LCDR3

<400> SEQUENCE: 72

Gln His Ser Arg Glu Leu Pro Leu Thr
1               5

<210> SEQ ID NO 73
<211> LENGTH: 20
<212> TYPE: DNA
<213> ORGANISM: Artificial Sequence
<220> FEATURE:
<223> OTHER INFORMATION: FYN forward primer

<400> SEQUENCE: 73
gccgcctagt agttccctgt                                          20

<210> SEQ ID NO 74
<211> LENGTH: 20
<212> TYPE: DNA
<213> ORGANISM: Artificial Sequence
<220> FEATURE:
<223> OTHER INFORMATION: FYN reverse primer

<400> SEQUENCE: 74
cttcatgatc tgcgcttcct                                          20

<210> SEQ ID NO 75
<211> LENGTH: 23
<212> TYPE: DNA
<213> ORGANISM: Artificial Sequence
<220> FEATURE:
<223> OTHER INFORMATION: TRAF1 forward primer

<400> SEQUENCE: 75
cactgccaag tatggttaca agt                                          23

<210> SEQ ID NO 76
<211> LENGTH: 22
<212> TYPE: DNA
<213> ORGANISM: Artificial Sequence
<220> FEATURE:
<223> OTHER INFORMATION: TRAF1 reverse primer

<400> SEQUENCE: 76
ggttgttctg gtcaagtagc at                                           22

<210> SEQ ID NO 77
<211> LENGTH: 18
<212> TYPE: DNA
<213> ORGANISM: Artificial Sequence
<220> FEATURE:
<223> OTHER INFORMATION: TNFRSF9 forward primer

<400> SEQUENCE: 77
tgtaaaacga cggccagt                                                18

<210> SEQ ID NO 78
<211> LENGTH: 18
<212> TYPE: DNA
<213> ORGANISM: Artificial Sequence
<220> FEATURE:
<223> OTHER INFORMATION: TNFRSF9 reverse primer

<400> SEQUENCE: 78
caggaaacag ctatgacc                                                18

<210> SEQ ID NO 79
<211> LENGTH: 20
<212> TYPE: DNA
<213> ORGANISM: Artificial Sequence
<220> FEATURE:
<223> OTHER INFORMATION: IKBKE forward primer

<400> SEQUENCE: 79
cagggcttgg ctacaacgag                                              20

<210> SEQ ID NO 80
<211> LENGTH: 21
<212> TYPE: DNA
<213> ORGANISM: Artificial Sequence
<220> FEATURE:
<223> OTHER INFORMATION: IKBKE reverse primer

<400> SEQUENCE: 80
gatgtccagg aggtcagatg c                                            21

<210> SEQ ID NO 81
<211> LENGTH: 19
<212> TYPE: DNA
<213> ORGANISM: Artificial Sequence
<220> FEATURE:
<223> OTHER INFORMATION: CASP1 forward primer

<400> SEQUENCE: 81
acaaggcacg ggacctatg                                               19

<210> SEQ ID NO 82
<211> LENGTH: 21
<212> TYPE: DNA
<213> ORGANISM: Artificial Sequence

```
<220> FEATURE:
<223> OTHER INFORMATION: CASP1 reverse primer

<400> SEQUENCE: 82
tcccagtcag tcctggaaat g                                                     21
```

METHODS AND KITS FOR EVALUATING CLINICAL OUTCOMES OF AUTOIMMUNE DISEASE

CROSS REFERENCE TO RELATED APPLICATIONS

This application claims the priority to Singapore application No. 10201704905R, filed 14 Jun. 2017, the contents of which are incorporated herein by reference. A sequence listing under 37 CFR 1.821 as an ASCII text file is submitted herewith, the content of which is incorporated by reference in its entirety. The ASCII text file is entitled "pctsg2018050293-seql-000001-en-20180629" with a date of creation of Jun. 1, 2018 and a size of 16,468 bytes.

FIELD

The present invention relates to methods and kits for evaluating clinical outcomes of autoimmune disease, preferably in subjects undergoing therapy for arthritic disease.

BACKGROUND

Autoimmune disease is an abnormal response of an adaptive immune response against substances and tissues normally present in a vertebrate possessing the adaptive immune response. There are estimated to be more than 80 different types of autoimmune disease. Autoimmune disease can often be chronic, debilitating or even life threatening and is among the most poorly understood and poorly recognized of any category of illness. It has been estimated that autoimmune disease is responsible for more than USD 100 billion in direct healthcare cost annually in the US alone. A better understanding of the disease is needed, as well as better, more effective methods of evaluating and/or managing clinical outcomes.

The total costs attributable to arthritis and other rheumatic conditions in the United States in 2003 was approximately $128 billion. Juvenile idiopathic arthritis (JIA) is the most common childhood rheumatic disease with global prevalence of 16-150 per 10,000 individuals. Polyarticular JIA is a subtype of JIA that clinically resembles adult rheumatoid arthritis.

A common treatment for some autoimmune diseases including, arthritis and other rheumatic conditions such as JIA, Crohns disease, inflammatory bowel disease, lupus, psoriasis among others, is biologics disease modifying anti-rheumatic drugs (DMARDs) such as anti-TNFA therapy. TNF inhibitors are a group of drugs that suppress the physiological response to tumour necrosis factor (TNF). Early aggressive treatment with biologics is now advocated particularly in adult rheumatoid arthritis. TNF inhibitors put patients at increased risk of opportunistic infections that may lead to hospitalization or death. Approximately 30% of JIA patients do not respond to anti-TNF biologics therapy, and for those who respond there is no evident measure for which to predict which patients are amenable for drug discontinuation. Concerns regarding medium/long term toxicities and costs, have also driven the clinical need to locate predictors for successful drug discontinuation. There is an apparent need for better predictors to inform clinical management.

With the advent of anti-TNFA biologics therapy in JIA, there is a growing number of patients who achieve clinical remission on medication (A. Taddio, et al. *Expert Rev Clin Immunol* 12, 641-649 (2016)). The lack of definite therapy withdrawal guidelines exposes some patients to unnecessary long term drug effects and financial burden. Clinicians have cited the duration of remission prior to drug withdrawal as the strongest factor in determining withdrawal decision (D. B. Horton, et al. *J Rheumatol* 44, 352-360 (2017)). The common usage of a combination of proxy disease activity markers such as erythrocyte sedimentation rates (ESR) or clinical symptoms (active joints), though useful in routine clinical practise, is inadequate in accessing subclinical inflammation (C. Hinze, et al. *Nat Rev Rheumatol* 11, 290-300 (2015)). Indeed 20% of patients who fulfil American College of Rheumatology (ACR) criteria for clinical remission still exhibit radiographic damage due to subclinical inflammation (A. K. Brown, et al. *Arthritis Rheum* 58, 2958-2967 (2008)). There is a need to development new tools for clinicians to gauge whether patients will achieve clinical remission off medication.

The dearth of mechanistic understanding on why certain autoimmune arthritic patients flare upon drug discontinuation, is an impediment to clinical management on drug withdrawal strategies. Though current anti-TNFA therapy reflect efficacious responses in 70-80% of juvenile idiopathic arthritic patients, maintenance of long term treatment exposes patients to potential adverse drug effects. The lack of clear definite guidelines for drug discontinuation is further complicated by high relapse rates in 50-80% of patients.

There is a paucity of scientific understanding of why arthritic patients who are successfully treated with anti-TNFA biologics therapy, concomitantly displaying no visible clinical symptoms, relapse upon therapy discontinuation. This evidently makes it hard to establish drug withdrawal strategies. The remarkable success in the deployment of biologics DMARDs such as anti-TNFA therapy has seen improvements to clinical score in 70-80% of juvenile idiopathic arthritic (JIA) patients (R. Cimaz, et al., *Autoimmun Rev* 16, 1008-1015 (2017)), with up to 50% of treated patients achieving clinical remission in long term treatment (S. Verazza, et al. *Pediatr Rheumatol Online J* 14, 68 (2016)). This global growth in the number of JIA patients achieving clinical remission on medication, has now place questions on drug withdrawal guidelines in the spot light. While short/medium term treatment is well tolerated by patients, maintenance of long term treatment with anti-TNFA therapy exposes patients to potential drug side effects, with reports of serious adverse events (SAEs) ranging from 2-20 events/100 patients/year and adverse events (AEs) ranging from 50-2500 cases/100 patients/year (A. Taddio, et al. *Expert Rev Clin Immunol* 12, 641-649 (2016)). The need for clear definite guidelines for drug withdrawal in patients who attain clinical remission, is complicated by the fact that 50-80% patients relapse upon therapy discontinuation (K. Baszis, et al. *Arthritis Rheum* 63, 3163-3168 (2011)). This indicates that a substantial proportion of patients who attain clinical remission on medication, continues to experience subclinical inflammation and persistence of disease. Conversely, patients who have truly achieved disease resolution could be spared long term drug effects. Therefore there is a clinical unmet need to address how discontinuation of anti-TNFA therapy can be implemented safely, and a scientific need to understand how disease persistence or resolution occurs.

An object of the invention is to ameliorate some of the above mentioned difficulties.

SUMMARY

It is hypothesized that CD4 T cells are the main mechanistic drivers for disease resurgence and could serve (a) as a discriminatory tool to determine clinical fate, (b) as potential targets for novel therapy.

Accordingly, a first aspect of the invention includes a method of evaluating a clinical outcome of an autoimmune disease in a subject, the method comprises: isolating a T cell population comprising CD3+ CD4+ in a sample obtained from the subject; and testing the T cell population for one or more biomarker comprising CD45RA, TNF-alpha or CXCR5; wherein a presence or absence of the biomarker in the T cell population or a level of the biomarker in the T cell population in relation to a predetermined level indicates the clinical outcome of the autoimmune disease in the subject.

Another aspect of the invention relates to a method of evaluating a clinical outcome of a rheumatic disease in a subject taking a biologic disease modifying anti-rheumatic drug, the method comprises: isolating a T cell population comprising CD3+ CD4+ in a sample obtained from the subject; and testing the memory T cell population for a biomarker comprising TNF-alpha, CD45RA or CXCR5; wherein a presence or absence of the biomarker in the T cell population or a level of the biomarker in the T cell population in relation to a predetermined level indicates the clinical outcome if the subject stops taking the biologic disease modifying anti-rheumatic drug.

Another aspect of the invention comprises a A kit for evaluating a clinical outcome of an immunological disease in a subject, the kit comprising: at least one antibody adapted to target at least one biomarker on a T cell population in a sample obtained from the subject, the at least one biomarker is selected from the group consisting of: CD3, CD4, CD45RA, TNF-alpha, CXCR5, IL-6, IFN-g, IL-21, CXCR3, CCR6, CD152 and PD1; and a predetermined level of the biomarker in the T cell population to use in predicting the clinical outcome of the autoimmune disease in the subject.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

FIG. 6: Supervised gating of total T-regulatory population was performed in flare/inactive ($T_o/T_{end}$) and healthy individuals. (A) Gate strategy for CD3⁺ CD4⁺ CD45RA⁻ CD25$^{hi}$ FoxP3$^{hi}$ Tregs is shown. Manual gating of total Tregs (CD25$^{hi}$ FoxP3$^{hi}$) from (B) flare, inactive ($T_o$) or healthy individuals, (C) flare, inactive ($T_{end}$) or healthy individuals. Manual gating of CD45RA⁻ Tregs (CD25$^{hi}$ FoxP3$^{hi}$) from (D) flare, inactive ($T_o$) or healthy individuals, (E) flare, inactive ($T_{end}$) or healthy individuals. Mann Whitney two tail test, means±S.D., * $p<0.05$, *$p<0.001$, **$p<0.0001$.

FIG. 7: Clustering of CD3+ CD4⁺ T cells from flare and inactive ($T_{end}$) individuals with MarVis. Two statistically significant nodes were higher in the flare ($T_{end}$) versus inactive ($T_{end}$) individuals. (A) Location of nodes 40 and 45 in the t-SNE map, (B) phenotype of the nodes 40 and 45 and (C) box plots depicting frequency of cells in the nodes 40 and 45. We performed manual gating from the FCS files of flare/inactive ($T_{end}$) or healthy individuals to validate clustering results for the following populations, (D) CD45RA⁻ TNFA⁺, (E) CD45RA⁻ TNFA⁺ IL-6⁺, (F) CD45RA⁻ TNFA⁺ CD152⁺, (G) CD45RA⁻ TNFA⁺ PD1*. Mann Whitney two tail test, means±S.D., *$p<0.05$,  $p<0.01$, **$p<0.0001$.

DETAILED DESCRIPTION

Figure 1A:
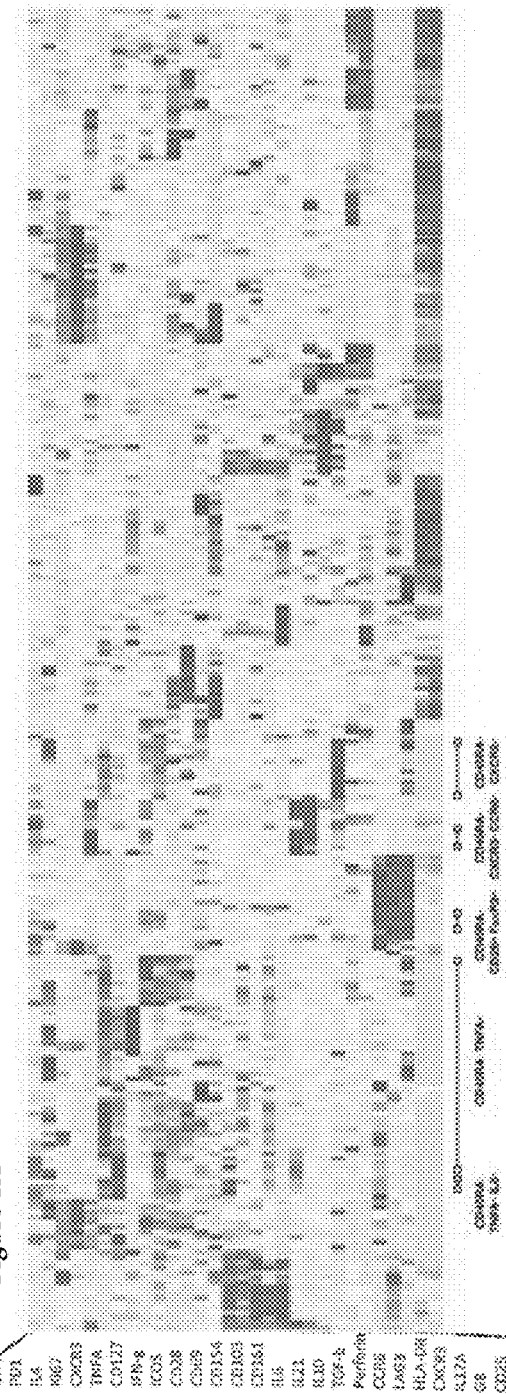
FIG. 1: Clustering of CyToF markers. Unsupervised clustering of normalised $CD3^+$ $CD4^+$ T cells from flare and inactive ($T_o$) individuals was performed with MarVis. Cells are distributed across the t-SNE X-Y scale based on their expression of their 31 functional markers and segregated into distinct nodes. (A) Heatmap depicting hierarchal clustering of nodes with the median expression value of markers, reflecting the spectrum of node phenotypes existing within the CD4 compartment. Certain subsets with $CD45RA^-$ (memory) phenotype are highlighted. (B) Scatter plot of the relative normalised average percentage contribution of cells in each node from flare or inactive ($T_o$) individuals. An enrichment of flare cells in nodes was observed within the 150 to 230 ID range (red dotted box). (C) The nodes (150-230) corresponds to the expression of $CD45RA^-$ $TNFA^+$ (D) Duration of clinical inactivity (months) of patients prior to trial recruitment. (E) Duration of disease activity of patients prior to recruitment in trial. (F) Receiver operating characteristics (ROC) curve constructed with the duration of disease (months) for comparing flare versus inactive ($T_o$) patients prior to therapy withdrawal. Mann Whitney two tail test, means±S.D., *p<0.05.

To uncover the CD4 subset responsible for disease persistence, the Cytometry Time of Flight (CyToF) platform has been leveraged onto immune-phenotype JIA individuals recruited from a clinically controlled trial. The CyToF platform utilises heavy metal conjugated antibodies which avoids the need for spectral compensation. This provides for the opportunity for high dimensional dissection through the complex cellular heterogeneity within the CD4 compartment. In this study, JIA patients who have attain clinical remission with anti-TNFA therapy, were recruited and their clinical progression was prospectively tracked prior to and after drug withdrawal across the trial. the circulatory CD4 subsets were interrogated with CyToF While CD4 T cell involvement in disease pathogenesis has been previously reported, how this contributes to disease resurgence has not been studied. In an attempt to discover clinical predictors for relapse, the heterogenous CD4 compartment was dissected with the high dimensional platform, CyToF, from individuals recruited from a clinically controlled trial. CyToF interrogation of the CD4 T cell compartment from a clinically controlled trial reveal the persistence of a subset of inflammatory memory T cells that is predictive of clinical fate and instrumental to providing mechanistic insights to disease resolution.

Accordingly, a first aspect of the invention includes a method of evaluating a clinical outcome of an autoimmune disease in a subject, the method comprises: isolating a T cell population comprising CD3+ CD4+ in a sample obtained from the subject; and testing the T cell population for one or more biomarker comprising CD45RA, TNF-alpha or CXCR5; wherein a presence or absence of the biomarker in the T cell population or a level of the biomarker in the T cell population in relation to a predetermined level indicates the clinical outcome of the autoimmune disease in the subject.

As used herein the term "autoimmune disease" may refer to any disease that is shown to be based on the existence and/or action of autoreactive cells. Autoimmune disease may include Hashimoto's thyroiditis, Graves' disease, Systemic lupus erythematosus, Sjogren's syndrome, Antiphospholipid syndrome-secondary, Primary biliary cirrhosis, Autoimmune hepatitis, Scleroderma, Rheumatoid arthritis, Antiphospholipid syndrome—primary, Autoimmune thrombocytopenic purpura (ITP), Multiple sclerosis, Myasthenia gravis, juvenile idiopathic arthritis, acute disseminated encephalomyelitis, Addison's disease, Agammaglobulinemia, Alopecia areata, Amyotrophic lateral sclerosis, Ankylosing spondylitis, Autoimmune cardiomyopathy, Autoimmune hemolyticanemia, Autoimmune inner ear disease, Autoimmune lymphoproliferative syndrome, Autoimmune peripheral neuropathy, Autoimmune pancreatitis, Autoimmune progesterone dermatitis, Autoimmune polyendocrine syndrome, Autoimmune thrombocytopenic purpura, Autoimmune urticaria, Autoimmune uveitis, Behcets disease, celiac disease, cold agglutinin disease, Crohn's disease, Dermatomyositis, Diabetes mellitus type I, Eosinophilic fasciitis, Gastrointestinal pemphigoid, Good pastures syndrome, Guillain-Barre syndrome, Hashimoto's encephalopathy, mixed connective tissue disease, Morphea, Nacolepsy, pemphigus vulgaris, polymyositis, primary biliary cirrhosis, relapsing polychondritis, Psoriasis, Psoriatic arthritis, Rheumatic fever, Temporal arteritis, Transverse myelitis, Ulcerative colitis, undifferentiated connective tissue disease, vasculitis, Wegeners granulomatosis or any known or suspected autoimmune disease known in the art.

As used herein the term "subject" refers to any individual or organism with an adaptive immune response system. The subject may include any Gnathostomata or jawed vertebrate, preferably mammals, more preferably humans. In various embodiments the humans arejuveniles aged between 0-15 years old. In various embodiments the subject may potentially be suffering from an autoimmune disease. In various embodiments the subject may have been diagnosed with an autoimmune disease based on signs and symptoms of the subject. In various embodiments the subject may be undergoing treatment for an autoimmune disease.

A T cell population may be isolated by any means known in the art. In various embodiments the T cell population may be isolated from the biological sample using enrichment and/or isolation means known in the art such as antibody filtration, flow cytometry such as fluorescence-activated cell sorting (FACS) or magnetic bead sorting. Alternatively, any enrichment and/or isolation method known in the art would be suitable provided CD4$^+$ T cells expressing CD3$^+$ are identifiable.

As used herein the term "sample" refers to any sample taken from the subject as defined above. Examples of samples may include tissue, whole blood, plasma, Peripheral blood mononuclear cells (PBMCs) synovial fluid, isolated synovial fluid mononuclear cells (SFMCs) or cells from the subject. The samples should be obtained through known ethical procedures to extract and if required isolate the particular biological sample of interest like a T cell population. The samples can be used immediately as fresh samples or they may be stored first. When samples are stored, ideally they remain equivalent to freshly-collected samples. Such storage methods are known in the art. In various embodiments the sample is a body fluid sample, preferably a blood sample. In various embodiments the biological sample includes mononuclear cells such as PBMCs or SFMCs.

As used herein the term "level of the biomarker in the T cell population" is in relation to the number of T cells, as used herein, relates to a detectable increase or decrease compared to a predetermined reference value. In various embodiments the predetermined reference value may be the level identified from T cells isolated from a population of healthy subjects. In various embodiments the predetermined reference value may be the level identified from T cells isolated from a population of subjects that have recovered from an immunological disease. In various embodiments the predetermined reference value may be expressed in terms of a percentage of the total CD3+CD4+ T cell population that include the particular biomarker signature. In various embodiments predetermined level of a biomarker is at least 0.5% of the of the total CD3+CD4+ T cell population. In various embodiments predetermined level of a biomarker is at least 5% of the of the total CD3+CD4+ T cell population. In various embodiments predetermined level of a biomarker is at least 10% of the of the total CD3+CD4+ T cell population. In various embodiments predetermined level of a biomarker is at least 20% of the of the total CD3+CD4+ T cell population. In various embodiments predetermined level of a biomarker is at least 25% of the of the total CD3+CD4+ T cell population. In various embodiments the level of the biomarker in the T cell population is in relation to a ratio of one cell type to another cell type.

As used herein, the term "clinical outcome" may refer to the presence or absence of an autoimmune disease detected by any signs and symptoms known to a person skilled in the art that provides diagnosis of the autoimmune disease. In various embodiments the presence of an autoimmune disease may be referred to as an active autoimmune disease where the subject has any signs and symptoms suitable to provide diagnosis of an autoimmune disease. In various embodiments the absence of an autoimmune disease may be referred to as an inactive autoimmune disease where the subject has no or insufficient signs and symptoms to provides diagnosis of an autoimmune disease. In various embodiments the clinical outcome comprises a flare state, an active state, or an inactive state of the autoimmune disease.

In various embodiments the method further comprises: testing the T cell population for one or more additional biomarker selected from the group consisting of: IL-6, IFN-g, IL-21, CXCR3, CCR6, CD152, PD1, FYN, TNFRSF9 CASP1, TRAF1, and IKBKE.

In various embodiments the method further comprises determining at least one additional biomarker expressed by the CD4$^+$CD3$^+$ T cells, the CD4$^+$ CD3$^+$ CD45RA$^-$TNFA$^+$ T cells, the CD4$^+$CD3$^+$CD45RA$^-$CXCR5+ T cells, the CD4$^+$ CD3$^+$CD45RA$^+$TNFA$^+$ T cells, the CD4$^+$CD3$^+$CD45RA$^+$ CXCR5$^+$ T cells, the CD4$^+$CD3$^+$CD45RA$^-$ T cells, the CD4$^+$CD3$^+$CXCR5$^+$ T cells, or the CD4$^+$CD3$^+$TNFA$^+$ T cells, wherein the at least one additional biomarker optionally being selected from the group consisting of IL-6, IFN-g, IL-21, CXCR3, CCR6, CD152, PD1, FYN, TNFRSF9CASP1, TRAF1, and IKBKE.

In various embodiments the level of the biomarker TNF-alpha in the T cell population above a predetermined level and the absence of CD45RA indicates a likelihood of a flare stateoranactivestate of the autoimmune disease. In various embodiments the CD4$^+$CD3$^+$CD45RA$^-$TNFA$^+$ T cell population above a predetermined level indicates a likelihood of a flare state or an active state of the autoimmune disease. In various embodiments predetermined level of CD4$^+$CD3$^+$ CD45RA$^-$TNFA$^+$ T cells is at least 10% of the of the total CD3+CD4+ T cell population. In various embodiments predetermined level of CD4$^+$CD3$^+$CD45RA$^-$TNFA$^+$ T cells is at least 20% of the of the total CD3+CD4+ T cell population. In various embodiments predetermined level of CD4$^+$CD3$^+$CD45RA$^-$TNFA$^+$ T cells is at least 25% of the of the total CD3+CD4+ T cell population.

In various embodiments the level of the biomarker TNF-alpha in the T cell population below a predetermined level indicates a likelihood of an inactive state of the autoimmune disease. In various embodiments the CD4$^+$CD3$^+$TNFA$^+$ T cell population below a predetermined level indicates a likelihood of an inactive state of the autoimmune disease. In various embodiments predetermined level of CD4$^+$CD3$^+$ TNFA$^+$ T cells is at least 10% of the of the total CD3+CD4+ T cell. In various embodiments predetermined level of CD4$^+$CD3$^+$TNFA$^+$ T cells is at least 20% of the of the total CD3+CD4+ T cell population.

In various embodiments the expression of the one or more biomarker selected from any one of FYN, TNFRSF9 CASP1, TRAF1, IKBKE and a combination thereof, in the T cell population above a predetermined level indicates a likelihood of an inactive state of the autoimmune disease. In various embodiments the mRNA levels of any one of FYN, TNFRSF9 CASP1, TRAF1, IKBKE and a combination thereof, are measured. In various embodiments above the predetermined level of expression is at least 1.5 fold more than a reference level.

In various embodiments the level of the biomarker TNF-alpha in the T cell population above a predetermined level; the absence of CD45RA and the presence of the one or more biomarker IL-6 indicates a likelihood of amplification of the autoimmune disease such as a flare state. In various embodiments the $CD4^+CD3^+CD45RA^-TNFA^+IL-6^+$ T cell population above a predetermined level indicates a likelihood of amplification of the autoimmune disease. In various embodiments predetermined level of $CD4^+CD3^+CD45RA^- TNFA^+ IL-6^+$ T cells is at least 0.5% of the of the total CD3+CD4+ T cell population. In various embodiments the detection of the presence of a subclinical disease subset, $CD3^+CD4^+ CD45RA^-TNFA^+IL-6^{30}\ PD1^-CD152^-$ is indicative that eventually overt flare will manifestation.

In various embodiments the level of the biomarker CXCR5 in the T cell population above a predetermined level and the absence of CD45RA indicates a likelihood of the flare state of the autoimmune disease via memory persistence enhancement through B cell interaction. In various embodiments the $CD4^+CD3^+CD45RA^-CXCR5^+$ T cell population above a predetermined level indicates a likelihood of a flare state or an active state of the autoimmune disease. In various embodiments predetermined level of $CD4^+CD3^+CD45RA^-\ CXCR5^+$ T cell is at least 4% of the of the total CD3+CD4+ T cell population. In various embodiments predetermined level of $CD4^+CD3^+CD45RA^- CXCR5^+$ T cell is at least 5% of the of the total CD3+CD4+ T cell population. In various embodiments predetermined level of $CD4^+CD3^+\ CD45RA^-CXCR5^+$ T cell is at least 6% of the of the total CD3+CD4+ T cell population.

In various embodiments the level of the biomarker CXCR5 in the T cell population above a predetermined level, the absence of CD45RA, and the presence of the one or more additional biomarker CCR6 indicates a likelihood of the active state of the autoimmune disease. In various embodiments the CD4+CD3+CD45RA−CXCR5+ T cells above a predetermined level indicates a likelihood of the active state of the autoimmune disease.

In various embodiments the absence of the one or more biomarker CD152 and/or PD1 in the T cell population further indicates the likelihood of the flare state of the autoimmune disease due to inadequate immune checkpoint control. In various embodiments the $CD4^+CD3^+CD45RA^- TNFA^+\ CD152^-PD1^-$, $CD4^+CD3^+CD45RA^-TNFA^+ CD152^-$, or $CD4^+CD3^+CD45RA^-TNFA^+PD1^-$ in the T cell population indicates the likelihood of the flare state of the autoimmune disease due to inadequate immune checkpoint control. In various embodiments predetermined level of $CD4^+CD3^+CD45RA^-TNFA^+CD152^-PD1^-$, $CD4^+CD3^+ CD45RA^-TNFA^+CD152^-$, or $CD4^+CD3^+CD45RA^-TNFA^+ PD1^-$ T cells is at least 5% of the of the total CD3+CD4+ T cell population. In various embodiments predetermined level of $CD4^+CD3^+CD45RA^-TNFA^+ CD152^-PD1^-$, $CD4^+ CD3^+CD45RA^-TNFA^+CD152^-$, or $CD4^+CD3^+CD45RA^- TNFA^+PD1^-$ T cells is at least 10% of the of the total CD3+CD4+ T cell population. In various embodiments predetermined level of $CD4^+CD3^+CD45RA^-TNFA^+ CD152^-PD1^-$, $CD4^+CD3^+CD45RA^-TNFA^+CD152^-$, or $CD4^+CD3^+CD45RA^-TNFA^+PD1^-$ T cells is at least 20% of the of the total CD3+CD4+ T cell population. In various embodiments the detection of the presence of a subset of inflammatory $CD3^+CD4^+CD45RA^-TNFA^+\ PD1^-CD152^-$ is indicative that active disease may occur.

In various embodiments the autoimmune disease is a rheumatic disease. As used herein the term "rheumatic disease" may refer to connective tissue disorders. In various embodiments rheumatic disease may include Systemic lupus erythematosus, Sjogren's syndrome, Scleroderma, Rheumatoid arthritis, juvenile idiopathic arthritis, Ankylosing spondylitis, Behcets disease, relapsing polychondritis, Psoriatic arthritis, Rheumatic fever, Temporal arteritis, gout, inflammatory arthritis, pseudogout, polymyositis, or any known or suspected connective tissue disorders known in the art.

In various embodiments the rheumatic disease is juvenile idiopathic arthritis (JIA) or rheumatoid arthritis.

In various embodiments the juvenile idiopathic arthritis is polyarticular JIA.

In various embodiments the T cell population is divided into two subsets a first subset comprising CD3+CD4+CD45RA−TNFA+ and a second subset comprising CD3+CD4+CD45RA+TNFA+; determining an amount of the first subset and an amount of the second subset; calculating a ratio of the amount of first subset to the amount of second subset, wherein the ratio in relation to a predetermined ratio indicates the clinical outcome of the autoimmune disease in the subject.

In various embodiments the predetermined ratio is a reference value identified from T cells isolated from a population of healthy subjects. Wherein the T cells isolated from the healthy subjects are divided into two subsets a first healthy subset comprising CD3+CD4+CD45RA−TNFA+ and a second healthy subset comprising CD3+CD4+CD45RA+TNFA+; determining an amount of the first healthy subset and an amount of the second healthy subset; calculating a predetermined ratio of the amount of first healthy subset to the amount of second healthy subset. In various embodiments the predetermined ratio is a reference value identified from T cells a population isolated from subjects that have recovered from an immunological disease. Wherein the T cells isolated from the subjects that have recovered are divided into two subsets a first recovered subset comprising CD3+CD4+CD45RA−TNFA+ and a second recovered subset comprising CD3+CD4+CD45RA+TNFA+; determining an amount of the first recovered subset and an amount of the second recovered subset; calculating a predetermined ratio of the amount of first recovered subset to the amount of second recovered subset.

In this embodiment the inverse relationship of the ratio of $CD45RA^-TNFA^+/CD45RA^+TNFA^+$ subsets has the advantage of allowing for a clear and significant segregation of patients. The ratio, compared to a predetermined ratio calculated from subjects that have recovered from an immunological disease provides very high sensitivity and specificity for evaluating the clinical outcome. Overall the superior outcome of a ratio supports the clinical predictive utility of this persistent pathogenic CD3+CD4+CD45RA−TNFA+ subset in how clinicians can manage clinical decisions.

This study has, with the convergence of a clinically well characterised cohort of patients and application of a high dimensional platform, CyToF, helped explain why patients either persist or resolve their disease during therapy.

Another aspect of the invention relates to a method of evaluating a clinical outcome of a rheumatic disease in a subject taking a biologic disease modifying anti-rheumatic drug, the method comprises: isolating a T cell population comprising CD3+ CD4+ in a sample obtained from the subject; and testing the memory T cell population for a biomarker comprising TNF-alpha, CD45RA or CXCR5; wherein a presence or absence of the biomarker in the T cell population or a level of the biomarker in the T cell population in relation to a predetermined level indicates the clinical outcome if the subject stops taking the biologic disease modifying anti-rheumatic drug.

As used herein the term "rheumatic disease" may refer to connective tissue disorders as defined herein above.

As used herein the term "biologic disease modifying anti-rheumatic drug" or "biologic DMARD" may refer to a therapeutic regimen used for treating, reducing or lessening any rheumatic disease. In various embodiment biologic DMARD may include antibodies such as antibodies to tumor necrosis factor-alpha (TNF-a), antibodies to interleukin 6 (IL-6) or other biologics. Biologics may include medicinal products such as vaccine, blood or blood components, somatic cell therapy, gene therapy, tissue, recombinant proteins, living cells, therapeutic antibodies used to treat rheumatic disease. Antibodies may refer to any monoclonal antibody, polyclonal antibody, bifuctional fusion peptide or any similar constructs that are able to attach to a specific epitope or its receptor and neutralise or stop its activity. Examples of biologics and antibodies used to treat rheumatic disease may include beta interferon, thyroid supplements, blood transfusion, antilogous stem cell transplants, adalimumab, fusion protein of TNF receptor 2 and the protein for IgG1 Fc (Etanercept™) infleximab, certolizumab, golimumab, rituximab, abatacept, anakinra, tocilizumab, muronomab, abciximab, daclizumab, basilimab, omaliizumab, efalizumab, natalizumab, certolizumab pegol, usterkinumab, belimumab, clenoiximab, keliximab, priliximab, teneliximab, vapaliximab, ibalizumab, aselizumab, apolizumab, benralizumab, cedelizumab, eculizumab, epratuzumab, erlizumab, fontolizumab, mepolizumab, ocrelizumab, pascolizumab, pexelizumab, reslizumab, rontalizumab, rovelizumab, rupizumab, siplizumab, talizumab, teplizumab, tocilizumab, toralizumab, vedolizumab, or visillizumab.

In various embodiments the biologic or antibody inhibits TNFa. Examples of antibodies or biologics that inhibit TNFa include adalimumab, fusion protein of TNF receptor 2 and the protein for IgG1 Fc (Etanercept™), infleximab, certolizumab, and golimumab. However, any antibody able to attach to TNFa and inhibit the TNFa binding its receptor is contemplated in these embodiments. In various embodiments the therapeutic regimen comprises administration of methotrexate and/or prednisolone. In various embodiments the therapeutic regimen comprises administration of an antibody that inhibits TNFa and/or methotrexate and/or prednisolone. In various embodiments the biologic DMARD includes an antibody that inhibits TNFa and/or methotrexate.

The benefits of being able to evaluate or determine if a subject that appears to have recovered from a rheumatic disease will continue to remain in remission once the DMARD therapeutic regimen they are taking is withdrawn are great. Only patient or subjects that still require treatment will be a risk of any side effects of taking DMARD's. Patients that are and will remain in remission can be withdrawn from DMARD treatment early. This minimizes side effects of long term drug use in patients that no longer require the DMARD.

In various embodiments a subject appears to have recovered from a rheumatic disease when they are assessed to have no signs or symptoms of the rheumatic disease over three consecutive doctor's visits.

In various embodiments the clinical outcome if the subject stops taking the biologic disease modifying anti-rheumatic drug is within at least 1 year period, or at least 8 months.

In various embodiments the method further comprises, testing the T cell population for one or more biomarker selected from the group consisting of: IL-6, IFN-g, IL-21, CXCR3, CCR6, CD152, PD1, FYN, TNFRSF9 CASP1, TRAF1, and IKBKE.

In various embodiments the clinical outcome comprises a flare state, or an inactive state of the rheumatic disease if the subject stops taking the biologic disease modifying anti-rheumatic drug.

In various embodiments the clinical outcome comprises a flare state if the subject stops taking the biologic disease modifying anti-rheumatic drug in which the subject may encounter a flare up or active signs or symptoms of the rheumatic disease within at least 1 year period, or at least 8 months of stopping taking the biologic disease modifying anti-rheumatic drug. Based on the results of a subject that is likely to have a flare state if the subject stops taking the biologic disease modifying anti-rheumatic drug, a clinician may choose not to withdraw the subject from treatment with the biologic disease modifying anti-rheumatic drug at that time.

In various embodiments the clinical outcome comprises inactive state if the subject stops taking the biologic disease modifying anti-rheumatic drug in which the subject should have no signs or symptoms of the rheumatic disease within at least 1 year period, or at least 8 months of stopping taking the biologic disease modifying anti-rheumatic drug. Subjects evaluated to have a clinical outcome of an inactive state would be considered in remission and a clinician may choose to withdraw the subject from treatment with the biologic disease modifying anti-rheumatic drug.

In various embodiments the level of the biomarker TNF-alpha in the T cell population above a predetermined level and the absence of CD45RA indicates a likelihood of a flare state of the rheumatic disease if the subject stops taking the biologic disease modifying anti-rheumatic drug. In various embodiments the $CD4^+CD3^+CD45RA^-TNFA^+$ T cell population above a predetermined level indicates a likelihood of a flare state of the rheumatic disease if the subject stops taking the biologic disease modifying anti-rheumatic drug.

In various embodiments the level of the biomarker TNF-alpha in the T cell population below a predetermined level indicates a likelihood of an inactive state of the rheumatic disease if the subject stops taking the biologic disease modifying anti-rheumatic drug. In various embodiments the CD4+CD3+CD45RA−TNFA+ T cell population below a predetermined level indicates a likelihood of an inactive state of the rheumatic disease if the subject stops taking the biologic disease modifying anti-rheumatic drug. In which case the subject may be assessed to stop taking the biologic disease modifying anti-rheumatic drug.

In various embodiments the expression of the one or more biomarker selected from any one of FYN, TNFRSF9 CASP1, TRAF1, IKBKE and a combination thereof, above a predetermined level indicates a likelihood of an inactive state of the rheumatic disease if the subject stops taking the biologic disease modifying anti-rheumatic drug. In various embodiments the mRNA levels of any one of FYN, TNFRSF9 CASP1, TRAF1, IKBKE and a combination thereof, are measured and the amount of mRNA above the predetermined level of expression of at least 1.5 fold more than a reference level, indicates a likelihood of an inactive state of the rheumatic disease if the subject stops taking the biologic disease modifying anti-rheumatic drug. In which case the subject may be assessed to stop taking the biologic disease modifying anti-rheumatic drug.

In various embodiments the level of the biomarker CXCR5 in the T cell population above a predetermined level and the absence of CD45RA on the T cell population indicates a likelihood of a flare state of the rheumatic disease via memory persistence enhancement through B cell interaction if the subject stops taking the biologic disease modifying anti-rheumatic drug. In various embodiments the CD4+CD3+CD45RACXCR5+ T cell population above a predetermined level indicates a likelihood of a flare state of the rheumatic disease via memory persistence enhancement through B cell interaction if the subject stops taking the biologic disease modifying anti-rheumatic drug.

In various embodiments the level of the biomarker TNF-alpha on the T cell population above a predetermined level; the absence of CD45RA on the T cell population; and an absence of the one or more biomarker CD152 or PD1 on the T cell population indicates a likelihood of a flare state of the disease due to inadequate immune checkpoint control if the subject stops taking the biologic disease modifying anti-rheumatic drug. In various embodiments the CD4+CD3+CD45RA−TNFA+CD152−PD1−, CD4+CD3+CD45RA−TNFA+CD152−, or CD4+CD3+CD45RA−TNFA+PD1− in the T cell population indicates a likelihood of a flare state of the disease due to inadequate immune checkpoint control if the subject stops taking the biologic disease modifying anti-rheumatic drug.

In various embodiments the biologic disease modifying anti-rheumatic drug is an anti TNF alpha therapy. In various embodiments an anti TNF alpha therapy may include adalimumab, fusion protein of TNF receptor 2 and the protein for IgG1 Fc (Etanercept™) adalimumab, infleximab, certolizumab, or golimumab.

In various embodiments the anti TNF alpha therapy is selected from the group consisting of: a fusion protein of TNF receptor 2 and the protein for IgG1 Fc (Etanercept™) a TNF alpha antibody, adalimumab, and infliximab, optionally in combination methotrexate.

In various embodiments the rheumatic disease is rheumatoid arthritis.

In various embodiments the rheumatic disease isjuvenile idiopathic arthritis (JIA). In various embodiments the juvenile idiopathic arthritis is polyarticular JIA.

In various embodiments the sample is a blood sample, which may include tissue, whole blood, plasma, Peripheral blood mononuclear cells (PBMCs) synovial fluid, isolated synovial fluid mononuclear cells (SFMCs) or cells from the subject, preferably a peripheral blood mononuclear cells (PBMCs) sample. In various embodiments the sample is a peripheral blood mononuclear cells (PBMCs) sample. The sample may be used immediately as fresh samples or they may be stored first. When biological samples are stored, ideally they remain equivalent to freshly-collected sample. Such storage methods are known in the art. In various embodiments the biological sample is a body fluid sample, preferably a blood sample. In various embodiments the biological sample includes mononuclear cells such as PBMCs or SFMCs.

In various embodiments the sample is taken from the subject taking the biologic disease modifying anti-rheumatic drug appearing to have an inactive disease. In various embodiments a subject appears to have an inactive disease or to have recovered from a rheumatic disease when they are assessed to have no signs or symptoms of the rheumatic disease over three consecutive doctor's visits.

In various embodiments the T cell population is divided into two subsets a first subset comprising CD3+CD4+CD45RA−TNFA+ and a second subset comprising CD3+CD4+CD45RA+TNFA+; determining the amount of the first subset and the amount of the second subset; calculating a ratio of the amount of first subset to the amount of second subset, wherein the ratio in relation to a predetermined ratio indicates the clinical outcome of the rheumatic disease in the subject.

In various embodiments the predetermined ratio is a reference value identified from T cells isolated from a population of healthy subjects. Wherein the T cells isolated from the healthy subjects are divided into two subsets a first healthy subset comprising CD3+CD4+CD45RA−TNFA+ and a second healthy subset comprising CD3+CD4+CD45RA+TNFA+; determining an amount of the first healthy subset and an amount of the second healthy subset; calculating a predetermined ratio of the amount of first healthy subset to the amount of second healthy subset. In various embodiments the predetermined ratio is a reference value identified from T cells a population isolated from subjects that have recovered from an immunological disease. Wherein the T cells isolated from the subjects that have recovered are divided into two subsets a first recovered subset comprising CD3+CD4+CD45RA−TNFA+ and a second recovered subset comprising CD3+CD4+CD45RA+TNFA+; determining an amount of the first recovered subset and an amount of the second recovered subset; calculating a predetermined ratio of the amount of first recovered subset to the amount of second recovered subset.

In this embodiment the inverse relationship of the ratio of CD45RA$^-$TNFA$^+$/CD45RA$^+$TNFA$^+$ subsets has the advantage of allowing for a clear and significant segregation of patients. The ratio, compared to a predetermined ratio calculated from subjects that have recovered from an immunological disease provides ver high sensitivity and specificity for evaluating the clinical outcome. Overall the superior outcome of a ratio supports the clinical predictive utility of this persistent pathogenic CD3+CD4+CD45RA−TNFA+ subset in how clinicians can manage DMARD withdrawal decisions.

In various embodiments the methods comprise exposing the sample to at least one antibody adapted to target the biomarker of the T cell population or the one or more additional biomarker. In various embodiments the methods comprise exposing the sample to at least one antibody adapted to target the biomarker of the T cell population or a primer adapted to target the one or more additional biomarker. In various embodiments the methods comprise exposing the sample to at least one antibody adapted to target the biomarker of the T cell population and a primer or antibody adapted to target the one or more additional biomarker.

In various embodiments the at least one antibody is a heavy metal conjugated antibody.

In various embodiments the method comprises utilizing Cytometry by Time-Of-Flight (CyToF) to analyze the sample.

In various embodiments the methods comprise exposing the sample to primers adapted to target the one or more additional biomarker.

In various embodiments the method is an in vitro method.

Profiling of CD4 memory cells mRNA in JIA patients that remain inactive also reveal the presence of several genes that play a role in disease resolution. The persisting CD4 memory subset were used to predict patient's eventual clinical fate prior to therapy withdrawal.

Another aspect of the invention comprises a kit for evaluating a clinical outcome of an immunological disease in a subject, the kit comprising: at least one antibody adapted to target at least one biomarker on a T cell population in a sample obtained from the subject, the at least one biomarker is selected from the group consisting of: CD3, CD4, CD45RA, TNF-alpha, CXCR5, IL-6, IFN-g, IL-21, CXCR3, CCR6, CD152 and PD1; and a predetermined level of the biomarker in the T cell population to use in predicting the clinical outcome of the autoimmune disease in the subject.

In various embodiments the at least one biomarker comprises or consists of CD3, CD4, and CD45RA. In various embodiments the at least one biomarker comprises or consists of CD3, CD4, CD45RA and TNF-alpha. In various embodiments the at least one biomarker comprises or consists of CD3, CD4, CD45RA and CXCR5. In various embodiments the at least one biomarker comprises or consists of CD3, CD4, CD45RA, TNF-alpha and CXCR5. In various embodiments the at least one biomarker comprises or consists of CD3, CD4, CD45RA, TNF-alpha and IL-6. In various embodiments the at least one biomarker comprises or consists of CD3, CD4, CD45RA, TNF-alpha, CD152 and PD1. In various embodiments the at least one biomarker comprises or consists of CD3, CD4, CXCR5 and CCR6. In various embodiments the at least one biomarker comprises or consists of CD3, CD4, CD45RA, TNF-alpha CXCR5, IL-6, IFN-g, IL-21, CXCR3, CCR6, CD152 and PD1.

In various embodiments the CD3 antibody contains a heavy chain variable region and a light chain variable region. Preferably, the heavy chain complementary determining region (CDR) include an amino acid sequence at least 90%, 92%, 95%, 97% 98%, 99% or more identical a sequence selected from the group consisting of GYGMH (SEQ ID NO:1); VIWYDGSKKYYVDSVKG (SEQ ID NO:2); QMGYWHFDL (SEQ ID NO:3). Preferably the light chain CDR include an amino acid sequence at least 90%, 92%, 95%, 97% 98%, 99% or more identical to a sequence selected from the group consisting of the amino acid sequence of RASQSVSSYLA (SEQ ID NO: 4); DASNRAT (SEQ ID NO: 5); QQRSNWPPLT (SEQ ID NO: 6); In various embodiments the CD3 antibody is any known antibody that binds CD3 including commercially available antibodies.

In various embodiments the antibody which is capable of binding to CD4, preferably a human CD4 antigen, contains a heavy chain variable region and a light chain variable region. Preferably, the heavy chain complementary determining region (CDR) include an amino acid sequence at least 90%, 92%, 95%, 97% 98%, 99% or more identical a sequence selected from the group consisting of LASEDIYSDLA (SEQ ID NO:7); NTDTLQN (SEQ ID NO:8); and QQYNNYPWT (SEQ ID NO:9). Preferably the light chain CDR include an amino acid sequence at least 90%, 92%, 95%, 97% 98%, 99% or more identical to a sequence selected from the group consisting of the amino acid sequence of NYGMA (SEQ ID NO:10); TISHDGSDTYFRDSVKG (SEQ ID NO:11); and QGTIAGIRH (SEQ ID NO:12). In various embodiments the CD4 antibody is any known antibody that binds CD4 including commercially available antibodies.

In various embodiments the antibody which is capable of binding to CD45RA, preferably a human CD45RA antigen, contains a heavy chain variable region and a light chain variable region. Preferably, the heavy chain complementary determining region (CDR) include an amino acid sequence at least 90%, 92%, 95%, 97% 98%, 99% or more identical a sequence selected from the group consisting of NYIIH (SEQ ID NO:13); YFNPYNHGTKYNEKFKG (SEQ ID NO:14); and SGPYAWFDT (SEQ ID NO:15). Preferably the light chain CDR include an amino acid sequence at least 90%, 92%, 95%, 97% 98%, 99% or more identical to a sequence selected from the group consisting of the amino acid sequence of RASQNIGTSIQ (SEQ ID NO:16); SSSESIS (SEQ ID NO:17); and QQSNTWPFT (SEQ ID NO:18). In various embodiments the CD45RA antibody is any known antibody that binds CD45RA including commercially available antibodies.

In various embodiments the antibody which is capable of binding to TNF-alpha, preferably a human TNF-alpha antigen, contains a heavy chain variable region and a light chain variable region. Preferably, the heavy chain complementary determining region (CDR) include an amino acid sequence at least 90%, 92%, 95%, 97% 98%, 99% or more identical a sequence selected from the group consisting of NYWMN (SEQ ID NO: 19); EVRLQSDNFTTSHYAESVKG (SEQ ID NO: 20); and PFAY (SEQ ID NO: 21). Preferably the light chain CDR include an amino acid sequence at least 90%, 92%, 95%, 97% 98%, 99% or more identical to a sequence selected from the group consisting of the amino acid sequence of SASSSVSFMY (SEQ ID NO:22); DASILAS (SEQ ID NO:23); and QQWSDYSPRT (SEQ ID NO:24). In various embodiments the TNF-alpha antibody is any known antibody that binds TNF-alpha including commercially available antibodies.

In various embodiments the antibody which is capable of binding to CXCR5, preferably a human CXCR5 antigen, contains a heavy chain variable region and a light chain variable region. Preferably, the heavy chain complementary determining region (CDR) include an amino acid sequence at least 90%, 92%, 95%, 97% 98%, 99% or more identical a sequence selected from the group consisting of GFSLIDYGVN (SEQ ID NO: 25); VIWGDGTTY (SEQ ID NO: 26); and IVY (SEQ ID NO: 27). Preferably the light chain CDR include an amino acid sequence at least 90%, 92%, 95%, 97% 98%, 99% or more identical to a sequence selected from the group consisting of the amino acid sequence of RSSKSLLHSSGKTYLY (SEQ ID NO:28); RISNLAS (SEQ ID NO: 29); and MQHLEYPYT (SEQ ID NO:30). In various embodiments the CXCR5 antibody is any known antibody that binds CXCR5 including commercially available antibodies.

In various embodiments the antibody which is capable of binding to IL-6, preferably a human IL-6 antigen, contains a heavy chain variable region and a light chain variable region. Preferably, the heavy chain complementary determining region (CDR) include an amino acid sequence at least 90%, 92%, 95%, 97% 98%, 99% or more identical a sequence selected from the group consisting of GENFNDYFMN (SEQ ID NO: 31); QMRNKNYQYGTYYAESLEG (SEQ ID NO: 32); and ESYYGFTSY (SEQ ID NO: 33). Preferably the light chain CDR include an amino acid sequence at least 90%, 92%, 95%, 97% 98%, 99% or more identical to a sequence selected from the group consisting of the amino acid sequence of QASQDIGISLS (SEQ ID NO:34); NANNLAD (SEQ ID NO: 35); and QHNSAPYT (SEQ ID NO:36). In various embodiments the IL-6 antibody is any known antibody that binds IL-6 including commercially available antibodies.

In various embodiments the antibody which is capable of binding to IFN-g, preferably a human IFN-g antigen, contains a heavy chain variable region and a light chain variable region. Preferably, the heavy chain complementary determining region (CDR) include an amino acid sequence at least 90%, 92%, 95%, 97% 98%, 99% or more identical a sequence selected from the group consisting of SYAMS (SEQ ID NO: 37); AISGSGGSTYYADSVKG (SEQ ID NO: 38); and DGSSGWYVPHWFDP (SEQ ID NO: 39). Preferably the light chain CDR include an amino acid sequence at least 90%, 92%, 95%, 97% 98%, 99% or more identical to a sequence selected from the group consisting of the amino acid sequence of TRSSGSIASNYVQ (SEQ ID NO:40); EDNQRPS (SEQ ID NO: 41); and QSYDGSNRWM (SEQ ID NO:42). In various embodiments the IFN-g antibody is any known antibody that binds IFN-g including commercially available antibodies.

In various embodiments the antibody which is capable of binding to IL-21, preferably a human IL-21 antigen, contains a heavy chain variable region and a light chain variable region. Preferably, the heavy chain complementary determining region (CDR) include an amino acid sequence at least 90%, 92%, 95%, 97% 98%, 99% or more identical a sequence selected from the group consisting of KASGYTFTDYWMH (SEQ ID NO: 43); LIDTSDVYTIYNQKFKG (SEQ ID NO: 44); and ARYGPLAMDY (SEQ ID NO: 45). Preferably the light chain CDR include an amino acid sequence at least 90%, 92%, 95%, 97% 98%, 99% or more identical to a sequence selected from the group consisting of the amino acid sequence of RASQDISNYLN (SEQ ID NO:46); YYTSRLHS (SEQ ID NO: 47); and QQFHTLRT (SEQ ID NO:48). In various embodiments the IL-21 antibody is any known antibody that binds IL-21 including commercially available antibodies.

In various embodiments the antibody which is capable of binding to CXCR3, preferably a human CXCR3 antigen, contains a heavy chain variable region and a light chain variable region. Preferably, the heavy chain complementary determining region (CDR) include an amino acid sequence at least 90%, 92%, 95%, 97% 98%, 99% or more identical a sequence selected from the group consisting of NYMAS (SEQ ID NO: 49); TISSGGGYTYYPDSLKG (SEQ ID NO: 50); and HGAPMTTVITYAPYYF (SEQ ID NO: 51). Preferably the light chain CDR include an amino acid sequence at least 90%, 92%, 95%, 97% 98%, 99% or more identical to a sequence selected from the group consisting of the amino acid sequence of RASSSVKYMY (SEQ ID NO:52); YTSNLAP (SEQ ID NO: 53); and QQFTTSPYT (SEQ ID NO:54). In various embodiments the CXCR3 antibody is any known antibody that binds CXCR3 including commercially available antibodies.

In various embodiments the antibody which is capable of binding to CCR6, preferably a human CCR6 antigen, contains a heavy chain variable region and a light chain variable region. Preferably, the heavy chain complementary determining region (CDR) include an amino acid sequence at least 90%, 92%, 95%, 97% 98%, 99% or more identical a sequence selected from the group consisting of FIFTTYYMSWVR (SEQ ID NO: 55); VSNIAAGGATDYADS (SEQ ID NO: 56); and CARGPWGRYHPMGFDYWGQ (SEQ ID NO: 57). Preferably the light chain CDR include an amino acid sequence at least 90%, 92%, 95%, 97% 98%, 99% or more identical to a sequence selected from the group consisting of the amino acid sequence of RASQSVSSSYLA (SEQ ID NO:58); GASSRAT (SEQ ID NO: 59); and CQQAYYSPVTFGQ (SEQ ID NO:60). In various embodiments the CCR6 antibody is any known antibody that binds CCR6 including commercially available antibodies.

In various embodiments the antibody which is capable of binding to CD152, preferably a human CD152 antigen, contains a heavy chain variable region and a light chain variable region. Preferably, the heavy chain complementary determining region (CDR) include an amino acid sequence at least 90%, 92%, 95%, 97% 98%, 99% or more identical a sequence selected from the group consisting of FSLSDYGVH (SEQ ID NO: 61); VIWAGGGTNYNSALMS (SEQ ID NO: 62); and GYSSTSF (SEQ ID NO: 63). Preferably the light chain CDR include an amino acid sequence at least 90%, 92%, 95%, 97% 98%, 99% or more identical to a sequence selected from the group consisting of the amino acid sequence of RASESVEYYVTSL (SEQ ID NO:64); AASNVES (SEQ ID NO: 65); and QQSRKVPY (SEQ ID NO:66). In various embodiments the CD152 antibody is any known antibody that binds CD152 including commercially available antibodies.

In various embodiments the antibody which is capable of binding to PD1, preferably a human PD1 antigen, contains a heavy chain variable region and a light chain variable region. Preferably, the heavy chain complementary determining region (CDR) include an amino acid sequence at least 90%, 92%, 95%, 97% 98%, 99% or more identical a sequence selected from the group consisting of GYTFTTYYLY (SEQ ID NO: 67); GINPSNGGTNFNEKF (SEQ ID NO: 68); and RDYRYDRG (SEQ ID NO: 69). Preferably the light chain CDR include an amino acid sequence at least 90%, 92%, 95%, 97% 98%, 99% or more identical to a sequence selected from the group consisting of the amino acid sequence of RASKSVSTSGFNYIH (SEQ ID NO:70); LASNLES (SEQ ID NO:71); and QHSRELPLT (SEQ ID NO:72). In various embodiments the PD1 antibody is any known antibody that binds PD1 including commercially available antibodies.

In various embodiments the at least one antibody is a heavy metal conjugated antibody.

In various embodiments the kit further comprises primers for detecting expression of FYN, TRAF1, TNFRSF9, IKBKE, or CASP1.

In various embodiments the primers for FYN comprise the forward primer GCCGCCTAGTAGTTCCCTGT (SEQ ID NO. 73) and the reverse primer CTTCATGATCTGCGCTTCCT (SEQ ID NO. 74). In various embodiments any primers known in the art for FYN may be suitable.

In various embodiments the primers for TRAF1 comprise the forward primer CACTGCCAAGTATGGTTACAAGT (SEQ ID NO. 75) and the reverse primer GGTTGTTCTGGTCAAGTAGCAT (SEQ ID NO. 76). In various embodiments any primers known in the art for TRAF1 may be suitable.

In various embodiments the primers for TNFRSF9 comprise the forward primer TGTAAAACGACGGCCAGT (SEQ ID NO. 77) and the reverse primer CAGGAAACAGCTATGACC (SEQ ID NO. 78). In various embodiments any primers known in the art for TNFRSF9 may be suitable.

In various embodiments the primers for IKBKE comprise the forward primer CAGGGCTTGGCTACAACGAG (SEQ ID NO. 79) and the reverse primer GATGTCCAGGAGGTCAGATGC (SEQ ID NO. 80). In various embodiments any primers known in the art for IKBKE may be suitable.

In various embodiments the primers for CASP1 comprise the forward primer ACAAGGCACGGGACCTATG (SEQ ID NO. 81) and the reverse primer TCCCAGTCAGTCCTGGAAATG (SEQ ID NO. 82). In various embodiments any primers known in the art for CASP1 may be suitable.

As would be understood by a person skilled in the art, the embodiments may be used in combination with each other embodiment or several embodiments.

Unless defined otherwise, all technical and scientific terms used herein have the same meaning as is commonly understood by a skilled person to which the subject matter herein belongs. As used herein, the following definitions are supplied in order to facilitate the understanding of the present invention.

Throughout this document, unless otherwise indicated to the contrary, the terms "comprising", "consisting of", "having" and the like, are to be construed as non-exhaustive, or in other words, as meaning "including, but not limited to".

Furthermore, throughout the specification, unless the context requires otherwise, the word "include" or variations such as "includes" or "including" will be understood to imply the inclusion of a stated integer or group of integers but not the exclusion of any other integer or group of integers.

As used in the specification and the appended claims, the singular form "a", and "the" include plural references unless the context clearly dictates otherwise.

EXAMPLES

Example 1 Polyarticular JIA Patient Cohort and Study Design

A significant proportion of polyarticular JIA patients continue to experience subclinical persistence of disease despite achieving therapeutic clinical control with anti-TNFA biologics. A clinical trial (Determining Predictors of Safe Discontinuation of Anti-TNF Treatment in JIA) was designed with the aim of understanding why certain JIA patients face persistent subclinical disease and eventually relapsing upon therapy withdrawal. JIA patients treated with anti-TNF biologics (etanercept, adalimumab or infliximab) were recruited into the trial if they were proven to have inactive disease across a period of 6 months with at least 3 proven consecutive visits of clinical inactivity (Wallace criteria) and were subsequently withdrawn from therapy for a duration of 8 months (Table 1).

TABLE 1

Demographics and medication course history for the JIA patients and healthy controls. JIA patients are placed on anti-TNFA medication (etanercept, adalimumab or infliximab) with/without concurrent methotrexate combination, for at least 6 months, and proven to be in inactive disease (Wallace criteria), and subjected to anti-TNFA withdrawal. They are either scored to be flare or inactive. Healthy non-disease controls with no inflammatory diseases were recruited from day surgeries.

Demographics and medication course

| Variable | | Flare (n = 24) | Inactive (n = 24) | Healthy (n = 17) |
|---|---|---|---|---|
| Anti-TNFA Biologics | etanercept (%) | 19 (79.2%) | 22 (91.7%) | Nil |
| | adalimumab (%) | 3 (12.5%) | 2 (8.3%) | Nil |
| | Infliximab (%) | 2 (8.3%) | 0 (0%) | Nil |
| Methotrexate (concurrent)(%) | | 7 (29.2%) | 11 (45.8%) | Nil |
| Rheumatoid Factor + | | 0 (0%) | 7 (29.2%) | Nil |
| Average age (yrs) ± Std Dev | | 13.1 ± 4.8 | 10.4 ± 3.9 | 7.4 ± 2.4 |
| Gender Female:Male Ratio | | 7:1 | 3:1 | 4:13 |

Study Design

The aim of the study is to determine why certain JIA patients relapse upon therapy withdrawal despite achieving previous therapeutic control. PBMC samples were used from 48 randomly selected polyarticular JIA patients recruited in the trial "Determining Predictors of Safe Discontinuation of Anti-TNF treatment in JIA" (ID: NCT00792233). The study was approved through the Institutional Review Board, requiring fulfilment of either informed consent/assent forms from all participants. Patients were treated with anti-TNFA biologics and determined to have inactive disease across 6 months (verified by 3 consecutive visits). Disease inactivity is as defined by Wallace criteria; (a) absence of active joints, (b) lack of fever, rash, serositis attributable to JIA, (c) no active uveitis, (d) within normal range of ESR unless attributable to JIA, (e) physician global disease activity of ≤0.5 Likert-like scale and (f) duration of morning stiffness ≤15 minutes. With proven disease inactivity, patients were recruited into the trial and subsequently withdrawn from therapy (start of withdrawal defined as $T_o$) for a duration of 8 months (end of withdrawal defined as $T_{end}$). PBMCs are obtained from the patients prior to therapy withdrawal ($T_o$) and after therapy withdrawal ($T_{end}$). Patients at the end of the trial were designated as either flare (n=24) or inactive (n=24) individuals depending on 6 core JIA parameters; (a) number of active joints, (b) number of joints with loss of motion, (c) medical doctor global assessment of current disease activity (Likert-like scale), (d) patient/parent global assessment of overall disease severity in prior week (Likert-like scale), (e) a validated measure of physical function (CHAQ) and (f) ESR. A patient was deemed as flare if the subject patient demonstrates at least a 30% worsening in ≥3 of the 6 JIA core parameters with no more than 1 improving by >30%. For the age-matched healthy controls, PBMCs from the Precision Rheumatology International Platform (PRIP) study in KK Women's and children Hospital were used. A cohort of 17 healthy (non-JIA) paediatric controls with no indication of inflammation, were recruited with informed consent/assent, pre-operatively (during intravenous plug setting) from patients scheduled for day surgeries. PBMCs from 4 paired JIA patients were used, all recruited with informed consent/assent through the study "A precision medicine approach to understand and predict responsiveness to therapy in human arthritis" in KK Women's and children Hospital. These active JIA patients are initially treatment naive (pre) to anti-TNFA biologics and after a duration of 6 months with anti-TNFA biologics reflect recent susceptibility to treatment with the complete absence of active joints (post).

Isolation and Cryopreservation of PBMCs

Blood was drawn into EDTA tubes to prevent coagulation, transported at room temperature and processed within 24 hrs. PBMCs were isolated via density gradient centrifugation with Histopaque-1077 (Sigma-aldrich) or Ficoll (GE Healthcare) under manufacturer's instructions. The cells are resuspended in 90% v/v FBS, 10% v/v DMSO and frozen in liquid nitrogen for long term storage.

Circulatory immune cells (PBMCs) were obtained from the patients at the start of withdrawal ($T_o$) and after withdrawal of therapy at the end of the trial ($T_{end}$). 48 polyarticular JIA patients were scored and categorised into their clinical fate (Table 2) either as flare (n=24) or inactive (n=24) depending on six core disease parameters; (a) number of joints with active arthritis, (b) loss of motion, (c) medical doctor global assessment of current disease activity, (d) patient/parent global assessment of overall disease severity in prior week, (e) a validated measure of physical function and (f) ESR.

TABLE 2

Scoring matrix of JIA patients used for classification into flare and inactive.

| Questions qualifying for remaining in inactive disease | | | | | | Score for flare | | | | | | |
|---|---|---|---|---|---|---|---|---|---|---|---|---|
| Any joints with active arthritis | Any fever, rash, serositis, splenomegaly or generalized lymph-adenopathy attributable to JIA? | Any active uveitis? | Abnormal ESR attributable to JIA using site normal ranges? | Morning stiffness more than 15 minutes? | MD global assessment of disease activity more than 0.5 on a Likert-like scale? | The subject has 'Inactive Disease'? | MD global flare | LOM joints flare | Active joint flare | Parent global flare | CHAQ flare | ESR flare | The subject meets criteria for flare? |
| Yes | No | No | No | Yes | Yes | No | 1 | 4 | 6 | 2 | 0.25 | normal | Yes |
| Yes | No | No | Yes | Yes | Yes | No | 4 | 13 | 15 | 0.5 | 0.25 | abnormal | Yes |
| Yes | No | No | Yes | No | Yes | No | 2.5 | 3 | 2 | 0 | 0 | abnormal | Yes |
| Yes | No | No | Yes | Yes | Yes | No | 3.5 | 6 | 9 | 5.5 | 0 | normal | Yes |
| No | No | No | No | No | No | Yes | N.A | N.A | N.A | N.A | N.A | N.A | N.A |
| No | No | No | No | No | No | Yes | N.A | N.A | N.A | N.A | N.A | N.A | N.A |
| No | No | No | Yes | Yes | Yes | No | 1 | 4 | 0 | 3.5 | 0.375 | abnormal | Yes |
| No | No | No | Yes | Yes | Yes | No | 1 | 4 | 0 | 3.5 | 0.375 | abnormal | Yes |
| No | No | No | No | No | No | Yes | N.A | N.A | N.A | N.A | N.A | N.A | N.A |
| Yes | No | No | No | Yes | Yes | No | 3 | 0 | 2 | 2 | 0 | normal | Yes |
| No | No | No | No | No | No | Yes | N.A | N.A | N.A | N.A | N.A | N.A | N.A |
| Yes | No | No | No | Yes | Yes | No | 6.5 | 4 | 7 | 5 | 0.5 | normal | Yes |
| No | No | No | No | No | No | Yes | N.A | N.A | N.A | N.A | N.A | N.A | N.A |
| Yes | No | No | Yes | No | Yes | No | 3.5 | 4 | 3 | 2 | 0.25 | abnormal | Yes |
| Yes | No | No | Yes | Yes | Yes | No | 3.5 | 1 | 3 | 1 | 0.25 | Abnormal | Yes |
| No | No | No | No | No | No | Yes | N.A | N.A | N.A | N.A | N.A | N.A | N.A |
| No | No | No | No | No | No | Yes | N.A | N.A | N.A | N.A | N.A | N.A | N.A |
| No | No | No | No | No | No | Yes | N.A | N.A | N.A | N.A | N.A | N.A | N.A |
| Yes | No | No | Yes | Yes | Yes | No | 9 | 24 | 28 | 2 | 0.125 | abnormal | Yes |
| No | No | No | No | No | No | Yes | N.A | N.A | N.A | N.A | N.A | N.A | N.A |
| No | No | Yes | No | No | Yes | No | uveitis | — | — | — | — | — | Yes |
| No | No | No | No | No | No | Yes | N.A | N.A | N.A | N.A | N.A | N.A | N.A |
| No | No | No | No | No | No | Yes | N.A | N.A | N.A | N.A | N.A | N.A | N.A |
| Yes | No | No | Yes | Yes | Yes | No | 2 | 2 | 2 | 6.5 | 0 | normal | Yes |
| No | No | Yes | No | No | Yes | No | uveitis | — | — | — | — | — | Yes |
| Yes | No | No | Yes | Yes | Yes | No | 3 | 2 | 3 | 0 | 0 | abnormal | Yes |
| No | No | No | No | No | No | Yes | N.A | N.A | N.A | N.A | N.A | N.A | N.A |
| Yes | No | No | No | No | Yes | No | 5 | 0 | 1 | 7 | 0.75 | — | Yes |
| No | No | No | No | No | No | Yes | N.A | N.A | N.A | N.A | N.A | N.A | N.A |
| Yes | No | No | Yes | Yes | Yes | No | 3 | 2 | 2 | 2 | 0 | abnormal | Yes |
| No | No | No | No | No | No | Yes | N.A | N.A | N.A | N.A | N.A | N.A | N.A |
| Yes | No | No | No | Yes | Yes | No | 2 | 2 | 2 | 6 | 0 | normal | Yes |
| No | No | No | No | No | No | Yes | N.A | N.A | N.A | N.A | N.A | N.A | N.A |
| No | No | No | No | No | No | Yes | N.A | N.A | N.A | N.A | N.A | N.A | N.A |
| No | No | No | No | No | No | Yes | N.A | N.A | N.A | N.A | N.A | N.A | N.A |
| Yes | No | No | Yes | Yes | Yes | No | 2 | 4 | 4 | 0 | 0 | abnormal | Yes |
| No | No | No | No | No | No | Yes | N.A | N.A | N.A | N.A | N.A | N.A | N.A |
| No | No | No | No | No | No | Yes | N.A | N.A | N.A | N.A | N.A | N.A | N.A |

Note
that patients are first scored for disease inactivity (Wallace criteria) and if they are exhibiting disease activity, they are subsequently scored for flaring.

Figure 1B:
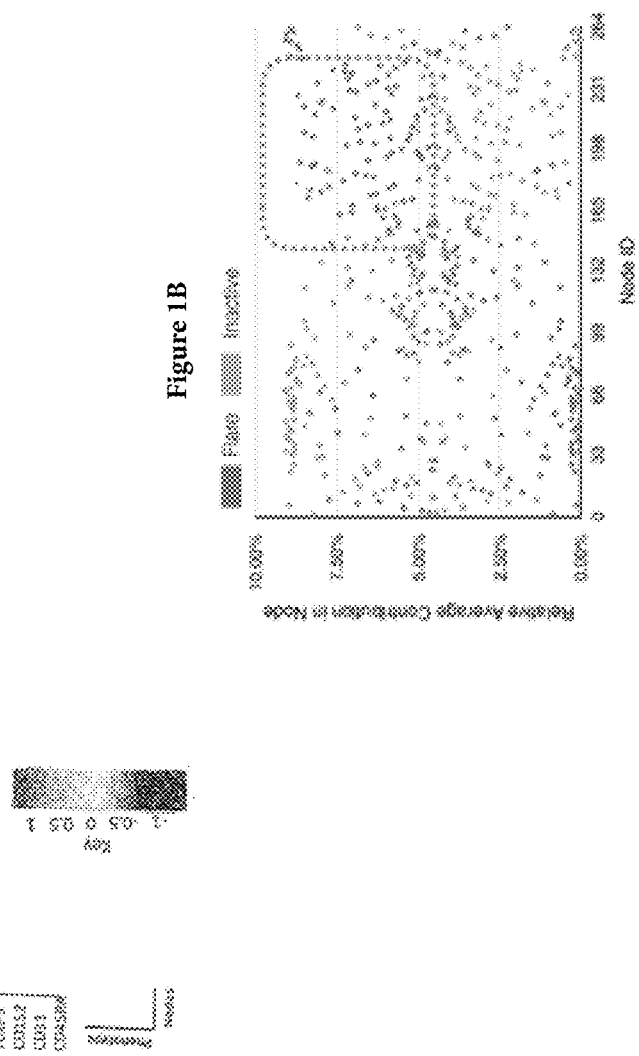
Figure 1D:
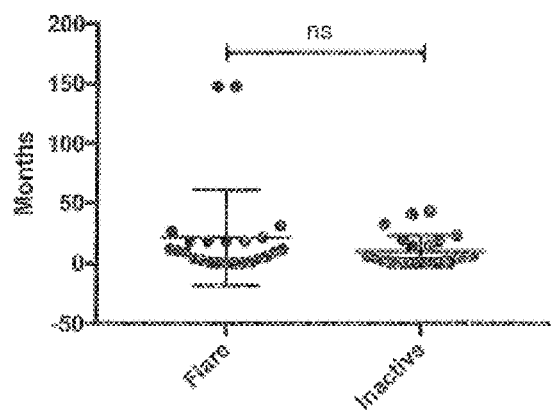
Figure 1E:
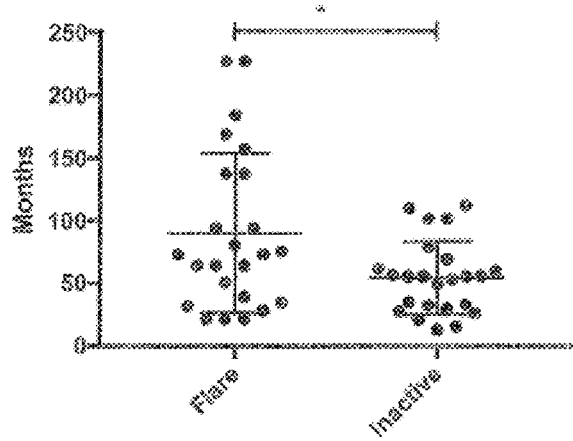
Figure 1F:
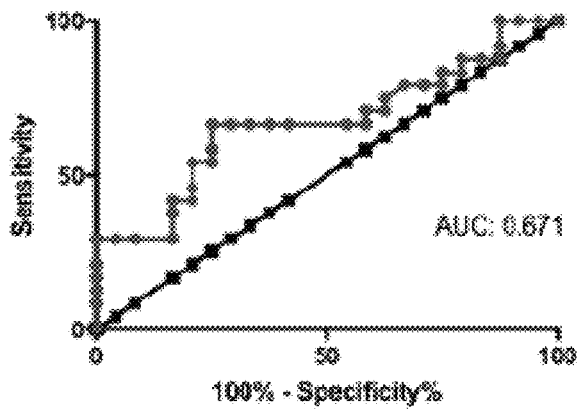

A separate cohort of healthy (non-JIA) paediatric controls (n=17) with no inflammatory disease were also recruited pre-operatively (during intravenous plug setting) from patients scheduled for day surgeries. Flare JIA patients recruited had no significant difference in the number of months (flare=21.4±39.8, inactive=28.6±29.8, p=0.1123) with inactive disease maintenance prior to trial as compared with inactive patients (FIG. 1D), an indication that both categories had similar prior clinical remission control with biologics therapy. As early aggressive treatment with biologics is now advocated particularly in adult rheumatoid arthritis the disease duration of patients prior to treatment (20, 21), so was also examined. Indeed flare patients had longer disease duration (flare=90.3±63.7, inactive=54.4±29.3 months, p<0.05) as compared with inactive patients prior to therapy (FIG. 1E), though this parameter alone fares marginally (AUC=0.671) in predicting for flaring upon therapy withdrawal (FIG. 1F). With the trial in place, the reason a subset of JIA patients fail to resolve their disease despite achieving therapeutic control and eventually flaring upon therapy withdrawal was investigated.

Example 2: Examination of CD4 Compartment

Figure 2A:
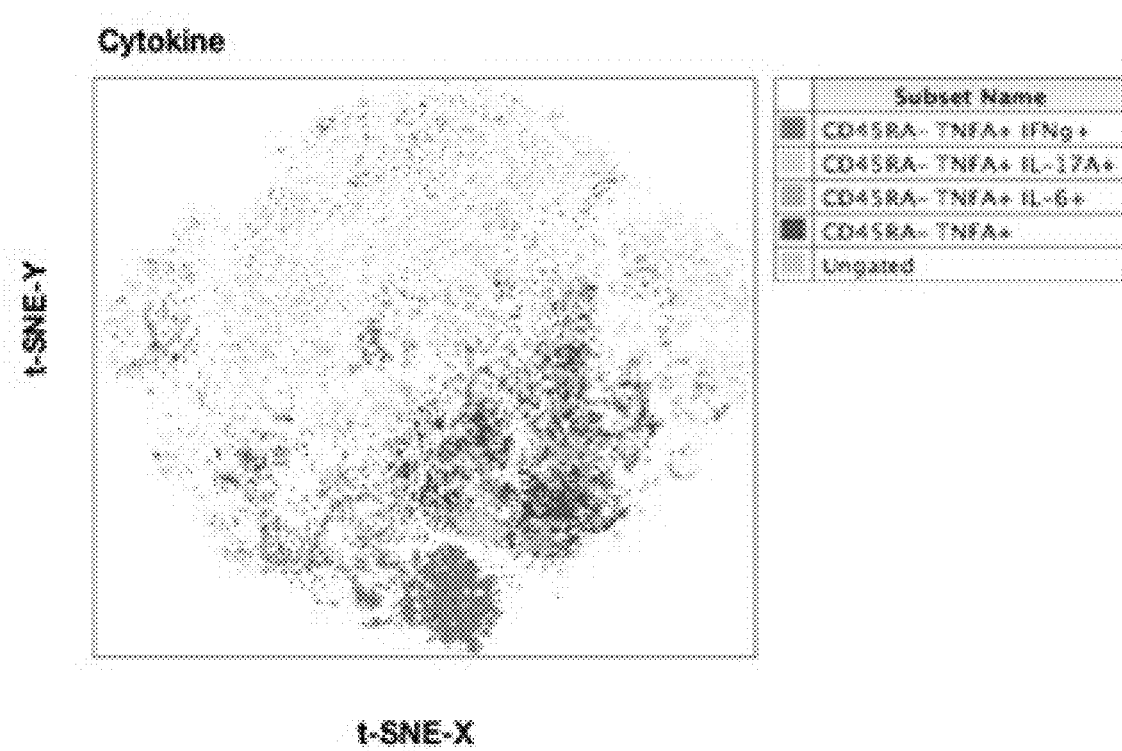
FIG. 2: Distribution of flare and inactive ($T_o$) cells within t-SNE map. The CD45RA− TNFA+ cells were back-gated onto the t-SNE maps. (A) The expression profile for cytokines (TNFA, IL-6, IFNg and IL-17A) and (B) immune checkpoints (PD1 and CD152) distributed across the $CD45RA^-$ $TNFA^+$ region is shown. The patient distribution of (C) flare or (D) inactive ($T_o$) individuals within the $CD45RA^-$ $TNFA^+$ region is shown. (E) PBMCs were gated for $CD45^+$ $CD3^+$ $CD4^+$ $CD8^-$ T cells from raw CyToF FCS files. No significant changes were detected in gross $CD4^+$ populations across cohort. (F) Clustering of total $CD3^+$ $CD4^+$ cells from flare and inactive ($T_o$) individuals. Density expression maps depicting the distribution and expression of cells with the 31 functional markers shown. Mann Whitney two tail test, means S.D., *p<0.05.
Figure 2B:
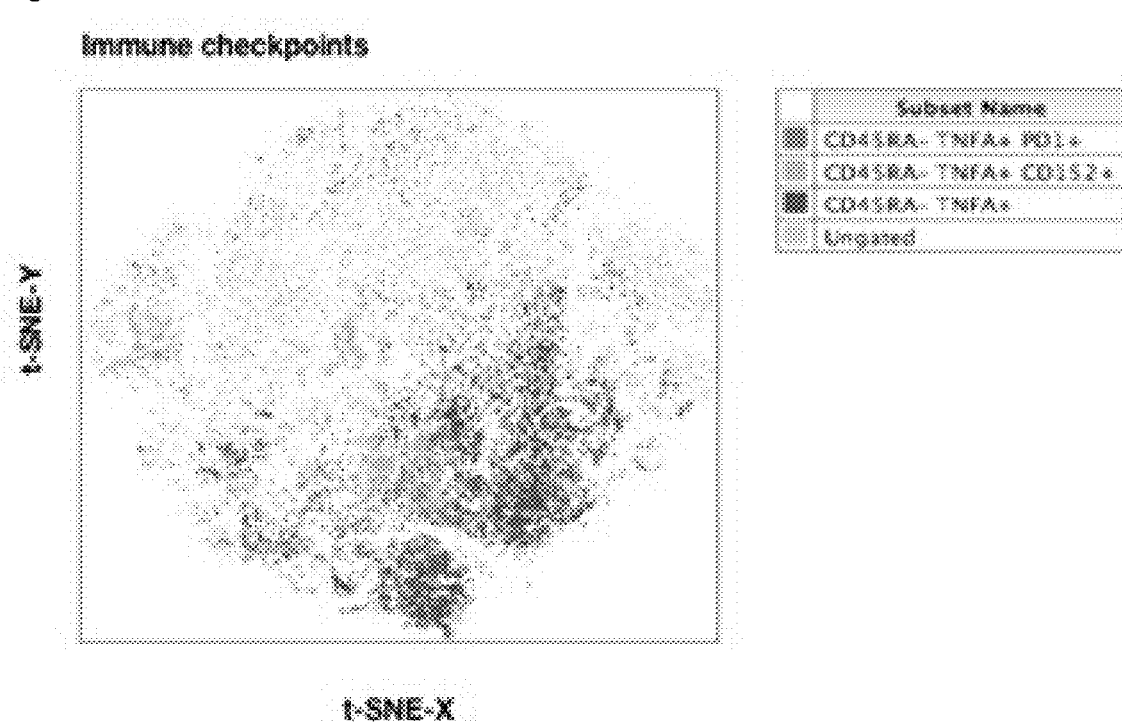
Figure 2C:
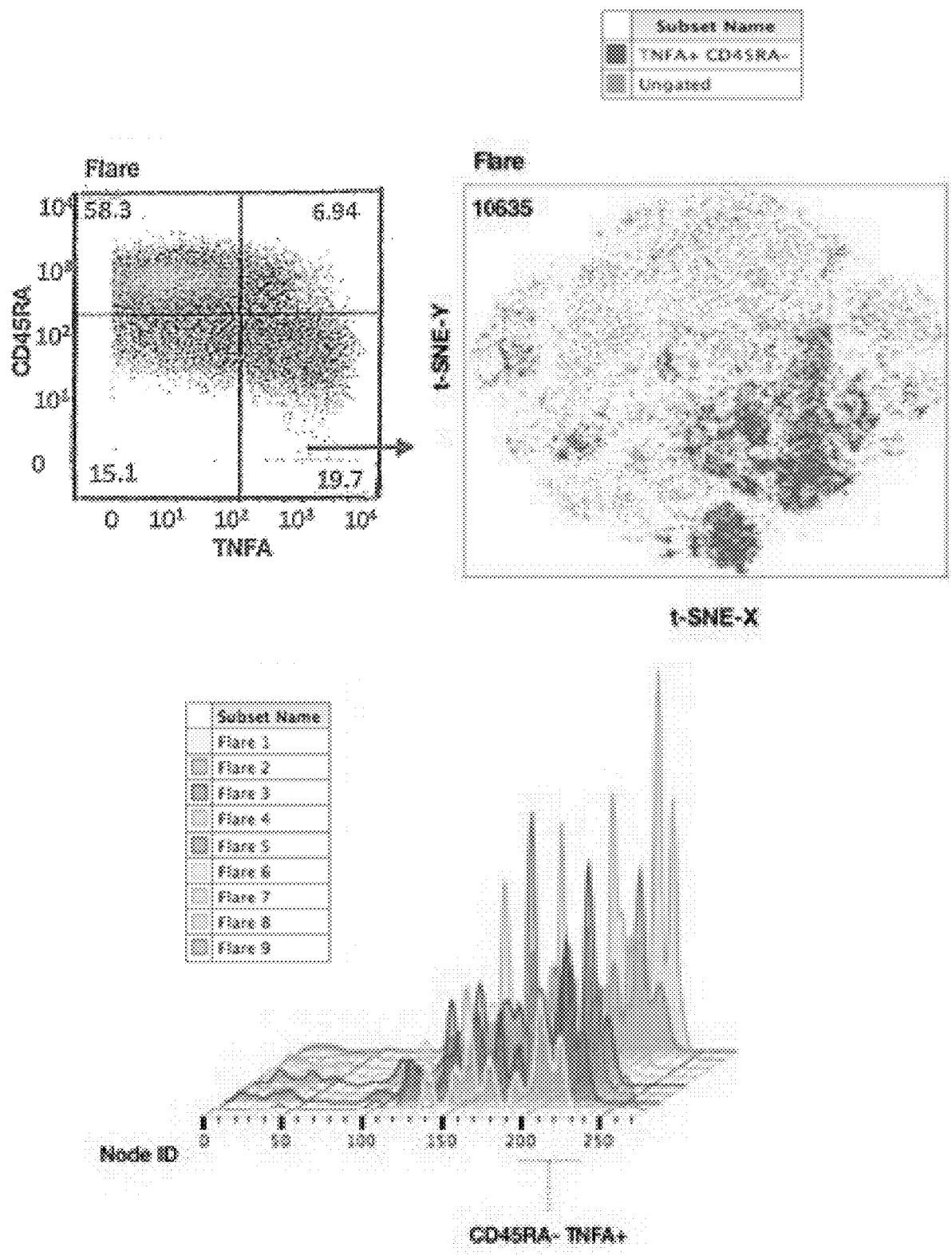
Figure 2D:
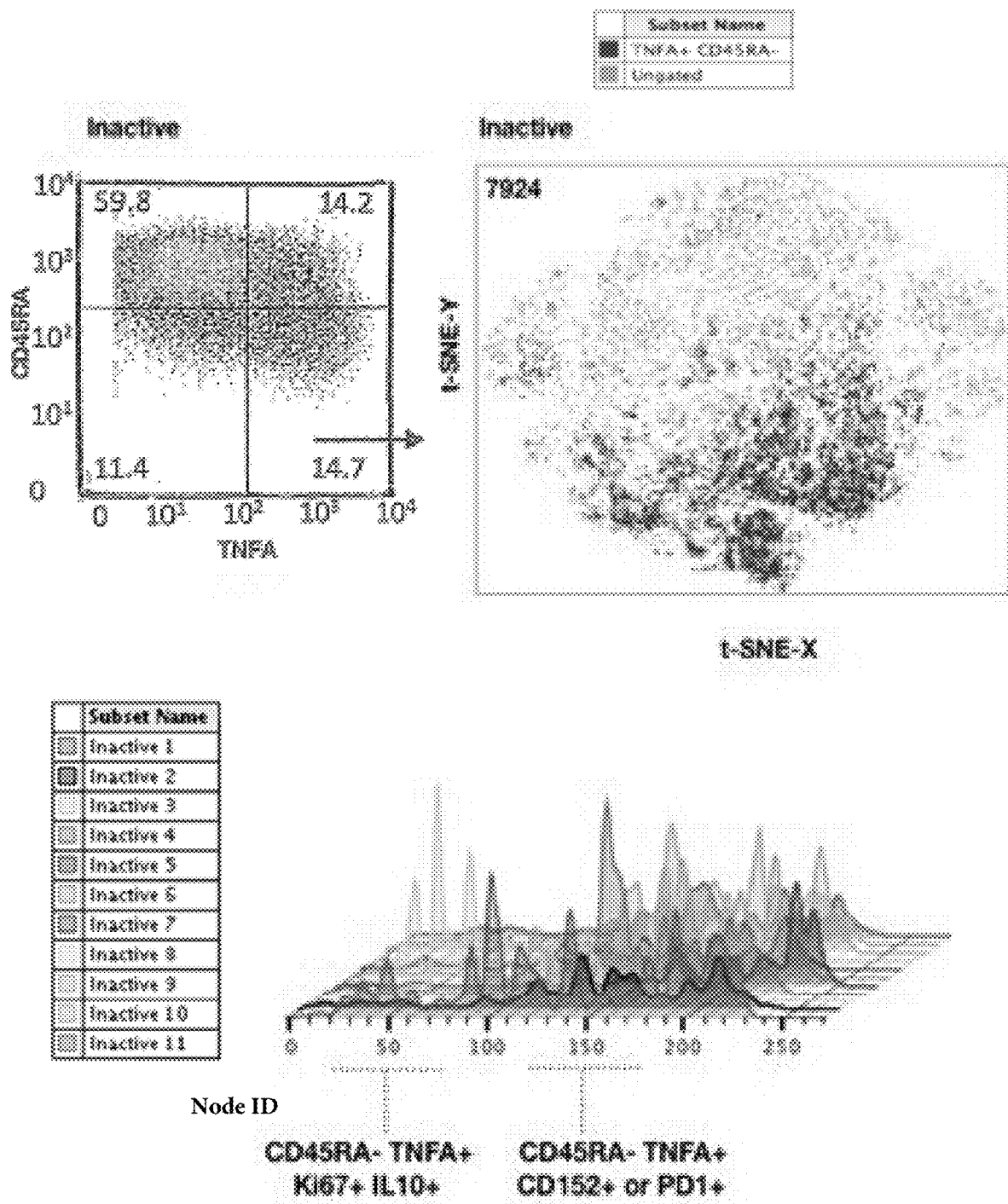
Figure 2E:
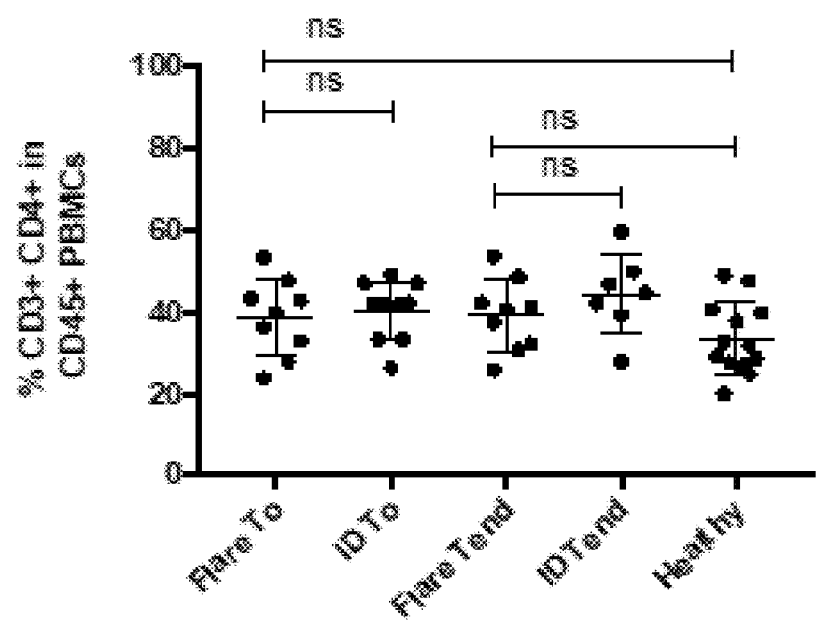
Figure 2F:
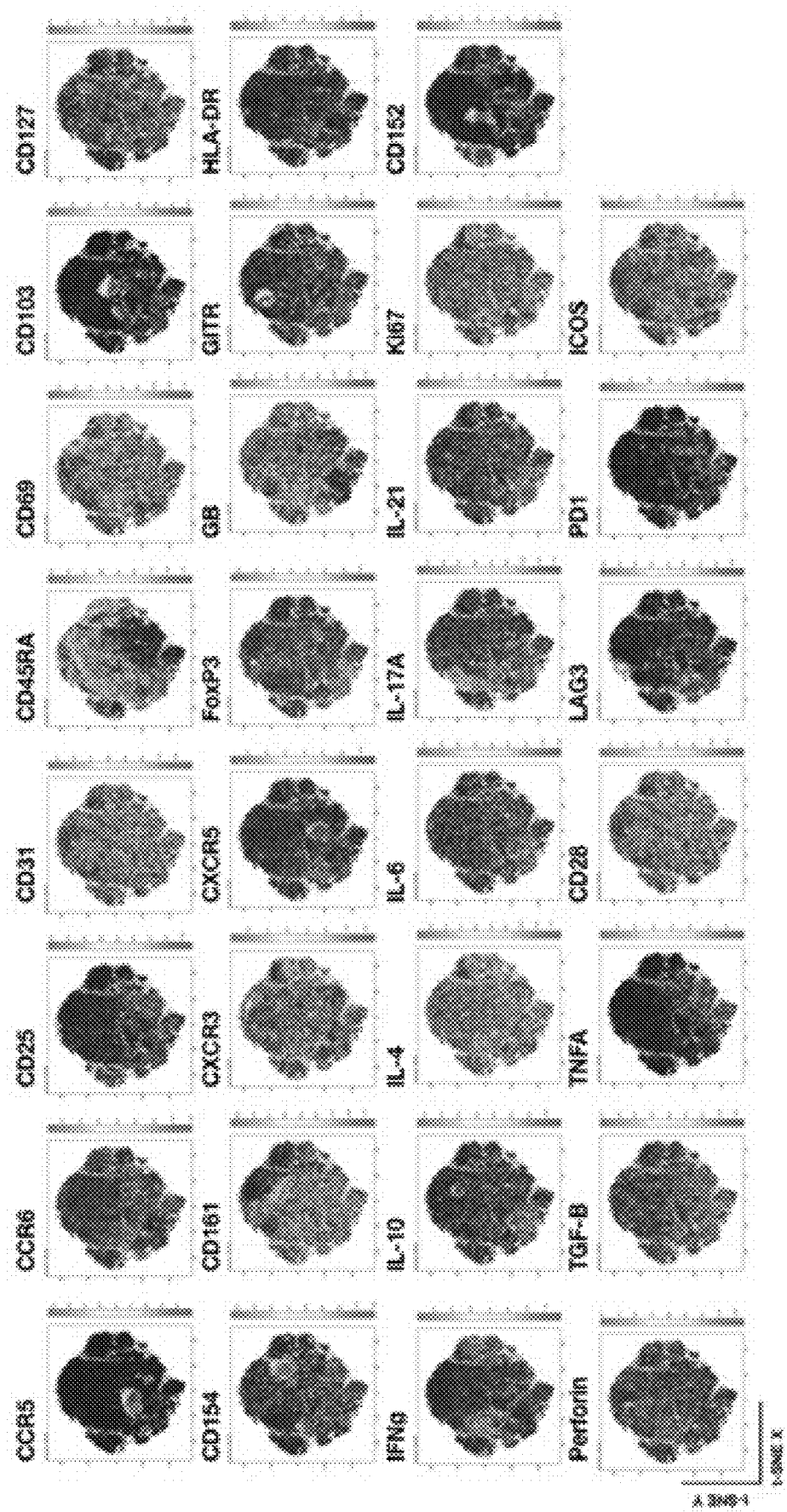

The circulatory PBMC population was investigated through a high dimensional single cell resolution platform, CyToF, with a 31 functional and 6 lineage marker panel (Table 3) consisting mainly of targets meant to interrogate the CD4 T cell compartment. Staining was performed through the usage of barcoding of samples to facilitate pooling of individuals for consistent staining with a master mix. FCS data intensity were normalised with EQ beads, and cells were debarcoded as previously described (V. Chew, et al. *Proc Natl Acad Sci USA* 114, E5900-E5909 (2017)). The results were examined for any gross differences in total CD3+CD4+ populations across the patient categories. No significant changes (FIG. 2E) were detected. The CD4 compartment. CD3+ CD4+ T cells were analysed for any internal differences from flare/inactive ($T_o$) individuals prior to therapy withdrawal. Cell events were normalised and clustered with MarVis, allowing dimensional reduction of 31 functional markers onto a bivariate X-Y axis through t-SNE (FIG. 2F). Clustering of the cells allows for immunophenotypic segregation and categorisation of cellular subsets into distinct nodes (FIG. 1A). Normalised average cell frequency distribution was examined across the nodes and noted an enrichment of cells from flare ($T_o$) individuals within a region of nodes that ranges between 150 to 230 ID (FIG. 1B). These nodes correspond to a region within the t-SNE maps that exhibit CD45RA− TNFA+ expression (FIG. 1C). These CD45RA− TNFA+nodes contain an assortment of cytokines (TNFA, IL-6, IFNg and IL-17A) and immune checkpoint (PD1 and CD152) phenotypes (FIG. 2A-B).

CyToF Interrogation of PBMCs

PBMCs were thawed and stained with a T cell focus panel of 37 heavy metal-conjugated antibodies (Table 3) as described previously (V. Chew, et al. Gut, (2018)) and analysed with Cytometry Time of Flight (CyToF). Briefly, PBMCs were stimulated with or without phorbol 12-myristate 13-acetate (150 ng/ml, Sigma-aldrich) and ionomycin (750 ng/ml, Sigma-aldrich) for 6 hrs, and blocked with secretory inhibitors, briefedin A (1:1000, eBioscience) and monesin (1:1000, Biolegend) for the last 4 hrs, in 10% v/v human serum, 1% v/v PSG, RPMI at 37° C., 5% $CO_2$. The cells were then washed and stained with cell viability dye cisplatin (200 µM, Sigma-aldrich) for 5 mins at room temperature. Cells are then washed and separate individual samples are barcoded with unique combination of anti-CD45 conjugated with either heavy metal 89, 115, 141 or 167 as previously described (L. Lai, et al. *Cytometry A* 87, 369-374 (2015)) for 25 mins on ice. The barcoded cells are then washed and stained with surface antibody cocktail in 4% v/v heat-inactivated FBS, 2 mM EDTA, 0.05% w/v sodium azide in pH 7.4 PBS for 30 mins on ice. The cells are then washed, resuspended in fixation/permeabilisation buffer (1:3, eBioscience) for 45 mins on ice. Permeabilised cells are then stained with intra antibody cocktail (1:10, permeabilisation buffer, eBioscience) for 45 mins on ice. The stained cells are then washed and stained with DNA intercalator Ir-191/193 (1:2000 in 1.6% w/v paraformaldehye, Fluidigm) overnight at 4° C. or 20 mins on ice. Cells are washed and resuspended with EQ™ Four Element Calibration beads (1:10, Fluidigm) in ultra-pure distilled water at $1 \times 10^6$ cells/ml. The cell mixture is loaded and acquired with the Helios mass cytometer (Fluidigm) that is calibrated with CyToF Tunning solution (Fluidigm). The output FCS files are then randomised and normalised with the EQ™ Four Element Calibration beads against the entire run as per manufacturer's recommendation.

Analysis of CyToF Data with MarVis

The normalised output FCS files from CyToF were debarcoded manually in FlowJo (v.10.2) into individual sample, and downsampled to equal cell events for each sample and category (flare, inactive or healthy). Batch run effects were checked with an internal biological control (PBMCs aliquots from the same healthy donor for every run). The normalised cells (minimum 5000 events) were then clustered with Multi-dimensional Automated Reduction and Visualisation (MarVis) using Barnes Hut SNE non-linear dimensional reduction algorithm and k-means clustering algorithm. The default clustering parameters are set at perplexity of 30, and a minimum of p<0.0001. The cells were then mapped on a 2 dimensional t-distributed Stochastic Neighbour Embedding (t-SNE) scale based on their similarity score of their respective combination of markers and categorised into nodes. Node phenotype was read with an R-script that compares the node marker intensity against the entire population of nodes in a histogram layout. Statistical test of nodes was performed with Mann Whitney two tail test and defined as significant for p<0.05. To ensure the significant nodes obtained from clustering were relevant, back-gating of the clustered CSV file was performed in addition to supervised gating of the original FCS files with FlowJo as validation.

TABLE 3

CyToF antibody panel used in staining of PBMCs from JIA patients/controls. Details of antibody clone and vendor used in the CyToF staining of PBMCs are as listed.

| Targets | Metal Channel | Clone | Antibody Vendor/Catalogue number |
|---|---|---|---|
| Lineage markers | | | |
| CD3 | 139 | UCHT1 | Biolegend (300402) |
| CD4 | 148 | SK3 | Biolegend (344625) |
| CD8 | 144 | SK1 | Biolegend (344727) |
| CD11b | 161 | ICRF44 | Biolegend (301302) |
| CD16 | 209 | 3G8 | Fluidigm (3209002B) |
| CD14 | 112/114 | M5E2 | Biolegend (301843) |
| T helper subsets | | | |
| IL-4 | 156 | 8D4-B | Biolegend (500707) |
| IFN-g | 168 | B27 | Biolegend (506513) |
| IL-17A | 169 | BL168 | Biolegend (512302) |
| IL-21 | 151 | 3A4-N2 | Biolegend (513009) |
| CD161 | 157 | HP-3G10 | Biolegend (339902) |
| T cell functional markers | | | |
| CD45RA | 171 | HI100 | Biolegend (304102) |
| CD69 | 176 | FN50 | Biolegend (310902) |
| CD28 | 146 | CD28.2 | Biolegend (302923) |
| CD152 (CTLA4) | 155 | BNI3 | Biolegend (555851) |
| CD154 (CD40L) | 149 | 24-31 | Biolegend (310835) |
| HLA-DR | 143 | L243 | Biolegend (307612) |
| LAG3 | 159 | 17B4 | Abcam (ab40466) |
| PD1 | 147 | EH12.2H7 | Biolegend (329941) |
| Ki67 | 166 | 20Raj1 | Thermofisher/ebioscience (14-5699-82) |
| ICOS | 154 | C398.4A | Biolegend (313512) |
| CD31 | 172 | WM59 | Biolegend (303102) |
| CD103 | 142 | B-Ly7 | Thermofisher/ebioscience (14-1038-82) |
| Chemokine receptors | | | |
| CXCR3 | 163 | G025H7 | Biolegend (353718) |
| CXCR5 | 160 | RF8B2 | BD biosciences (552032) |
| CCR5 | 145 | NP-6G4 | Abcam (ab115738) |
| CCR6 | 170 | G034E3 | Biolegend (353402) |
| Treg markers | | | |
| CD25 | 150 | M-A251 | BD biosciences (555429) |
| CD127 | 153 | A019D5 | Biolegend (351302) |
| FoxP3 | 165 | PCH10L | Thermofischer/ebioscience (14-4776-82) |
| GITR | 164 | 621 | Biolegend (311602) |
| TGF-B (LAP) | 175 | TW4-2F8 | Biolegend (349602) |
| IL-10 | 158 | JES3-9D7 | Biolegend (501402) |
| Cytokines/Enzymes | | | |
| TNF-alpha | 152 | Mab11 | Biolegend (502902) |
| IL-6 | 162 | MQ2-13A5 | Thermofischer/ebioscience (16-7069-86) |

TABLE 3-continued

CyToF antibody panel used in staining of PBMCs from JIA patients/controls. Details of antibody clone and vendor used in the CyToF staining of PBMCs are as listed.

| Targets | Metal Channel | Clone | Antibody Vendor/ Catalogue number |
|---|---|---|---|
| Granzyme B | 173 | CLB-GB11 | Abcam (ab103159) |
| Perforin | 174 | B-D48 | Abcam (ab47225) |
| Barcodes | | | |
| CD45-A | 89 | HI30 | Fluidigm (3089003B) |
| CD45-B, C or D | 115, 141, 167 | HI30 | Biolegend (304002) |
| Live/Dead/Singlets | | | |
| DNA (Singlets) | 191/193 | Nil | Fluidigm Cell-ID Intercalator-Ir (201192B) |
| Cisplatin (Live/Dead) | 195 | Nil | Sigma-aldrich (479306-1G) |

Figure 3:
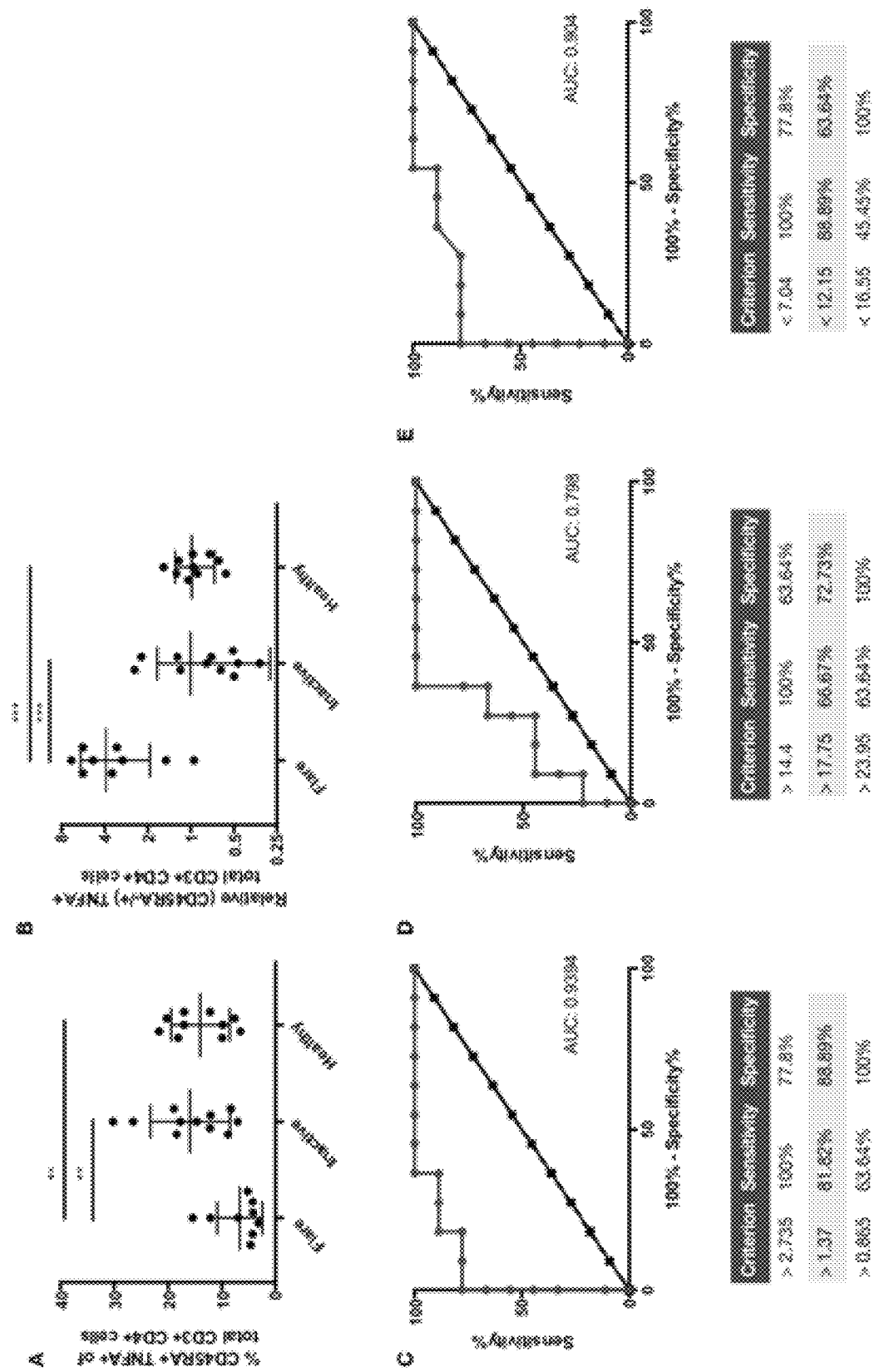
FIG. 3: Construction of Receiver Operating Characteristic curve for predicting clinical fate. (A) We manually gated from the FCS files and calculated the cell frequency of native $CD45RA^+$ $TNFA^+$ as percentage of total CD3+ $CD4^+$ cells in flare, inactive ($T_o$) or healthy individuals. (B) The ratio of memory CD45RA− $TNFA^+$/naive $CD45RA^+$ $TNFA^+$ cells of total $CD3^+$ CD4+ cells in flare, inactive ($T_o$) or healthy individuals is depicted. Construction of a Receiver Operating Characteristic (ROC) curve with (C) the ratio of CD4RA− $TNFA^+$/$CD45RA^+$ $TNFA^+$, (D) $CD45RA^-$ $TNFA^+$, (E) $CD45RA^+$ $TNFA^+$ cells of total $CD3^+$ CD4+ cells from flare versus inactive ($T_o$) individuals, with the AUC and tabulated sensitivity/specificity shown.
Figure 4:
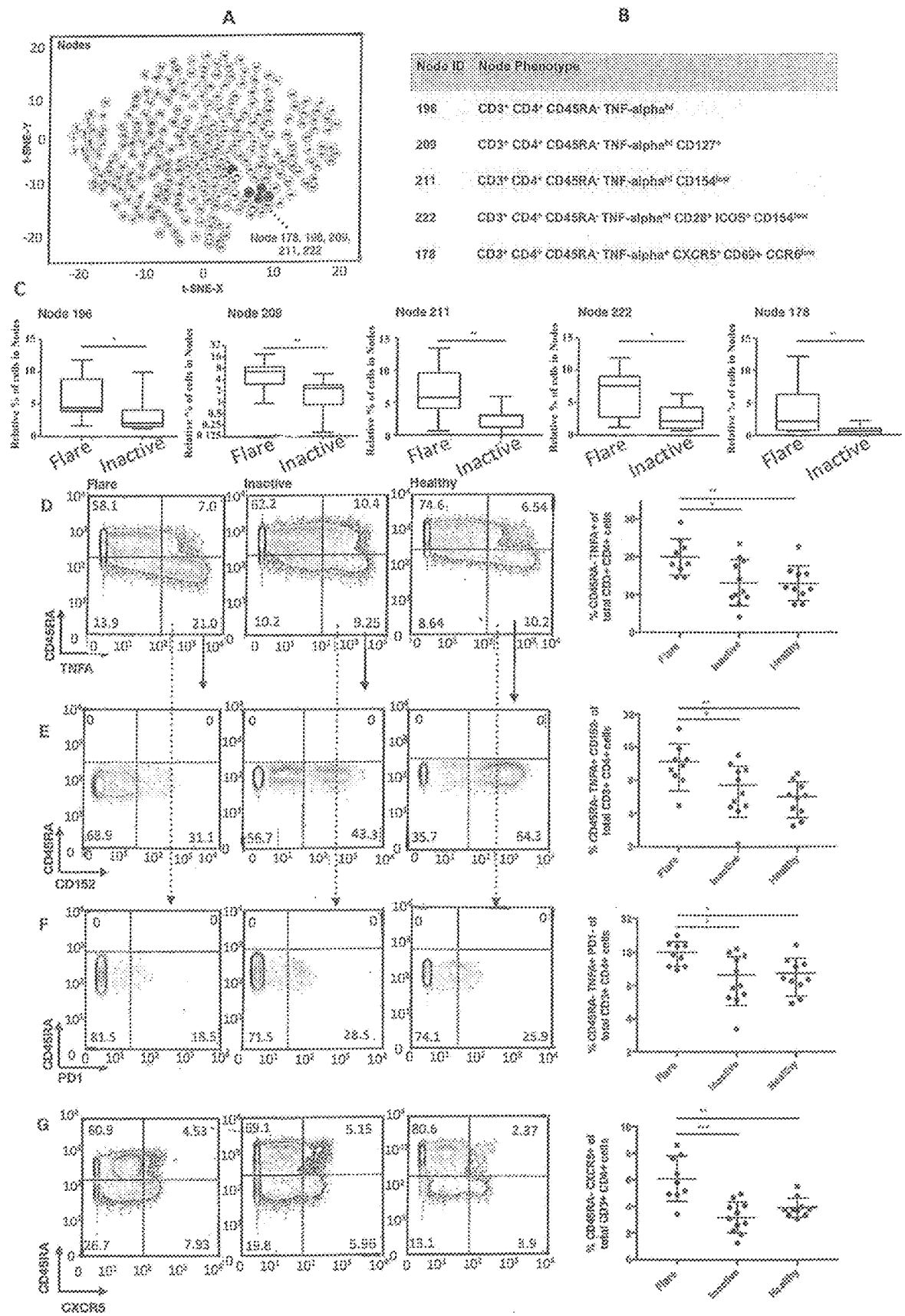
FIG. 4: Statistical filtering and validation of nodes significantly enriched in flare ($T_o$) patients within the CD45RA− TNFA+ region. (A) The location of the five nodes (196, 209, 211, 222, 178) within the CD45RA− TNFA+ region that is significantly higher in flare versus inactive ($T_o$) individuals. (B) Table depicting node phenotype of the significant nodes. (C) Box plots of cell frequency from individuals. Manual gating of the FCS files from flare/inactive ($T_o$) individuals was performed to validate the following populations, (D) $CD45RA^-$ $TNFA^+$, (E) $CD45RA^-$ $TNFA^+$ $CD152^-$, (F) $CD45RA^-$ $TNFA^+$ $PD1^-$ and (G) $CD45RA^-$ $CXCR5^+$. Mann Whitney two tail test, means±S.D., *p<0.05, p<0.01,  p<0.001. (H) Histograms depicting expression of markers within nodes enriched in flare versus inactive ($T_o$) individuals. Node phenotype of statistically significant nodes 196, 209, 211, 222, 178, (enriched in flare individuals as compared with inactive ($T_o$) individuals) within the CD45RA− $TNFA^+$ region. Red line depicts expression of marker within node, black line depicts expression of marker across all nodes in t-SNE map.
Figure 4H:
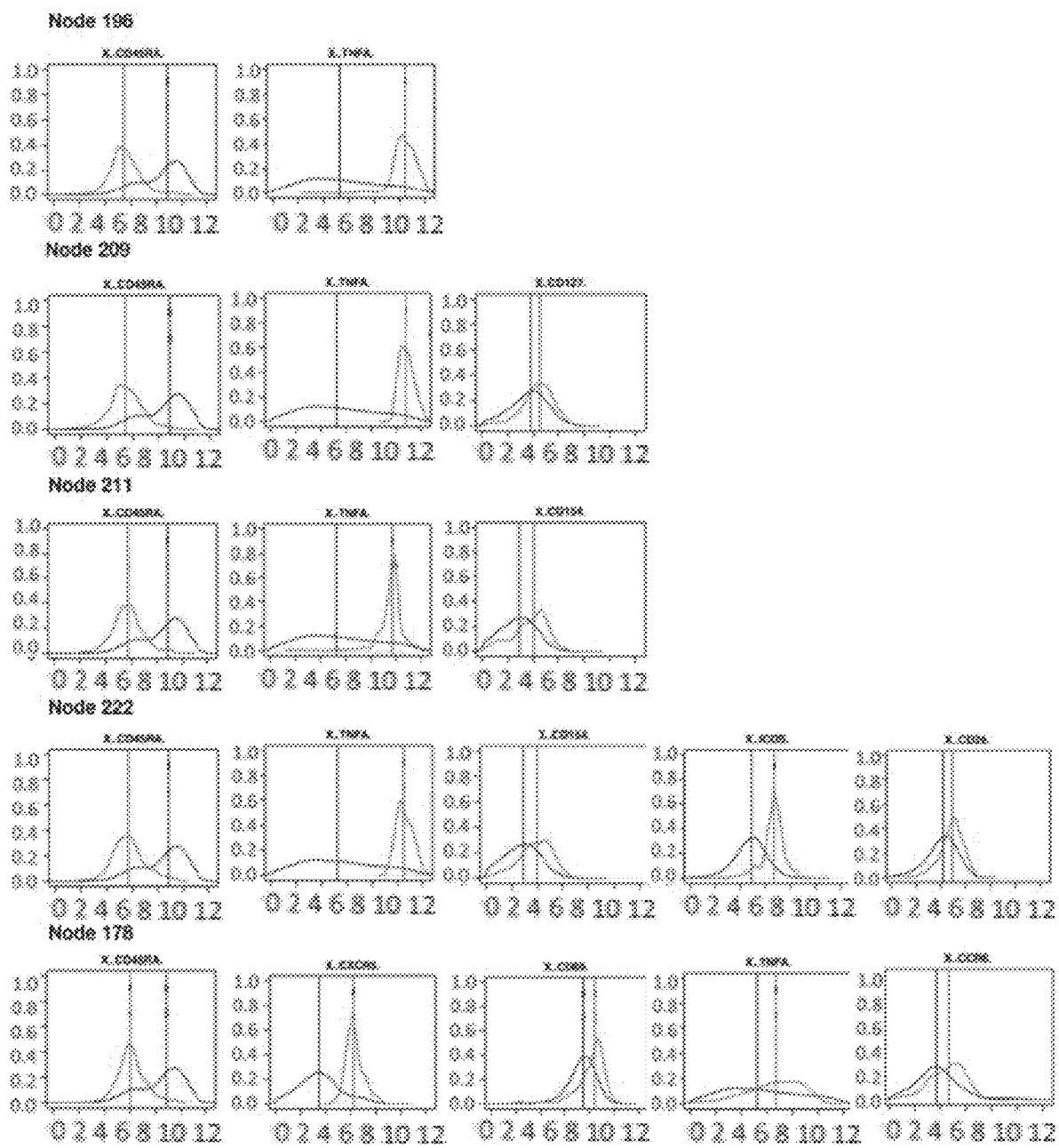

Example 3: Clinical Predictive Value of $CD3^+CD4^+$ $CD45RA^-$ TNFA+Subset in this Discovery Cohort $T_o$ investigate the possibility of using the cell frequency of $CD3^+CD4+CD45RA^-$ TNFA+subset in this discovery cohort as a predictor of flaring ($T_o$) as compared with remaining inactive ($T_o$), an internal individual gating control was developed in the construction of a ROC curve. It was noted that inactive ($T_o$)/healthy individuals reflect significantly higher frequencies of naive CD45RA+TNFA+ cells as compared to flare ($T_o$) individuals (FIG. 3A). The lower levels of naive CD45RA+TNFA+subsets in individuals who will flare ($T_o$) could possibly be due to egress from circulation. The inverse relationship between $CD45RA^-$ TNFA+ and CD45RA+TNFA+for flare/inactive ($T_o$) individuals allows for a clear and significant segregation of patients when utilising the ratio of $CD45RA^-$ TNFA+/CD45RA+ TNFA+ subsets (FIG. 3B). Utilising this ratio, we constructed a ROC curve (flare versus inactive ($T_o$) individuals) of 0.939 AUC with 81.82% sensitivity and 88.89% specificity for the criterion at 1.37 (FIG. 3C). Construction of ROC curve with only either the $CD45RA^-$ TNFA+ (AUC=0.798, FIG. 3D) or CD45RA+ TNFA+ (AUC=0.904, FIG. 3E) from flare versus inactive ($T_o$) individuals is less superior. Overall the ROC curve supports the clinical predictive utility of this persistent pathogenic CD3+ CD4+ CD45RA− TNFA+subset in how clinicians can manage drug withdrawal decisions.

Example 4 CD3+ CD4+ CD45RA− TNFA+ PD1− CD152− Memory Persistence Despite Therapy To determine how flare/inactive ($T_o$) cells are differentially segregated within this region of CD45RA− TNFA+ cells, flare or inactive ($T_o$) CD45RA− TNFA+ cells were back-gated onto the t-SNE map (FIG. 2C-D) which show that most cells from flare ($T_o$) individuals map onto the enriched region displaying a focused node distribution as opposed to the diffuse distribution of inactive ($T_o$) individuals. Flare ($T_o$) individuals tend to focus strongly within nodes that are purely $CD45RA^-$ $TNFA^+$, whereas inactive ($T_o$) individuals tend to exhibit a mix distribution of cells that express $CD45RA^-$ $TNFA^+$ with/without $CD152^+$, $PD1^+$ or $Ki67^+/IL-10^+$ phenotypes. Nodes 196, 209, 211, 222, 178 are significantly enriched (p<0.05 or 0.01) in flare ($T_o$) individuals as compared with inactive ($T_o$) individuals (FIG. 4A-C, FIG. 4H) and were mainly expressing purely a $CD45RA^-$ $TNFA^+$ background and notably were devoid of other cytokines (IFN-g, IL-17, IL-6) and immune checkpoints (PD1, CD152). The absence of PD1 and CD152 in nodes 196, 209, 211, 222 indicate a possible deficit in immune checkpoint control that may have contributed to the persistence of these CD4 memory cells. Particularly node 178 exhibits expression of CXCR5*, implicating possible T-B cell interaction. To ensure these nodes are not due to artefacts generated from the process of clustering analysis, validation of targets was performed through manual gating (FIG. 4D-G) in CD3+CD4+ T cells for the following populations (a) $CD45RA^-$ $TNFA^+$, (b) $CD45RA^-$ $TNFA^+$ $CD152$, (c) $CD45RA^-$ $TNFA^+$ $PD1^-$ and (d) $CD45RA^-$ $CXCR5^+$, and were found to be significantly higher (p<0.05, 0.01 or 0.001) in flare ($T_o$) versus inactive ($T_o$)/healthy individuals. Overall substantial persistence in $CD3^+$ $CD4^+$ $CD45RA^-$ $TNFA^+$ $PD1^-$ $CD152^-$ memory subsets were observe in flare ($T_o$) individuals that likely contribute to disease persistence.

In this study, a heterogenous pool of JIA individuals was recruited from patients that successfully achieved inactive disease on medication (anti-TNFA). Further sub-segregation of the patients into their clinical fate after drug withdrawal, resulted in identifying a group of patients that may fail to resolve their disease despite therapy. Applying the high dimensional single cell resolution CyToF platform, it was discovered from a heterogenous pool of circulatory CD4 T cells, a group of inflammatory $CD3^+$ $CD4^+$ $CD45RA^-$ $TNFA^+$ $PD1^-$ $CD152^-$ memory T cells that persisted despite therapy. The persistence of this subset allowed us to discriminate flare and inactive patients with a ROC curve. It would seem that in flare patients, the extra-cellular neutralisation of TNFA with anti-TNFA biologics is insufficient to "reset" these inflammatory memory cells. It is postulated, but unknown as of now, whether a higher drug dose or longer duration of clinical remission on medication will ultimately serve to shut down these inflammatory cells. However, once cells have a remission signature it the patience from whom the cells have been taken from may have the drug treatment withdrawn with minimal fear of the disease flaring up again. The neutralisation of the inflammatory cytokine, TNFA, may also require the parallel resolution through immune checkpoint signalling. Indeed the evolution of immune blockade therapies (anti-PD1, anti-CD152) in cancer patients have now resulted in a new class of rheumatic disease (L. Calabrese, and X. Mariette, T. *Ann Rheum Dis* 77, 162-164 (2018)), termed as rheumatic immune-related adverse events (irAEs).

Figure 5A:
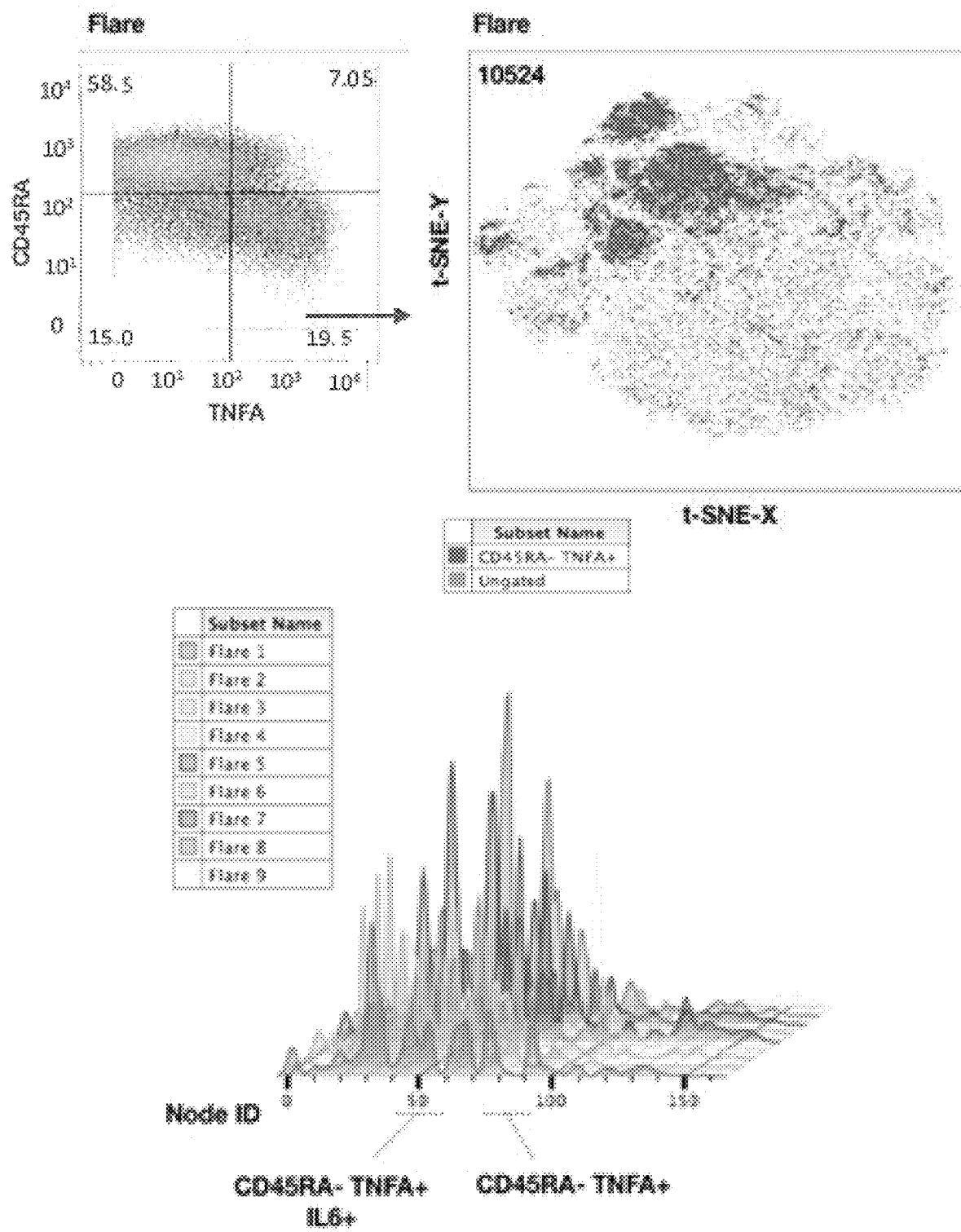
FIG. 5: Clustering of flare ($T_o$) and healthy cells with MarVis. (A) $CD3^+$ $CD4^+$ T cells from flare ($T_o$) and (B) healthy individuals were normalised and clustered with MarVis. We back-gated $CD45RA^-$ $TNFA^+$ cells onto the t-SNE map, and visualised the cell frequency distribution of individuals across nodes. The relevant gated cells expressing (C) cytokines (IFNg, IL-17A and IL-6) and (D) immune checkpoints (PD1, CD152) within the $CD45RA^-$ $TNFA^+$ region are depicted on the t-SNE map. Nodes 48, 49, 76 and 77 were statistically significant; with the (E) location on t-SNE map, (F) phenotype and (G) box plots of cell frequency from individuals is shown. (H) Manual gating of FCS files from flare/inactive ($T_o$) and healthy was performed to validate CD45RA− TNFA+ IL-6+ population. Mann Whitney two tail test, means S.D., * p<0.05 and **p<0.01, (1) Histograms depicting expression of markers within nodes enriched in flare ($T_o$) versus healthy individuals. Node phenotype of statistically significant nodes 48, 49, 76, 77, (enriched in flare ($T_o$) individuals as compared with healthy individuals) within the CD45RA⁻ TNFA⁺ region. Red line depicts expression of marker within node, black line depicts expression of marker across all nodes in t-SNE map.
Figure 5B:
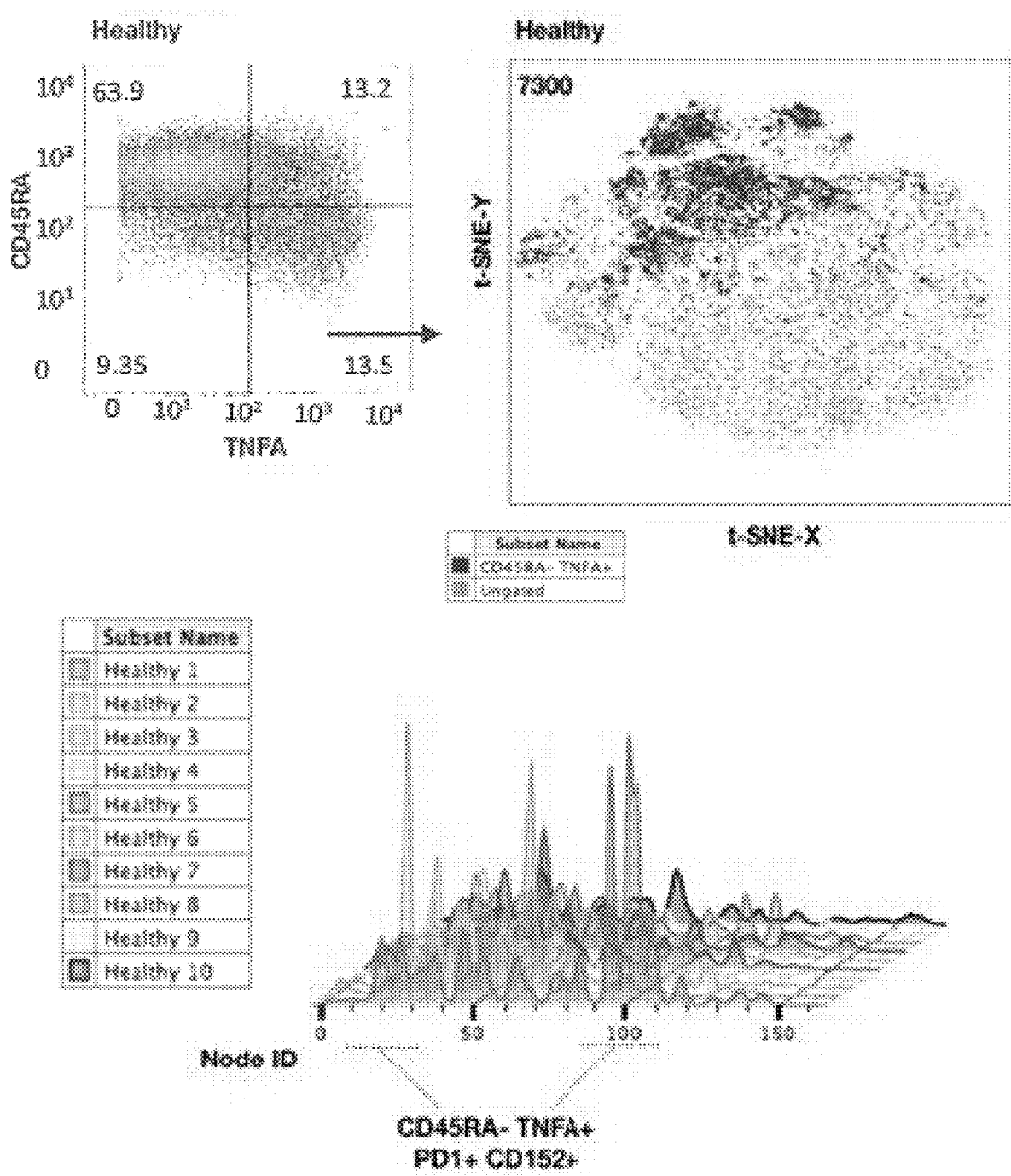
Figure 5C:
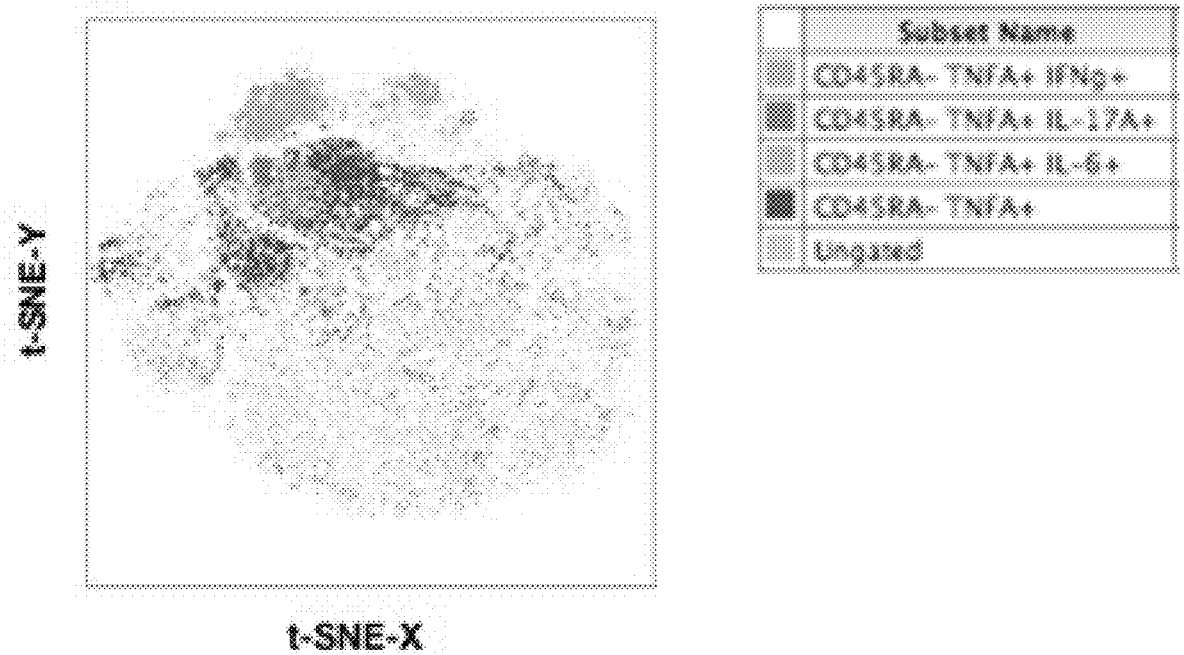
Figure 5D:
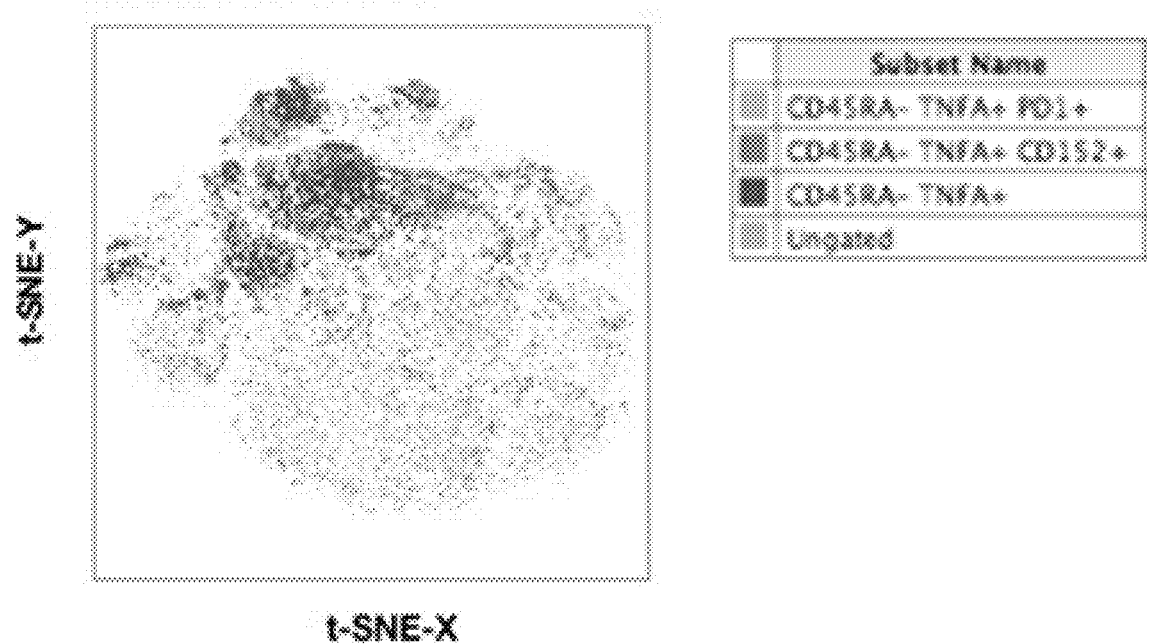

Example 5 Presence of Subclinical Disease CD3+CD4+CD45RA− TNFA+ IL-6+Subset in Flare Individuals Comparing flare with inactive ($T_o$) individuals has the vulnerability of masking subtle subclinical CD4 T cell subsets that are present in both underlying disease background. To avoid this masking, flare ($T_o$) were compared with healthy paediatric individuals that have no inflammatory conditions, in an attempt to uncover subclinical subsets. Clustering of CD3+CD4+ cells from flare ($T_o$) and healthy non-disease individuals onto the t-SNE map reveal similar dysregulation at the level of $CD45RA^-$ $TNFA^+$ cells (FIG. 5A-B), with notable enrichment particularly in flare individuals. The nodes within this region is segregated based on the expression of cytokines (IFNg, IL-17A and IL-6, FIG. 5C) and immune checkpoint expression (PD1, CD152, FIG. 5D). Particularly flare individuals reflect a focused distribution in nodes which exhibit purely $CD45RA^-$ $TNFA^+$ or double positive for $TNFA^+$ $IL-6^+$ that is devoid of PD1 or CD152. Nodes 48, 49, 76 and 77 were significantly enriched (p<0.05 or 0.01) from flare ($T_o$) individuals as compared with healthy individuals (FIG. 5E-G, FIG. 5I). Nodes 48 and 49 express CD45RA− TNFA+ PD1− CD152− phenotype, whereas nodes 76 and 77 reflect CD45RA⁻ TNFA⁺ IL-6⁺ PD1⁻ CD152⁻ expression. Manual gating of FCS files reconfirms the clustering results, indicating that flare individuals are indeed enriched (p<0.001) with CD45RA⁻ TNFA⁺ IL-6⁺ (FIG. 5H). As the presence of this double positive subset was not detected previously in flare versus inactive ($T_o$) comparison, this subset likely represent a subclinical disease subset that is only revealed upon comparison with healthy non-disease individuals. Indeed when flare and inactive ($T_{end}$) individuals were examined after therapy withdrawal, the presence of CD45RA⁻ TNFA⁺/IL-6⁺ double positive cells are significantly increased in patients upon flaring (FIG. 7A-B). The consequent detection and emergence of this double positive subset is likely due to overt disease manifestation, which previously was subclinical. When comparing flare and inactive ($T_{end}$) individuals after withdrawal of therapy, up-regulation of PD1/CD152 was also observed, likely as a response to inflammation in flare individuals (FIG. 7B-E, node 45). Though this up-regulation in PD1/CD152 in flare individuals seems inadequate as the levels are similar to healthy individuals (FIG. 7F-G) who are not experiencing inflammation.

When flare JIA patients are compared with paediatric healthy controls (non-JIA), a sub-clinical population of double positive TNFA⁺/IL-6⁺ (CD3⁺ CD4⁺ CD45RA⁻ PD1⁻ CD152⁻) memory T cells becomes observable. This population emerges upon overt flare manifestation (during drug withdrawal), previously not detectable when comparing flare with inactive individuals prior to drug withdrawal. Notably in a recent case-series report of 3 cancer individuals on immune blockade therapy (S. T. Kim, et al. *Ann Rheum Dis* 76, 2061-2064 (2017)) who subsequently develop severe polyarthritis, were successfully treated with tocilizumab (anti-IL-6). This reflects the overall commonality we observe in inflammatory and resolution mechanisms in both autoimmunity and cancer therapy.

Example 6: Memory T Regulatory Subsets Compensating for Disease

In light of the regulatory role of Tregs in JIA, total $T_{reg}$ population were also examined (FIG. 6A) in patients prior and after withdrawal of therapy to determine if any dysregulation could be observed. Interestingly total $T_{reg}$ populations were not significantly altered in patients prior to or after withdrawal of therapy (FIG. 6B-C). Though we noted that the memory CD45RA⁻ subset of $T_{regs}$ (FIG. 6D-E) is significantly increased (p<0.05) in flare ($T_o$) as compared with inactive ($T_o$)/healthy individuals prior to withdrawal of therapy, and to a lesser extent after withdrawal of therapy ($T_{end}$) as compared to healthy individuals. The enrichment of CD45RA⁻ memory $T_{reg}$ could be a compensatory but likely inadequate response to subclinical inflammation ongoing in patients who will eventually flare upon discontinuation of therapy.

A compensatory heightened response in CD45RA⁻ T regulatory populations was also detected in individuals who flare. Others have shown that synovium T effectors are resistant to T regulatory suppression (S. Haufe, et al. *Arthritis Rheum* 63, 3153-3162 (2011)), and this T effector resistance is alleviated in patients under anti-TNFA therapy (E. J. Wehrens, et al. *Arthritis Rheum* 65, 3279-3284 (2013)). This indicates that individuals destined to flare upon therapy withdrawal experience sub-clinical inflammation that is marked by parallel compensatory T regulatory response that is possibly aiding in controlling inflammation during treatment but not sufficient to completely resolve the disease. The subsequent removal of anti-TNFA therapy in flare patients may have allowed T effector resistance to T regulatory suppression to re-surface. Intriguingly anti-IL-6 appears to remove T effector resistance to T regulatory suppression in a subset of JIA patients (Wehrens, et al.). The skewing of T regulatory TCR repertoire in JIA patients has been extensively demonstrated (M. Rossetti, et al. *Ann Rheum Dis* 76, 435-441 (2017)), and a recent mice study with single cell RNAseq revealed TCR clonotypic restriction in the types of T regulatory phenotypes (D. Zemmour, et al. *Nat Immunol* 19, 291-301 (2018)).

Figure 8B:
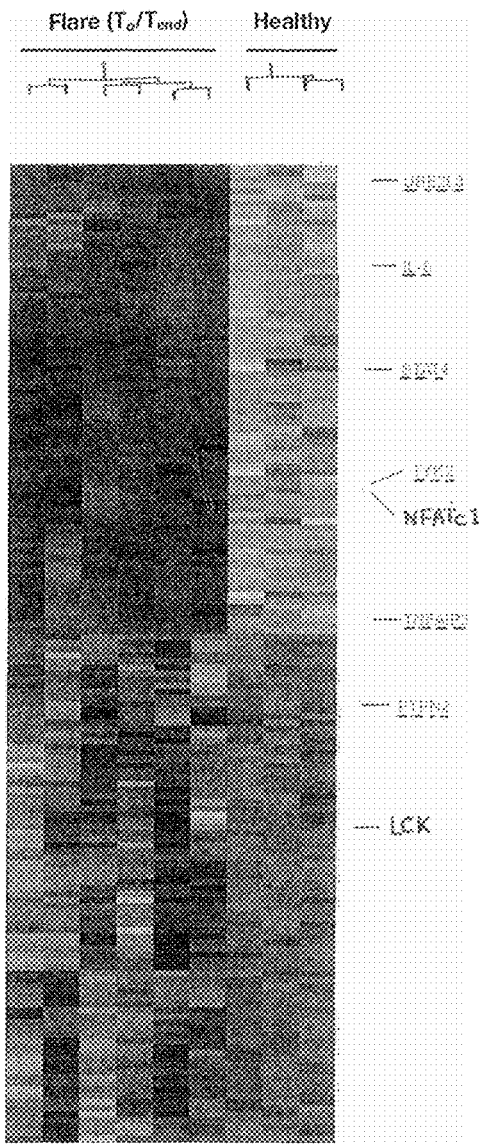
FIG. 8: Sort strategy for CD3+ CD4⁺ CD14⁻ CD45RO⁺ CD45RA⁻ cells in FACS Ariall. (A) PBMCs were thawed and stained with respective antibodies and sort for CD3⁺ CD4⁺ CD45RA⁻ CD45RO⁺ T cells was performed with FACS Aria II. Non-singlets and dead cells were excluded as shown. Equal numbers of sorted CD3+ CD4⁺ CD14⁻ CD45RO⁺ CD45RA⁻ T cells from 6 flare ($T_o/T_{end}$), 6 inactive ($T_o/T_{end}$) JIA patients and 3 healthy paediatric controls were stimulated for 24 hrs with anti-CD3/CD28, and subjected to mRNA analysis with Nanostring Immunology V2 panel. Heatmap depicting genes significantly ($p<0.05$, fold difference±1.5) increased in (B) flare or (C) inactive ($T_o/T_{end}$) JIA patients as compared with healthy controls. Note genes highlighted in blue; are enriched in inactive individuals, in red; previously described in GWAS studies, in green; mentioned in discussion.
Figure 8C:
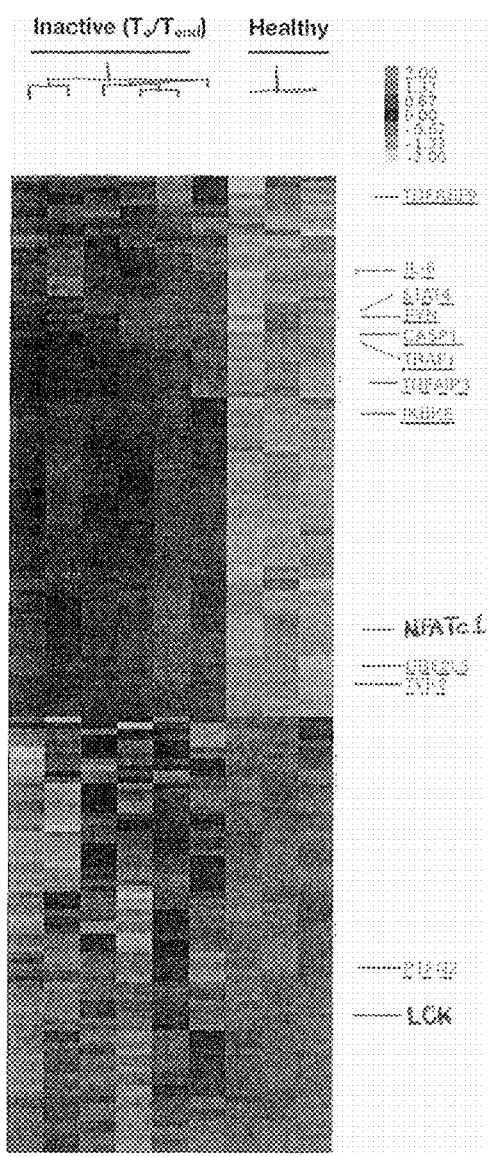
Figure 9A:
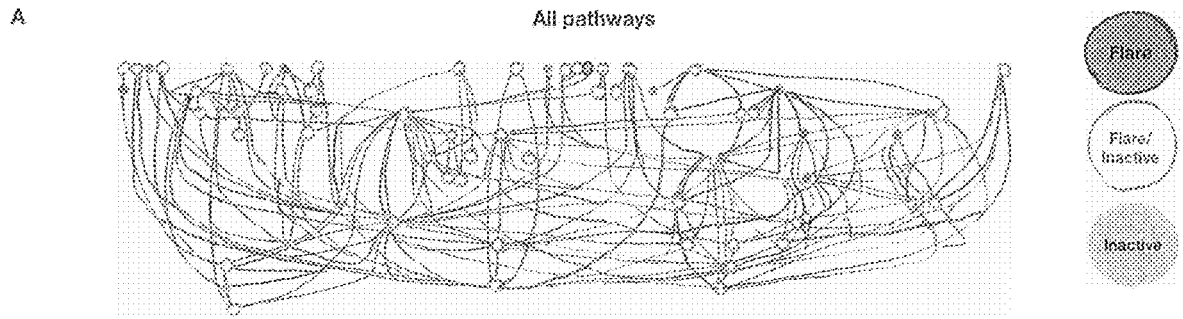
FIG. 9: Pathways enrichment of persistent genes. (A) Genes enriched in JIA patients were exported to DAVID for functional gene set enrichment, and gene associations were constructed with Cytoscape using the Reactome database. Five major pathways, (B) TCR activation, (C) TNFA signalling, (D) NF-kB signalling, (E) apoptosis, (F) MAPK signalling) are dysregulated in flare and inactive JIA patients as compared with healthy controls (red=flare only, yellow=flare or inactive, blue=inactive only). Genes enriched in inactive individuals; [1] Fyn, [2]TRAF1, [3]TNFRSF9, [4]CASP1, [5]IKBKE. Equal numbers of sorted CD3⁺ CD4⁺ CD14⁻ CD45RO⁺ CD45RA⁻ T cells from 4 paired JIA patients pre (treatment naive) or post (recent onset clinical remission) to anti-TNFA therapy and 3 healthy paediatric controls were stimulated for 24 hrs with anti-CD3/CD28, and subjected to mRNA analysis with Nanostring Immunology V2 panel. (G) Heatmap depicting genes significantly ($p<0.05$, fold difference±1.5) increased in JIA patients as compared with healthy controls. (H) Genes enriched in JIA patients were exported to DAVID for functional gene set enrichment, and gene associations were constructed with Cytoscape using the Reactome database. Five major pathways (TCR activation, apoptosis, TNFA signalling, NF-kB signalling, MAPK signalling) are dysregulated in JIA patients as compared with healthy controls.

Example 7 Persistence of gene dysregulation in CD3⁺ CD4⁺ CD45RA⁻ T cells despite therapy and successful clinical control The persistence of CD3⁺ CD4⁺ CD45RA⁻ TNFA⁺ T cells in JIA individuals, despite achieving clinical remission with biologics therapy, leads to determining if there is a parallel subset of genes that remains dysregulated throughout therapy. Equal number of CD3⁺ CD4⁺ CD45RA⁻ CD45RO⁺ T cells were sorted (FIG. 8) from flare (n=6)/inactive (n=6) ($T_o/T_{end}$) and healthy individuals (n=3) and stimulated 24 hrs with anti-CD3/CD28. The mRNA profiles of the cells were screened with the aid of Nanostring using a targeted panel consisting of over 500 immunological genes. A collection of genes that remain dysregulated were detected (p<0.05, fold difference±1.5) despite therapy in flare ($T_o/T_{end}$) (FIG. 8B) or inactive ($T_o/T_{end}$) individuals (FIG. 8C). Dysregulation in UBE2L3, IL-6, STAT4, TYK2, TNFAIP3, and PTPN2 expression was observed in both flare and inactive individuals, which has been previously reported to be associated with JIA (A. Hinks, et al. *Nat Genet* 45, 664-669 (2013)). Functional gene enrichment was performed with DAVID on the genes enriched in JIA patients (flare/inactive) versus healthy, and 5 major pathways were found to be dysregulated, (a) TCR activation, (b) apoptosis, (c) TNFA signalling, (d) NF-kB signalling and (e) MAPK signalling in both flare (Table 4) and inactive (Table 5) individuals.

TABLE 4

DAVID functional gene set enrichment of genes enriched in flare ($T_o/T_{end}$) individuals. DAVID functional gene set enrichment was performed for genes enriched in flare ($T_o/T_{end}$) individuals as compared with healthy individuals, with default setting against a human background. Pathways implicated are tabulated for gene counts ≥4

| Category | Term | Count | % | P-Value | Benjamin |
|---|---|---|---|---|---|
| TCR activation | | | | | |
| KEGG-PATHWAY | T cell receptor signaling pathway | 10 | 13.2 | 4.7E−07 | 3.9E−06 |
| GOTERM_BP_DIRECT | T cell receptor signaling pathway | 8 | 10.5 | 4.3E−06 | 3.5E−04 |

TABLE 4-continued

DAVID functional gene set enrichment of genes enriched in flare ($T_o/T_{end}$) individuals.
DAVID functional gene set enrichment was performed for genes enriched in flare ($T_o/T_{end}$) individuals as compared with healthy individuals, with default setting against a human background. Pathways implicated are tabulated for gene counts ≥4

| Category | Term | Count | % | P-Value | Benjamin |
|---|---|---|---|---|---|
| REACTOME_PATHWAY | R-HSA-202424 (Downstream TCR signaling) | 6 | 7.9 | 5.6E−04 | 9.4E−03 |
| BIOCARTA | T Cell Receptor Signaling Pathway | 5 | 6.6 | 4.6E−02 | 2.4E−01 |
| Apoptosis | | | | | |
| UP_KEYWORDS | Apoptosis | 15 | 19.7 | 7.3E−09 | 2.6E−07 |
| GOTERM_BP_DIRECT | apoptotic process | 14 | 18.4 | 1.2E−06 | 1.4E−04 |
| GOTERM_BP_DIRECT | negative regulation of apoptotic process | 11 | 14.5 | 3.3E−05 | 1.8E−03 |
| GOTERM_BP_DIRECT | positive regulation of apoptotic process | 10 | 13.2 | 7.4E−06 | 4.6E−04 |
| GOTERM_BP_DIRECT | regulation of apoptotic process | 9 | 11.8 | 4.8E−06 | 3.5E−04 |
| KEGG_PATHWAY | Apoptosis | 6 | 7.9 | 2.9E−04 | 1.2E−03 |
| GOTERM_BP_DIRECT | apoptotic signaling pathway | 5 | 6.6 | 2.8E−04 | 9.7E−03 |
| GOTERM_BP_DIRECT | activation of cysteine-type endopeptidase activity involved in apoptotic process | 4 | 5.3 | 6.1E−03 | 9.6E−02 |
| BIOCARTA | Neuropeptides VIP and PACAP inhibit the apoptosis of activated T cells | 4 | 5.3 | 4.6E−02 | 2.5E−01 |
| BIOCARTA | Induction of apoptosis through DR3 and DR4/5 Death Receptors | 4 | 5.3 | 8.2E−02 | 3.6E−01 |
| TNF-alpha signalling | | | | | |
| KEGG_PATHWAY | TNF signalling pathway | 15 | 19.7 | 6.7E−13 | 1.0E−10 |
| BIOCARTA | TNFR2 Signaling Pathway | 8 | 10.5 | 4.8E−07 | 7.4E−05 |
| BIOCARTA | TNF/Stress Related Signaling | 8 | 10.5 | 6.2E−06 | 3.2E−04 |
| GOTERM_BP_DIRECT | tumor necrosis factor-mediated signaling pathway | 7 | 9.2 | 1.4E−05 | 8.5E−04 |
| GOTERM_BP_DIRECT | cellular response to tumor necrosis factor | 5 | 6.6 | 1.5E−03 | 3.6E−02 |
| NF-kB signalling | | | | | |
| KEGG_PATHWAY | Toll-like receptor signaling pathway | 11 | 14.5 | 4.8E−08 | 5.3E−07 |
| KEGG_PATHWAY | NF-kappa B signaling pathway | 11 | 14.5 | 7.0E−09 | 1.2E−07 |
| KEGG_PATHWAY | NOD-like receptor signaling pathway | 10 | 13.2 | 1.7E−09 | 5.2E−08 |
| GOTERM_BP_DIRECT | positive regulation of NF-kappaB transcription factor activity | 10 | 13.2 | 7.5E−09 | 2.0E−06 |
| GOTERM_BP_DIRECT | positive regulation of I-kappaB kinase/NF-kappaB signaling | 9 | 11.8 | 5.9E−07 | 7.6E−05 |
| KEGG_PATHWAY | RIG-I-like receptor signaling pathway | 9 | 11.8 | 2.7E−07 | 2.7E−06 |
| REACTOME_PATHWAY | R-HSA-445989 (TAK1 activates NFkB by phosphorylation and activation of IKKs complex) | 8 | 10.5 | 7.8E−10 | 2.0E−07 |
| REACTOME_PATHWAY | R-HSA-168638 (NOD1/2 Signaling Pathway) | 7 | 9.2 | 1.2E−07 | 1.5E−05 |
| KEGG-PATHWAY | Cytosolic DNA-sensing pathway | 7 | 9.2 | 2.9E−05 | 1.6E−04 |
| BIOCARTA | NF-kB Signaling Pathway | 7 | 9.2 | 4.8E−05 | 1.5E−03 |
| REACTOME_PATHWAY | R-HSA-1810476 (RIP-mediated NFkB activation via ZBP1) | 6 | 7.9 | 2.2E−07 | 1.8E−05 |
| REACTOME_PATHWAY | R-HSA-933542 (TRAF6 mediated NF-kB activation) | 6 | 7.9 | 4.5E−07 | 2.8E−05 |
| REACTOME_PATHWAY | R-HSA-2871837 (FCERI mediated NF-kB activation) | 6 | 7.9 | 2.2E−03 | 2.7E−02 |
| GOTERM_BP_DIRECT | nucleotide-binding oligomerization domain containing signaling pathway | 5 | 6.6 | 4.3E−06 | 3.3E−04 |
| GOTERM_BP_DIRECT | I-kappaB kinase/NF-kappaB signaling | 5 | 6.6 | 1.5E−04 | 6.4E−03 |
| GOTERM_BP_DIRECT | NIK/NF-kappaB signalling | 4 | 5.3 | 3.2E−03 | 6.1E−02 |
| GOTERM_BP_DIRECT | negative regulation of NF-kappaB transcription factor activity | 4 | 5.3 | 3.9E−03 | 7.2E−02 |
| REACTOME_PATHWAY | R-HSA-5668541 (TNFR2 non-canonical NF-kB pathway) | 4 | 5.3 | 1.1E−02 | 8.9E−02 |

TABLE 4-continued

DAVID functional gene set enrichment of genes enriched in flare ($T_o/T_{end}$) individuals.
DAVID functional gene set enrichment was performed for genes enriched in flare ($T_o/T_{end}$) individuals as compared with healthy individuals, with default setting against a human background. Pathways implicated are tabulated for gene counts ≥4

| Category | Term | Count | % | P-Value | Benjamin |
|---|---|---|---|---|---|
| MAPK signalling | | | | | |
| KEGG_PATHWAY | MAPK signalling pathway | 9 | 11.8 | 2.8E−03 | 8.9E−03 |
| BIOCARTA | MAPKinase Signaling Pathway | 7 | 9.2 | 5.1E−02 | 2.6E−01 |
| GOTERM_BP_DIRECT | MAPK cascade | 5 | 6.6 | 3.0E−02 | 3E−01 |
| GOTERM_BP_DIRECT | positive regulation of MAPK cascade | 4 | 5.3 | 5.7E−03 | 9.1E−02 |
| GOTERM_BP_DIRECT | activation of MAPK activity | 4 | 5.3 | 1.2E−02 | 1.6E−01 |

Sorting and Culturing of Cells

PBMCs are thawed and stained with CD3-AF700 (UCHT1, Biolegend), CD14-APC/H7 (MφP-9, BD Biosciences), CD4-BV605 (OKT4, Biolegend), CD45RA⁻ PE/Dazzle (H1100, Biolegend), CD45RO-FITC (UCHL1, Biolegend) for 20 mins on ice at 2×106 cells/ml. Cell viability was determined through staining with Sytox Red (1:1000, Thermofisher scientific). $CD3^+$ $CD14^-$ $CD4^+$ $CD45RO^+$ $CD45RA^-$ T cells were sorted with FACS Aria II (BD Biosciences), with the exclusion of doublets and dead cells. The cells were seeded at 4×104 cells per well in a 96 well plate for 24 hrs with soluble tetrameric anti-CD3/CD28 (1:100, Stemcell) in 10% v/v human serum, 1% v/v PSG, RPMI at 37° C., 5% $CO_2$.

Purification of mRNA and Screening with Nanostring

Extraction of mRNA from cells was performed with the Arcturus Picture RNA isolation kit (Thermofisher scientific), according to the manufacture's instructions. Briefly, cells were lysed with extraction buffer for 30 mins at 42° C. The lysate was mixed equal volume with 70% v/v ethanol. The mixture is loaded and bound onto the purification column and digested with DNase I (Qiagen) for 15 mins at room temperature. RNA was washed and eluted. RNA was amplified with nCounter Low RNA Input Amplification kit (Nanostring). Briefly, first strand cDNA synthesis was performed with RT enzyme and primer mix at 42° C. for 60 mins. Next multiplexed target enrichment was performed with gene specific primers (nCounter Immunology panel V2, Nanostring) for 8 cycles. Hybridisation of amplified RNA samples with capture/reporter probes (nCounter Immunology panel v2, Nanostring) at 65° C. for 16 hrs. The samples are then captured onto nCounter chips using the prep station and read with digital analzyer under maximum sensitivity (555 FOVs).

Analysis of Nanostring Data

The RCC files were exported and read with nSlover (v3, Nanostring) software from the manufacturer. Genes were normalised with recommended set of housekeeping genes. Statistical filtering of genes was performed with nSlover (v3, Nanostring), with Welch's t test p<0.05, and fold difference ≥1.5. Significant genes are represented in a heatmap using spearman correlation and exported to Database for Annotation, Visualization and Integrated Discovery (DAVID, v6.8) website. Functional gene enrichment was performed with DAVID under the human background gene list. Genes from clusters of pathways that are significantly represented in DAVID are mapped and graphically represented with the Reactome database using Cytoscape (v3.5.1).

TABLE 5

DAVID functional gene set enrichment of genes enriched in inactive ($T_o/T_{end}$) individuals.
DAVID functional gene set enrichment was performed for genes enriched in inactive ($T_o/T_{end}$)

| Category | Term | Count | % | P-Value | Benjamin |
|---|---|---|---|---|---|
| TCR activation | | | | | |
| KEGG-PATHWAY | T cell receptor signaling pathway | 12 | 13.3 | 1.8E−08 | 1.6E−07 |
| GOTERM_BP_DIRECT | T cell receptor signaling pathway | 10 | 11.1 | 8.8E−08 | 1.4E−05 |
| REACTOME_PATHWAY | R-HSA-202424 (Downstream TCR signaling) | 7 | 7.8 | 1.4E−04 | 3.4E−03 |
| BIOCARTA | T Cell Receptor Signaling Pathway | 7 | 7.8 | 4.6E−03 | 5.2E−02 |
| Apoptosis | | | | | |
| UP_KEYWORDS | Apoptosis | 18 | 20.0 | 1.2E−10 | 6.1E−09 |
| GOTERM_BP_DIRECT | apoptotic process | 17 | 18.9 | 4.2E−08 | 7.2E−06 |
| GOTERM_BP_DIRECT | regulation of apoptotic process | 12 | 13.3 | 1.6E−08 | 3.2E−06 |
| GOTERM_BP_DIRECT | negative regulation of apoptotic process | 12 | 13.3 | 2.8E−05 | 1.3E−03 |
| GOTERM_BP_DIRECT | positive regulation of apoptotic process | 11 | 12.2 | 4.2E−06 | 3.2E−04 |
| KEGG_PATHWAY | Apoptosis | 6 | 6.7 | 6.7E−04 | 2.5E−03 |
| GOTERM_BP_DIRECT | apoptotic signaling pathway | 5 | 5.6 | 5.5E−04 | 1.3E−02 |
| GOTERM_BP_DIRECT | activation of cysteine-type endopeptidase activity involved in apoptotic process | 5 | 5.6 | 9.8E−04 | 2.1E−02 |
| GOTERM_BP_DIRECT | positive regulation of apoptotic signaling pathway | 4 | 4.4 | 3.0E−04 | 9.3E−03 |

TABLE 5-continued

DAVID functional gene set enrichment of genes enriched in inactive ($T_o/T_{end}$) individuals.
DAVID functional gene set enrichment was performed for genes enriched in inactive ($T_o/T_{end}$)

| Category | Term | Count | % | P-Value | Benjamin |
|---|---|---|---|---|---|
| GOTERM_BP_DIRECT | extrinsic apoptotic signaling pathway via death domain receptors | 4 | 4.4 | 1.1E−03 | 2.3E−02 |
| GOTERM_BP_DIRECT | Intrinsic apoptotic signaling pathway in respons to DNA damage | 4 | 4.4 | 2.0E−03 | 3.7E−02 |
| BIOCARTA | Neuropeptides VIP and PACAP inhibit the apoptosis of activated T cells | 4 | 4.4 | 6.8E−02 | 3.1E−01 |
| TNF-alpha signalling | | | | | |
| KEGG_PATHWAY | TNF signalling pathway | 16 | 17.8 | 5.3E−13 | 2.7E−11 |
| BIOCARTA | TNFR2 Signaling Pathway | 9 | 10.0 | 7.1E−08 | 1.1E−05 |
| BIOCARTA | TNF/Stress Related Signaling | 8 | 8.9 | 1.9E−05 | 7.6E−04 |
| GOTERM_BP_DIRECT | tumor necrosis factor-mediated signaling pathway | 7 | 7.8 | 3.8E−05 | 1.7E−03 |
| GOTERM_BP_DIRECT | cellular response to tumor necrosis factor | 6 | 6.7 | 3.0E−04 | 9.3E−03 |
| GOTERM_BP_DIRECT | regulation of tumor necrosis factor-mediated signaling pathway | 4 | 4.4 | 5.3E−04 | 1.3E−02 |
| REACTOME_PATHWAY | R-HSA-5357905 (Regulation of TNFR1 signaling) | 4 | 4.4 | 2.2E−03 | 2.7E−02 |
| NF-kB signalling | | | | | |
| KEGG_PATHWAY | Toll-like receptor signaling pathway | 14 | 15.6 | 1.4E−10 | 3.6E−09 |
| GOTERM_BP_DIRECT | positive regulation of I-kappaB kinase/NF-kappaB signaling | 12 | 13.3 | 8.6E−10 | 2.4E−07 |
| KEGG_PATHWAY | NF-kappa B signaling pathway | 12 | 13.3 | 3.0E−09 | 3.8E−08 |
| KEGG_PATHWAY | NOD-like receptor signaling pathway | 11 | 12.2 | 4.1E−10 | 7.9E−09 |
| GOTERM_BP_DIRECT | positive regulation of NF-kappaB transcription factor activity | 11 | 12.2 | 2.1E−09 | 4.8E−07 |
| KEGG_PATHWAY | RIG-I-like receptor signalling pathway | 11 | 12.2 | 4.9E−09 | 5.7E−08 |
| KEGG_PATHWAY | Cytosolic DNA-sensing pathway | 10 | 11.1 | 3.5E−08 | 3.0E−07 |
| REACTOME_PATHWAY | R-HSA-445989 (TAK1 activates NFkB by phosphorylation and activation of IKKs complex) | 8 | 8.9 | 2.6E−09 | 7.5E−07 |
| REACTOME_PATHWAY | R-HSA-168638 (NOD1/2 Signaling Pathway) | 8 | 8.9 | 1.0E−08 | 1.5E−06 |
| BIOCARTA | NF-kB Signaling Pathway | 7 | 7.8 | 1.2E−04 | 3.9E−03 |
| REACTOME_PATHWAY | R-HSA-1810476 (RIP-mediated NFkB activation via ZBP1) | 6 | 6.7 | 5.0E−07 | 4.8E−05 |
| REACTOME_PATHWAY | R-HSA-933542 (TRAF6 mediated NF-kB activation) | 6 | 6.7 | 1.0E−06 | 7.5E−05 |
| REACTOME_PATHWAY | R-HSA-2871837 (FCERI mediated NF-kB activation) | 6 | 6.7 | 4.5E−03 | 4.9E−02 |
| GOTERM_BP_DIRECT | nucleotide-binding oligomerization domain containing signaling pathway | 5 | 5.6 | 8.6E−06 | 5.4E−04 |
| GOTERM_BP_DIRECT | TRIF-dependent toll-like receptor signaling pathway | 5 | 5.6 | 1.4E−05 | 7.9E−04 |
| GOTERM_BP_DIRECT | I-kappaB kinase/NF-kappaB signaling | 5 | 5.6 | 2.9E−04 | 9.2E−03 |
| GOTERM_BP_DIRECT | NIK/NF-kappaB signaling | 5 | 5.6 | 4.1E−04 | 1.1E−02 |
| REACTOME_PATHWAY | R-HSA-5357956 (TNFR1-induced NFkappaB signaling pathway) | 4 | 4.4 | 1.7E−03 | 2.6E−02 |
| GOTERM_BP_DIRECT | negative regulation of NF-kappaB transcription factor activity | 4 | 4.4 | 6.3E−03 | 9.2E−02 |
| REACTOME_PATHWAY | R-HSA-5668541 (TNFR2 non-canonical NF-kB pathway) | 4 | 4.4 | 1.7E−02 | 1.3E−01 |
| MAPK signalling | | | | | |
| KEGG_PATHWAY | MAPK signalling pathway | 9 | 10.0 | 8.4E−03 | 2.3E−02 |
| GOTERM_BP_DIRECT | MAPK cascade | 7 | 7.8 | 2.7E−03 | 4.6E−02 |
| BIOCARTA | MAPKinase Signaling Pathway | 7 | 7.8 | 9.7E−02 | 3.8E−01 |
| GOTERM_BP_DIRECT | activation of MAPK activity | 5 | 5.6 | 2.5E−03 | 4.4E−02 |
| GOTERM_BP_DIRECT | positive regulation of MAPK cascade | 4 | 4.4 | 9.1E−03 | 1.2E−01 |
| REACTOME_PATHWAY | R-HSA-5673001 (RAF/MAP kinase cascade) | 4 | 4.4 | 6.4E−02 | 3.4E−01 |

Associations between these genes were constructed with Cytoscape using the Reactome database, and considerable overlap was found in the genes involved in the 5 dysregulated pathways in both flare and inactive individuals (FIG. 9A-F). However a divergence within these pathways was also noted, where inactive individuals have additional differentially expressed genes (FYN, TNFRSF9, CASP1, TRAF1, IKBKE) which have been reported to be involved in aiding in termination or resolution of these pathways in other diseases or infections. These additional resolution mechanisms coupled with numerical difference in cell frequency may explain why certain individuals flare or remain inactive despite therapy. The similarity in the overlap of the pathways in both flare and inactive individuals may explain their susceptibility to clinical control with continual anti-TNFA therapy. Indeed similar pathways persistenobserved in a separate cohort of active JIA patients (Table 6) from treatment naive stage (pre) until recent onset clinical inactivity (post) with anti-TNFA therapy (FIG. 9G-H and Table 7). ce was

TABLE 6

Active JIA patients disease and medication history. Active JIA patients paired for pre (treatment naive) and post (recent onset clinical remission) with anti-TNFA therapy was sorted for their CD3$^+$ CD4$^+$ CD14$^-$ CD45RA$^-$ CD45RO$^+$ T cells and subjected to mRNA analysis with Nanostring

|  | Patient ID | Date | Disease | age | Disease Duration (yrs) | Gender | Joints | ESR | CRP | Medication history |
|---|---|---|---|---|---|---|---|---|---|---|
| Poly JIA | RD00444 | 25 Jul. 2016 | Poly JIA, RF+ | 16.5 | 11.8 | F | 5 | Not done | Not done | Sulfasalazine, MTX, Folic acid, HCQ |
|  | RD00444 | 10 Feb. 2017 | Poly JIA, RF+ | 17.0 | 12.4 | F | 0 | 48 | 2 | MTX, Folic acid, Enbrel |
|  | RD05137 | 11 Mar. 2016 | Poly JIA, RF+ | 10.9 | 0.1 | F | 4 | 26 | 1.5 | — |
|  | RD05137 | 15 Sep. 2016 | Poly JIA, RF+ | 11.4 | 0.6 | F | 0 | 7 | <0.2 | Enbrel, MTX, Folic acid |
| Oligo JIA | RD04080 | 13 Apr. 2016 | Oligo JIA, Extended | 13.6 | 2.4 | F | 4 | 47 | 18.2 | MTX, Prednisolone, Omeprazole, Folic acid |
|  | RD04080 | 26 Oct. 2016 | Oligo JIA, Extended | 14.1 | 2.9 | F | 0 | 21 | 5.7 | MTX, Folic acid, Enbrel |
|  | RD05336 | 4 Aug. 2016 | Oligo JIA, Extended | 1.9 | 0.1 | F | 8 | 97 | 49.2 | Brufen |
|  | RD05336 | 10 Feb. 2017 | Oligo JIA, Extended | 2.4 | 0.6 | F | 0 | 8 | 0.4 | Enbrel |

TABLE 7

DAVID functional gene set enrichment of genes enriched in active JIA (Pre/Post) individuals. DAVID functional gene set enrichment was performed for genes enriched in JIA (pre/post) individuals subjected to anti-TNFA therapy as compared with healthy individuals, with default setting against a human background. Pathways implicated are tabulated for gene counts ≥4.

| Category | Term | Count | % | P-Value | Benjamin |
|---|---|---|---|---|---|
| TCR activation | | | | | |
| KEGG-PATHWAY | T cell receptor signaling pathway | 8 | 15.1 | 3.2E−06 | 2.8E−05 |
| GOTERM_BP_DIRECT | T cell receptor signaling pathway | 7 | 13.2 | 6.2E−06 | 5.8E−04 |
| REACTOME_PATHWAY | R-HSA-202424 (Downstream TCR signaling) | 5 | 9.4 | 1.2E−03 | 2.2E−02 |
| BIOCARTA | T Cell Receptor Signaling Pathway | 4 | 7.5 | 4.9E−02 | 2.1E−01 |
| Apoptosis | | | | | |
| GOTERM_BP_DIRECT | apoptotic process | 14 | 26.4 | 1.2E−08 | 3.8E−06 |
| UP_KEYWORDS | Apoptosis | 13 | 24.5 | 6.9E−09 | 2.9E−07 |
| GOTERM_BP_DIRECT | regulation of apoptotic process | 9 | 17.0 | 2.7E−07 | 4.3E−05 |
| GOTERM_BP_DIRECT | positive regulation of apoptotic process | 7 | 13.2 | 3.2E−04 | 1.2E−02 |
| GOTERM_BP_DIRECT | negative regulation of apoptotic process | 7 | 13.2 | 2.7E−03 | 6.8E−02 |
| KEGG_PATHWAY | Apoptosis | 6 | 11.3 | 4.1E−05 | 2.7E−04 |
| GOTERM_BP_DIRECT | activation of cysteine-type endopeptidase activity involved in apoptotic process | 5 | 9.4 | 1.3E−04 | 5.6E−03 |

TABLE 7-continued

DAVID functional gene set enrichment of genes enriched in active JIA (Pre/Post) individuals.
DAVID functional gene set enrichment was performed for genes enriched in JIA (pre/post) individuals
subjected to anti-TNFA therapy as compared with healthy individuals, with default setting
against a human background. Pathways implicated are tabulated for gene counts ≥4.

| Category | Term | Count | % | P-Value | Benjamin |
|---|---|---|---|---|---|
| BIOCARTA | Neuropeptides VIP and PACAP inhibit the apoptosis of activated T cells | 4 | 7.5 | 1.2E−02 | 7.5E−02 |
| BIOCARTA | Induction of apoptosis through DR3 and DR4/5 Death Receptors | 4 | 7.5 | 2.3E−02 | 1.2E−01 |
| TNF-alpha signalling | | | | | |
| KEGG_PATHWAY | TNF signalling pathway | 11 | 20.8 | 7.5E−10 | 2.2E−08 |
| BIOCARTA | TNF/Stress Related Signaling | 8 | 15.1 | 1.7E−07 | 1.0E−05 |
| BIOCARTA | TNFR2 Signaling Pathway | 6 | 11.3 | 1.3E−05 | 4.0E−04 |
| GOTERM_BP_DIRECT | cellular response to tumor necrosis factor | 4 | 7.5 | 4.8E−03 | 9.9E−02 |
| GOTERM_BP_DIRECT | tumor necrosis factor-mediated signaling pathway | 4 | 7.5 | 5.8E−03 | 1.1E−01 |
| NF-kB signalling | | | | | |
| KEGG_PATHWAY | NF-kappa B signaling pathway | 11 | 20.8 | 1.0E−10 | 1.5E−08 |
| KEGG_PATHWAY | Toll-like receptor signaling pathway | 11 | 20.8 | 7.5E−10 | 2.2E−08 |
| KEGG_PATHWAY | RIG-I-like receptor signalling pathway | 10 | 18.9 | 3.5E−10 | 1.7E−08 |
| GOTERM_BP_DIRECT | positive regulation of 1-kappaB kinase/NF-kappaB signaling | 10 | 18.9 | 1.4E−09 | 1.3E−06 |
| GOTERM_BP_DIRECT | positive regulation of NF-kappaB transcription factor activity | 8 | 15.1 | 1.7E−07 | 3.1E−05 |
| KEGG_PATHWAY | NOD-like receptor signaling pathway | 9 | 17.0 | 1.4E−09 | 3.3E−08 |
| REACTOME_PATHWAY | R-HSA-168638 (NOD1/2 Signaling Pathway) | 7 | 13.2 | 1.2E−08 | 2.7E−06 |
| REACTOME_PATHWAY | R-HSA-933542 (TRAF6 mediated NF-kB activation) | 6 | 11.3 | 6.6E−08 | 7.5E−06 |
| REACTOME_PATHWAY | R-HSA-445989 (TAK1 activates NFkB by phosphorylation and activation of IKKs complex) | 6 | 11.3 | 2.2E−07 | 1.6E−05 |
| BIOCARTA | NF-kB Signaling Pathway | 6 | 11.3 | 4.8E−05 | 1.2E−03 |
| REACTOME_PATHWAY | R-HSA-1810476 (RIP-mediated NFkB activation via ZBP1) | 5 | 9.4 | 2.2E−06 | 1.0E−04 |
| REACTOME_PATHWAY | R-HSA-2871837 (FCERI mediated NF-kB activation) | 5 | 9.4 | 3.6E−03 | 4.7E−02 |
| GOTERM_BP_DIRECT | nucleotide-binding oligomerization domain containing signaling pathway | 4 | 7.5 | 6.1E−05 | 3.6E−03 |
| GOTERM_BP_DIRECT | toll-like receptor signaling pathway | 4 | 7.5 | 7.8E−05 | 4.0E−03 |
| GOTERM_BP_DIRECT | TRIF-dependent toll-like receptor signaling pathway | 4 | 7.5 | 8.7E−05 | 4.3E−03 |
| GOTERM_BP_DIRECT | NIK/NF-kappaB signalling | 4 | 7.5 | 1.1E−03 | 3.4E−02 |
| MAPK signalling | | | | | |
| KEGG_PATHWAY | MAPK signalling pathway | 8 | 15.1 | 1.0E−03 | 4.6E−03 |
| BIOCARTA | MAPKinase Signaling Pathway | 7 | 13.2 | 4.9E−03 | 3.9E−02 |
| BIOCARTA | Human Cytomegalovirus and Map Kinase Pathways | 4 | 7.5 | 3.6E−03 | 3.3E−02 |
| GOTERM_BP_DIRECT | activation of MAPK activity | 4 | 7.5 | 4.4E−03 | 9.4E−02 |
| GOTERM_BP_DIRECT | MAPK cascade | 4 | 7.5 | 4.7E−02 | 4.3E−01 |

The TCR mediated response of CD4 memory T cells in flare and inactive individuals have been tested and the mRNA signature profiled with a pre-selected panel of 500 over immunological genes. There was strong dysregulation in gene expression with $CD3^+$ $CD4^+$ $CD45RO^+$ $CD45RA^-$ memory T cells in JIA patients (flare/inactive) as compared with healthy controls. Several of these genes (UBE2L3, IL-6, STAT4, TYK2, TNFAIP3, and PTPN2) were previously shown by others in large cohort studies to be highly associated with JIA (A. Hinks, et al. *Nat Genet* 45, 664-669 (2013)). The patients recruited were amendable to anti-TNFA therapy, achieving clinical remission on medication treatment with anti-TNFA therapy. Functional gene enrichment and mapping of pathways revealed dysregulation in 5 major pathways (TCR activation, apoptosis, TNFA, NF-kb, MAPK signalling), though considerable overlap is seen between flare and inactive individuals, a divergence in certain points of the pathways was observed. Specifically significantly higher expression of several genes in inactive individuals was detected (FYN, TRAF1, TNFRSF9, IKBKE, CASP1). FYN has been reported to be involved in negative feedback inhibition of TCR signalling through PAG/CBP in FYN$^{-/-}$ mice (A. Filby, et al *J Immunol* 179, 4635-4644 (2007)), and studies show that T cell anergy can be mediated through FYN-PAG interaction (D. Davidson, et al. *Mol Cell Biol* 27, 1960-1973 (2007)). The knockdown of FYN via a glucocorticoid and IP3-mediated calcium signalling pathway resulted in enhanced autophagy in T lymphocytes (M. W. Harr, et al. *Autophagy* 6, 912-921 (2010)). Notably in reduced LCK expression, autoimmunity develops in FYN$^{-/-}$ mice (R. J. Salmond, et al. *Immunol Rev* 228, 9-22 (2009)), and LCK reduction was observed in both flare and inactive individuals (FIG. 9). Genome wide association studies and genotyping studies have revealed the genomic association of the TRAF1-C5 locus with JIA (H. M. Albers, et al. *Ann Rheum Dis* 67, 1578-1580 (2008)). Strong epigenetic dysregulation was detected within the TRAF1 locus of CD4 T cells, with complex interactions with transcription factors and presence of histone markers (L. Zhu, et al. *Arthritis Res Ther* 19, 57 (2017)). TRAF1$^{-/-}$ mice reveal that TRAF1 plays a negative regulatory role in T cells in response to TCR and TNFA signalling (E. N. Tsitsikov, et al. *Immunity* 15, 647-657 (2001)). TRAF1$^{-/-}$ T cells displayed enhanced proliferation in response to TCR and TNFA stimulation, in particular hyper-responsive downstream TNFA signalling towards NF-kB and AP-1 activation. Engagement of CD137 (TNFRSF9) results in depression of CD4$^+$ responses to LCMV via IL-10 during the early phase of viral infection (B. Zhang, et al. *J Clin Invest* 117, 3029-3041 (2007)). CD137 signalling can induce apoptosis through induction of CD95L on CD4 T cells (T. Ebata, et al. *Eur J Immunol* 31, 1410-1416 (2001)), while siRNA knockdown of CD137 diminished TNFA induced apoptosis in dengue infected cells (A. Nagila, et al. *Virol J* 10, 105 (2013)). While agnostic activation of CD137 with antibodies in a variety of autoimmune mice models for rheumatoid arthritis, lupus and EAE proves beneficial, its mechanism of action seem multivariate (D. S. Vinay, and B. S. Kwon, *Expert Opin Ther Targets* 20, 361-373 (2016)). IKBKE has been shown to a negative regulator in limiting chronic inflammation in metabolic and atherosclerotic disease through reduced priming of the NLRP3 inflammasome in macrophages (M. N. Patel, et al. *Proc Natl Acad Sci USA* 112, 506-511 (2015)). In T cells, IKBKE inhibits NFAT activity that is downstream of TCR activity, where a reduction of IKBKE enhanced anti-viral and anti-tumour T cell response (J. Zhang, et al. *Cell Rep* 16, 405-418 (2016)). Higher expression levels of NFATc1 were observed in both flare and inactive individuals (FIG. 9), IKBKE phosphorlation of NFATc1 will inhibit nuclear translocation, thus limiting robust T cell activation. CASP1 a key driver of pyroptosis, has been shown to be pivotal in CD4 T cell depletion during HIV infection (G. Doitsh, et al. *Nature* 505, 509-514 (2014)). Overall, inactive individuals although displaying similar dysregulated pathways as compared with flare individuals, do also diverge in certain key gene expression points.

Candidate pathogenic cellular targets are provided that explain why certain JIA individuals fail to resolve their disease despite seemingly successful anti-TNFA therapy and no visible clinical symptoms. With a growing population of JIA patients achieving clinical remission on medication, monitoring these subsets during long term therapy may provide a better measurement of subclinical inflammation and be instrumental to withdrawal strategies. Divergence in key pathways illustrate the importance in understanding how inactive individuals managed to resolve their disease, and may provide concurrent therapeutic targets with anti-TNFA treatment.

Example 8: Project Approach

Clinical fate: Polyarticular JIA Patients were recruited through the "Improved Understanding of the Biology and Use of TNF inhibition in Children with JIA Trial". These patients previously on anti-TNFA therapy were firstly assessed to be quiescent in disease activity (at least 6 months) and subjected to discontinuation of therapy for a period of 8 months. Patients are then segregated into the clinical response (flare, active and inactive) after completion of trial.

Immunomics: To decipher the CD4 T cell mechanisms that will delineate JIA patients into their clinical fate (flare, active and inactive), we adopted a high-dimensional single cell resolution platform, CyToF (Cytometry Time of Flight) to interrogate circulatory T cell subsets prior and after therapy discontinuation.

Methodology:

Clinical Trial: Patients treated with anti-TNF-alpha were recruited into the study (Improved Understanding of the Biology and Use of TNF inhibition in Children with JIA Trial) with clinically inactive disease on treatment (Wallace criteria) and initiated with therapy discontinuation. The patients were followed and evaluated. They were first scored for disease activity/inactivity using Wallace criteria based on 6 JIA core set parameters; number of joints with active arthritis and/or loss of motion, MD global assessment of current disease activity, patient/parent global assessment of overall disease severity in prior week, a validated measure of physical function and ESR and if they are exhibiting disease they are subsequently scored for flare based on the same criteria but with a severity score. Hence, those exhibiting disease are essentially categorized into active and flare depending on the severity.

Experiment: PBMCs from JIA patients from the trial were taken prior to and after therapy discontinuation, and are stained with a comprehensive T cell panel. These cells were stained with heavy metal conjugated antibodies and acquired through the CyToF machine. The raw data is normalised and processed, and analysed through an in-house modified software architecture MARVis (Multi-Dimensional Automated Reduction Visualization). MARVis clustering of the 37 markers onto a bivariate X-Y axis through dimensional reduction via TSNE (Barts Hut SNE algorithm), allows segregation of cells into distinct node phenotypes. Statistical categorical comparison of patients (flare, active and inactive) determines the node enrichment for their respective categories. Node phenotype is then obtained through the RScript software environment.

Results: PBMCs from 47 JIA patients (Flare=18, Active=11, Inactive=18) and 14 healthy controls were stained and interrogated with CyToF. We have observed distinct CD4 Memory dsyregulation (p<0.05) within patients who are destined to flare (prior to therapy withdrawal). Within this CD4 Memory compartment, flare patients (vs inactive/healthy) experienced higher frequency (p<0.05) of (a) CD3+ CD4+ CD45RA− (Memory) TNFA$^+$, (b) CD3$^+$ CD4$^+$ CD45RA$^-$ (Memory) CXCR5+(TfH: T follicular helper), and the populations are skewed towards (c) CD152$^-$/PD1$^-$. The CD3$^+$ CD4$^+$ Memory TNFA$^+$ cells are believed to be the main inflammatory drivers for the disease, and directly correlating with disease therapy and response. The CD3$^+$ CD4$^+$ Memory CXCR5$^+$ TfH are cells that are known to aid in B cell interaction/activation, and likely to be an early wave of pathogenic cells, as they were not significantly dsyregulated after flare manifestation (after therapy discontinuation; vs inactive/healthy). Immune checkpoint regulators such as CD152 and PD1 aid in disease control, and skewing of CD4 memory subsets in flare patients indicate inadequate immune regulation in disease. Comparison of flare vs healthy individuals, additionally revealed the presence of a subclinical disease subset, CD3$^+$ CD4$^+$ CD45RA$^-$ (Memory) TNFA$^+$ IL-6$^+$ double positive (p<0.05) that was not apparent during flare vs inactive comparison prior to therapy discontinuation. This double positive (TNFA$^+$ IL-6$^+$) subset likely represent alternative inflammatory pathways in patients destined to flare. While comparing active vs inactive patients we noticed a unique migratory population of CD3+ CD4$^+$ CD45RA$^-$ CXCR3$^+$ CCR6$^+$ T cells that likely represent a very early wave of inflammatory subset, as they were not found to be dysregulated in flare vs inactive/healthy due to possible egression from circulation. Upon full flare manifestation (vs inactive) after therapy discontinuation, additional higher spectrum of inflammatory markers were expressed (CD3$^+$ CD4$^+$ CD45RA$^-$ (Memory) IL-21$^+$ IFNg$^+$ TNFA$^+$; p<0.05), that likely participate during disease amplification. In addition, CD4 Memory subsets during flare manifestation exhibit higher levels of CD152$^+$/PD1$^+$ cells as a response to ongoing inflammation versus inactive, but are comparable to healthy levels though disproportionate for what is required to suppress inflammation.

T cell populations isolated from Flare vs Inactive patients prior to withdrawal of therapy were compared. T cell populations isolated from Flare patients prior to withdrawal of therapy were compared to T cell populations from healthy subjects.

Figure 10C:
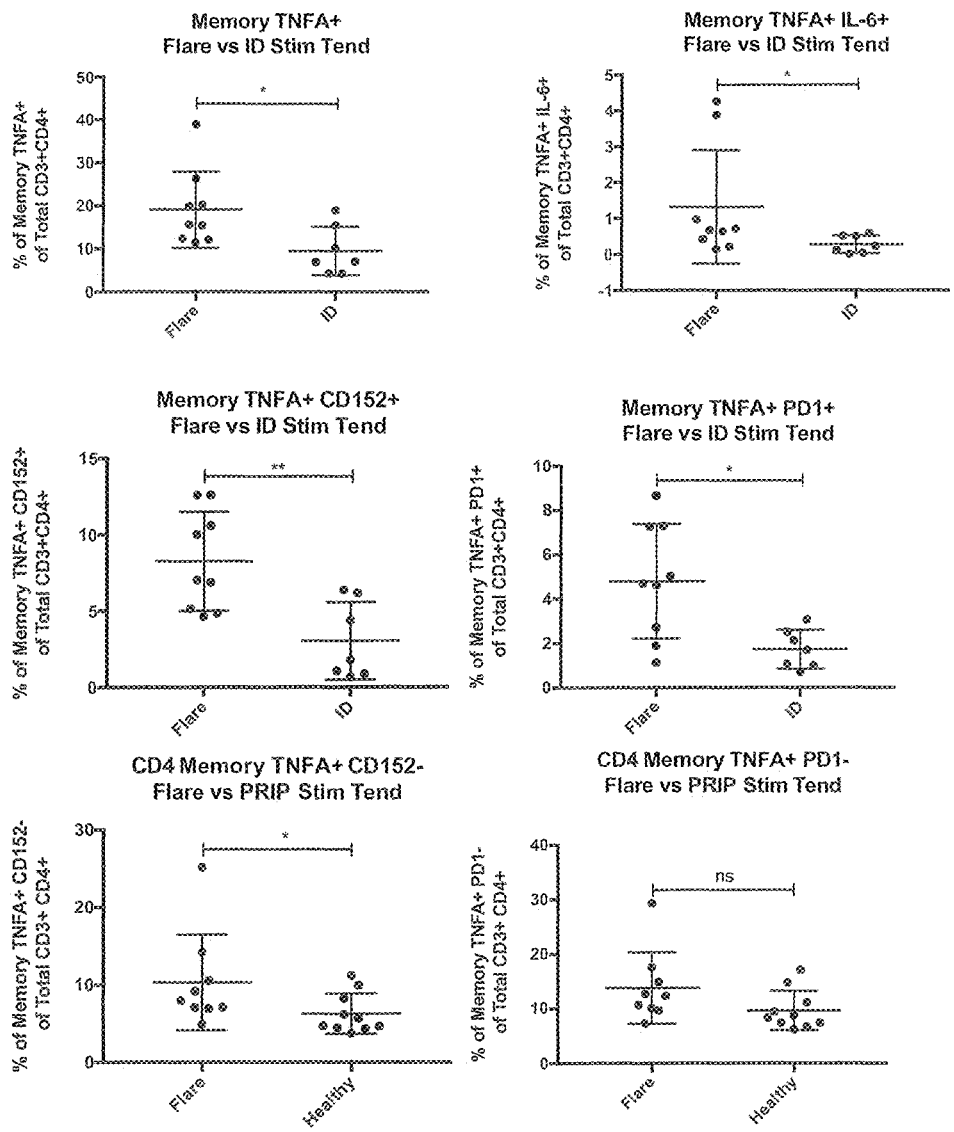
FIG. 10: Supervised gating of various markers in total T cell memory cells in comparative populations (A) comparing flare and inactive in samples taken prior to withdrawal of therapy, (B) comparing flare samples taken prior to withdrawal of therapy with samples from healthy subjects, (C) comparing flare and inactive in samples taken after withdrawal of therapy, and (D) comparing active and inactive in samples taken prior to withdrawal of therapy.

Distinct dysregulation in CD4 Memory subsets in patients destined to flare were observed. CD4 Memory TNFA$^+$ cells are likely inflammatory and directly impacting disease activity. CD4 Memory TNFA$^+$ IL-6$^+$ cells represents a subclinical disease subset that may serve to amplify the disease through alternative pathways CD4 Memory CXCR5$^+$ (TfH) may enhance memory persistence through B cell interaction (Table 8, FIG. 10A-B).

TABLE 8

Enriched node subsets in flare patients prior to withdrawal of therapy

| | Flare vs inactive | Flare vs healthy |
|---|---|---|
| 1 | CD3$^+$ CD4$^+$ CD45RA$^-$ TNFA$^+$ | CD3$^+$ CD4$^+$ CD45RA$^-$ TNFA$^+$ |
| 2 | CD3$^+$ CD4$^+$ CD45RA$^-$ CXCR5+ | CD3$^+$ CD4$^+$ CD45RA$^-$ TNFA$^+$ IL-6$^+$ |
| 3 | | CD3$^+$ CD4$^+$ CD45RA$^-$ CXCR5$^+$ |

T cell populations isolated from Flare vs Inactive patients after withdrawal of therapy were compared. Upon Flare manifestation, the subclinical disease subset (CD4+Memory TNFA+ IL-6+) surfaces and more complex inflammatory subsets were observed (Table 9, FIG. 10C).

TABLE 9

Enriched node subsets in flare patients after withdrawal of therapy

| | Flare vs inactive |
|---|---|
| 1 | CD3$^+$ CD4$^+$ CD45RA$^-$ TNFA$^+$ |
| 2 | CD3$^+$ CD4$^+$ CD45RA$^-$ TNFA$^+$ IL-6$^+$ |
| 3 | CD3$^+$ CD4$^+$ CD45RA$^-$ TNFA$^+$ IFN-g$^+$IL-21$^+$ |

Figure 10D:
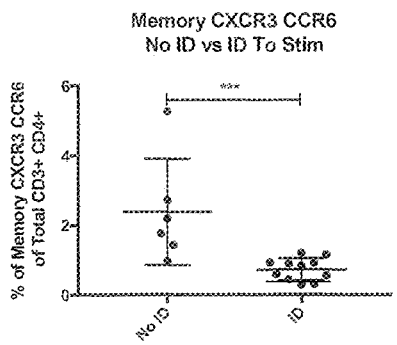

T cell populations isolated from active vs Inactive patients prior to withdrawal of therapy were compared. The migratory subset (CD4$^+$ Memory CXCR3$^+$ CCR6+) enriched only in active patients may represent an early wave of inflammatory infiltrator (thus missed in flare patients due to egression) see table 10 and FIG. 10D.

TABLE 10

Enriched node subsets in active patients before withdrawal of therapy

| | active vs inactive |
|---|---|
| 1 | CD3$^+$ CD4$^+$ CD45RA$^-$ CXCR5$^+$ CCR6$^+$ |

Conclusions: For some patients (flare), anti-TNFA therapy is merely suppressing disease activity and not curative. The persistence of CD4 memory cells are likely to play a pivotal role in disease relapse that may be partially explained by a weaker control through immune checkpoints (CD152/PD1). These results suggest that clinical fate is immunologically predetermined and patients who will develop different clinical fates can be identified from prior biologic sampling.

pJIA patients destined to flare/active upon withdrawal of biologics maintains an enriched population of CD4 Memory cells (TNFA+, TNFA+IL-6+, TNFA+IL-21+, CXCR5+, CXCR3+CCR6+) that persists. Presentation of these subsets are also phase ($T_o/T_{end}$) dependent, a reflection of dynamics within the circulatory system.

For these patients (flare/active), biologics therapy (anti-TNFA) likely aid to control disease manifestation but is not curative.

These CD4+ Memory T cells are skewed towards CTLA4−/PD1−, thus indicating inadequate immune checkpoint control.

Polyarticular JIA patients resembles adult RA patients and may serve to illustrate similar disease pathogenesis in a broader scale of autoimmunity.

In various embodiments the invention relates to a method of evaluating a clinical outcome of a disease in a subject, the method comprises testing a T cell population in a sample obtained from the subject, for at least one biomarker.

In various embodiments the at least one biomarker is selected from the group consisting of: CD3, CD4, CD45RA, TNF-alpha, CXCR5, IL-6, IFN-g, IL-21, CXCR3, CCR6, CD152 and PD1.

In various embodiments the at least one T cell population comprises a CD4+ T cell population.

In various embodiments the CD4+ T cell population comprises a CD4+ memory T cell population.

In various embodiments the CD4+ memory T cell population comprises CD3+ CD4+ CD45RA− memory T cells.

In various embodiments the clinical outcome comprises a flare state, an active state or an inactive state of the disease.

In various embodiments the presence of CD3+ CD4+ CD45RA− TNF-alpha+ T cells indicate a likelihood of a flare state of the disease.

In various embodiments the presence of CD3+ CD4+ CD45RA− TNF-alpha+IL-6+ T cells indicate a likelihood of amplification of the disease.

In various embodiments the presence of CD3+ CD4+ CD45RA− CXCR5+ T cells indicate a likelihood of the flare state of the disease via memory persistence enhancement through B cell interaction.

In various embodiments the presence of CD3+ CD4+ CD45RA− CXCR3+ CCR6+ T cells indicate a likelihood of the active state of the disease.

In various embodiments the presence of CD3+ CD4+ CD45RA− CD152−/PD1− T cells indicates a likelihood of the flare state of the disease due to inadequate immune checkpoint control.

In various embodiments the subject is a patient having a rheumatic disease.

In various embodiments the rheumatic disease is juvenile idiopathic arthritis (JIA).

In various embodiments the juvenile idiopathic arthritis is polyarticular JIA.

In various embodiments the sample is a blood sample.

In various embodiments the blood sample comprises peripheral blood mononuclear cells (PBMCs).

In various embodiments the method comprises exposing the sample to at least one antibody adapted to target the at least one biomarker.

In various embodiments the at least one antibody is a heavy metal conjugated antibody.

In various embodiments the method comprises utilizing Cytometry by Time-Of-Flight (CyToF) to analyze the sample.

In various embodiments the subject has been subjected to an anti-TNF-alpha therapy.

In various embodiments the method is performed prior to withdrawal of the anti-TNF-alpha therapy.

In various embodiments the presence of TNF-ALPHA+ IFN-g+ IL-21+ T cells after the anti-TNF-alpha therapy is withdrawn, indicates a flare state of the disease.

In various embodiments the method is an in vitro method.

In various embodiments the invention relates to a kit for evaluating a clinical outcome of a disease in a subject, the kit comprising at least one antibody adapted to target at least one biomarker on a T cell population in a sample obtained from a subject.

In various embodiments the at least one biomarker is selected from the group consisting of: CD3, CD4, CD45RA, TNF-alpha, CXCR5, IL-6, IFN-g, IL-21, CXCR3, CCR6, CD152 and PD1.

In various embodiments the at least one antibody is a heavy metal conjugated antibody.

It should be further appreciated by the person skilled in the art that variations and combinations of features described above, not being alternatives or substitutes, may be combined to form yet further embodiments falling within the intended scope of the invention.

The invention claimed is:

1. A method of evaluating a clinical outcome of an autoimmune disease in a subject, the method comprising:
   isolating a T cell population comprising CD3+ CD4+ in a sample obtained from the subject;
   testing the T cell population for biomarkers (i) CD45RA and TNF-alpha, and optionally CXCR5, or (ii) CD45RA and CXCR5;
   determining the clinical outcome of the autoimmune disease in the subject, wherein the clinical outcome is indicated by comparing a level of the biomarker TNF-alpha and/or CXCR5 in the T cell population in relation to a predetermined level;
   wherein the predetermined level is expressed in terms of a percentage of the T cell population and is obtained from T cells isolated from a population of healthy subjects or subjects that have recovered from an immunological disease;
   wherein the level of the biomarker TNF-alpha and/or CXCR5 in the T cell population (a) above the predetermined level and in an absence of CD45RA indicates a flare state or an active state of the autoimmune disease; or (b) below the predetermined level and in an absence of CD45RA indicates an inactive state of the autoimmune disease;
   wherein the predetermined level of the biomarker TNF-alpha in the T cell population is at least 10% of the total CD3+CD4+ T cell population; and/or wherein the predetermined level of the biomarker CXCR5 in the T cell population is at least 4% of the total CD3+CD4+ T cell population; and
   (i)(a) selecting a subject determined to be in a flare state, or an active state, of the autoimmune disease, having the level of the biomarker TNF-alpha or CXCR5 in the T cell population above the predetermined level and an absence of CD45RA; and
   (i)(b) treating, or continuing to treat the subject determined to be in a flare state, or an active state, of the autoimmune disease with a biologic disease modifying anti-rheumatic drug; or
   (ii)(a) selecting a subject determined to be in the inactive state of the autoimmune disease, having the level of the biomarker TNF-alpha or CXCR5 in the T cell population below the predetermined level; and
   (ii)(b) withdrawing, or continuing to withhold from treatment with a biologic disease modifying anti-rheumatic drug, the subject determined to be in the inactive state of the autoimmune disease; and
   wherein the autoimmune disease is:
   (a) a rheumatic disease;
   (b) juvenile idiopathic arthritis (JIA);
   (c) rheumatoid arthritis;
   (d) psoriasis;
   (e) psoriatic arthritis; or (f) polyarticular JIA.

2. The method according to claim 1, further comprising: testing the T cell population for one or more additional biomarkers selected from the group consisting of: IL-6, IFN-g, IL-21, CXCR3, CCR6, CD152, PD1, FYN, TNFRSF9 CASP1, TRAF1, and IKBKE.

3. The method according to claims 2, wherein the one or more additional biomarkers tested comprises any one of FYN, TNFRSF9, CASP1, TRAF1, IKBKE and a combination thereof, and wherein the expression of the one or more additional biomarkers selected from any one of FYN, TNFRSF9, CASP1, TRAF1, IKBKE and a combination thereof, in the T cell population above a predetermined level indicates an inactive state of the autoimmune disease.

4. The method according to claim 2, wherein the one or more additional biomarkers tested comprises IL-6, and wherein the level of the biomarker TNF-alpha in the T cell population above a predetermined level, in an absence of CD45RA and the presence of the biomarker IL-6 indicates amplification of the autoimmune disease.

5. The method according to claim 1, wherein the level of the biomarker CXCR5 in the T cell population above a predetermined level and the absence of CD45RA indicates the flare state of the autoimmune disease via memory persistence enhancement through B cell interaction.

6. The method according to claim 2, wherein the one or more additional biomarkers tested comprises CCR6, and wherein the level of the biomarker CXCR5 in the T cell population above a predetermined level, the absence of CD45RA, and the presence of the additional biomarker CCR6 indicates an active state of the autoimmune disease.

7. The method according to claim 2, wherein the one or more additional biomarkers tested comprises CD152 and PD-1, and wherein the absence of the one or more additional biomarkers selected from the group consisting of CD152 and PD1 in the T cell population further indicates a flare state of the autoimmune disease due to inadequate immune checkpoint control.

8. The method according to claim 1, wherein the T cell population is divided into two subsets, a first subset comprising CD3+CD4+CD45RA−TNFA+ and a second subset comprising CD3+CD4+CD45RA+TNFA+; and the method further comprises a) determining an amount of the first subset and an amount of the second subset, and b) calculating a ratio of the amount of the first subset to the amount of the second subset, wherein the ratio in relation to a predetermined ratio of CD3+CD4+CD45RA−TNFA+ T cells to CD3+CD4+CD45RA+TNFA+ T cells identified from a population of healthy subjects or subjects that have recovered from an immunological disease indicates the clinical outcome of the autoimmune disease in the subject.

* * * * *